(12) United States Patent
Linder et al.

(10) Patent No.: US 11,304,964 B2
(45) Date of Patent: Apr. 19, 2022

(54) BOLAAMPHIPHILIC COMPOUNDS, COMPOSITIONS AND USES THEREOF

(71) Applicant: Lauren Sciences LLC, New York, NY (US)

(72) Inventors: Charles Linder, Rehovot (IL); Sarina Grinberg, Meitar (IL); Eliahu Heldman, Rehovot (IL)

(73) Assignee: Lauren Sciences LLC, New York, NY (US)

( * ) Notice: Subject to any disclaimer, the term of this patent is extended or adjusted under 35 U.S.C. 154(b) by 0 days.

(21) Appl. No.: 14/328,280

(22) Filed: Jul. 10, 2014

(65) Prior Publication Data

US 2015/0104502 A1    Apr. 16, 2015

Related U.S. Application Data

(63) Continuation-in-part of application No. PCT/US2013/057957, filed on Sep. 4, 2013.

(60) Provisional application No. 61/696,786, filed on Sep. 4, 2012, provisional application No. 61/844,782, filed on Jul. 10, 2013.

(51) Int. Cl.

| *A61K 31/675* | (2006.01) |
|---|---|
| *A61K 9/00* | (2006.01) |
| *A61K 9/107* | (2006.01) |
| *A61K 47/18* | (2017.01) |
| *A61K 47/34* | (2017.01) |
| *A61K 47/28* | (2006.01) |

(52) U.S. Cl.
CPC .......... *A61K 31/675* (2013.01); *A61K 9/0019* (2013.01); *A61K 9/1075* (2013.01); *A61K 47/18* (2013.01); *A61K 47/34* (2013.01); *A61K 47/28* (2013.01)

(58) Field of Classification Search
CPC ............................ A61K 9/1075; A61K 9/0019
See application file for complete search history.

(56) References Cited

FOREIGN PATENT DOCUMENTS

| WO | 2010/128504 A2 | 11/2010 |
| WO | 2010128504 A2 | 11/2010 |

OTHER PUBLICATIONS

Wolff, Manfred E. "Burger's Medicinal Chemistry, 5ed, Part I", John Wiley & Sons, 1995, pp. 975-977.*
Banker et al., "Modern Pharmaceutics, 3ed.", Marcel Dekker, New York, 1996, pp. 451 and 596.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Jordan, V. C. Nature Reviews: Drug Discovery, 2, 2003, pp. 205-213.*
http://www.merriamwebster.com /dictionary/derivative retrieved on Jan. 12, 2011.*
https://en.wikipedia.org/wiki/Metabolism, printed from WEB Mar. 21, 2019 (Year: 2019).*
Kwon, Younggil. Handbook of Essential Pharmacokinetics, Pharmacodynamics and Drug Metabolism for Industrial Scientists. Jun. 24, 2001. p. 213, paragraph 3 (Year: 2001).*
European Search Report, dated Apr. 18, 2016, for corresponding European Application No. 13835604.3.
Mary Popov, Sarina Grinberg, Charles Linder, Taj Waner, Boswat Levi-Hevroni, Richard J. Deckelbaum, Eliahu Heldman "Site-directed decapsultation of bolaamphiphilic vesicles with enzymatic cleavable surface groups," 2012, pp. 306-314.
Donatello Paolino, Donato Cosco, Rita Muzzalupo, Elena Trapasso, Nevio Picci, Massimo Fresta, "Innovative bola-surfactant niosomes as topical delivery systems of 5-fluorouracil for the treatment of skin skin cancer," International Journal of Pharmaceutics, 2008, pp. 233-242.
Chalon Sylvie et al., "Pharmacological Characterization of (E)-N-(4-Fluorobut-2-enyl)-2(3-carbomethoxy-3(3-K4'tolyl)nortropane (LBT-999) as a Highly Promising Fluorinated Ligand for the Dopamine Transporter". The Journal of Pharmacology and Experimental Therapeutics, 2006, pp. 147-152, p. 147, vol. 317, No. 1.
Puri Anu et al., "Lipid-Based Nanoparticles as Pharmaceutical Drug Carriers: From Concepts to Clinic", Crit Rev Ther Drug Carrier Syst., 2009, pp. 523-580, abstract, p. 4, paragraph 2, drawing 2, vol. 26, No. 6.
Branch III, Evans et al., "Tenovir: The First Nucleotide Analog for HIV-I." Drug Forecast, 2002, pp. 359-361 vol. 27, No. 7.
International Search Report with Written Opinion, dated Dec. 12, 2013, for corresponding international application PCT/US2013/057957.

* cited by examiner

*Primary Examiner* — James W Rogers
(74) *Attorney, Agent, or Firm* — Myers Wolin, LLC

(57) ABSTRACT

Bolaamphiphilic compounds are provided according to formula I:

$$HG^2\text{-}L^1\text{-}HG^1 \qquad \qquad I$$

where $HG^1$, $HG^2$ and $L^1$ are as defined herein. Provided bolaamphiphilic compounds and the pharmaceutical compositions thereof are useful for delivering HIV active drugs into animal or human brain.

5 Claims, 19 Drawing Sheets

BOLAAMPHIPHILIC COMPOUNDS, COMPOSITIONS AND USES THEREOF

CROSS REFERENCES TO RELATED APPLICATIONS

This is a continuation-in-part of International Application PCT/US13/57957, filed on Sep. 4, 2013, which claims priority to U.S. Patent Application 61/696,786, filed Sep. 2, 2012. This application also claims the benefit of U.S. Patent Application 61/844,782, filed on Jul. 10, 2013. The contents of each of the above-referenced applications are incorporated by reference herein.

FIELD

Provided herein are nanovesicles comprising bolaamphiphilic compounds, and complexes thereof with HIV drug molecules, and pharmaceutical compositions thereof. Also provided are methods of delivering HIV drug molecules into the human brain and animal brain using the compounds, complexes and pharmaceutical compositions provided herein.

BACKGROUND

Many AIDS patients, after receiving Highly Active Anti Retroviral Treatment (HAART), do not have detectable HIV in the blood, but they continue to have measurable amounts of HIV in the central nervous system (CNS). It is probable that this persistent HIV in the CNS (called, neuro-HIV) [Spudich and Antses, 2011] is a major obstacle in eradicating HIV in patients despite long-term HAART treatment [Gisslen et al, 2001; Highleyman, 2009, Varatharajan et al, 2009]. The incidence of HIV-associated dementia (HAD) has been reduced significantly with long-term HAART, but cognitive impairment is still measurable in as many as 50% of treated patients [Highleyman, 2009]. The reason for the cognitive impairment is, presumably, the persistence of HIV in the cerebrospinal fluid (CSF) of treated patients, despite suppression of the serum viral loads by HAART. Thus, it appears that the brain serves as a reservoir for persistent HIV, and that this reservoir prevents long-term HAART from curing HIV patients and alleviating cognitive malfunctions.

The brain is a highly specialized organ, and its sensitive components and functioning are protected by a barrier known as the blood-brain barrier (BBB). The brain capillary endothelial cells (BCECs) that form the BBB play important role in brain physiology by maintaining selective permeability and preventing passage of various compounds from the blood into the brain. One consequence of the highly effective barrier properties of the BBB is the limited penetration of therapeutic agents into the brain, which makes treatment of many brain diseases extremely challenging.

The persistence of the HIV virus in the CNS after HAART is thus, believed to be due to the inability of many of the HAART drugs to cross the blood brain barrier (BBB) (Varatharajan et al, 2009). To assess penetration of the HAART drugs into the brain, a scoring system has been developed, known as the CNS penetration effectiveness (CPE) index, which ranks antiretroviral drugs' ability to enter the brain [Letendre et al, 2008].

Efforts to improve the permeation of HIV drugs across the BBB have been attempted, but have not proven therapeutically successful. For example, the oldest antiretroviral drug, AZT, was encapsulated in a magnetized liposome to help it cross the BBB, but that delivery system did not provide sufficient improvement in bioavailability to be used therapeutically [Saiyed et al, 2010].

Some of the most widely used and effective (in terms of reducing HIV load in the circulation) antiretroviral drugs have the lowest (worst) CPE rating. For example, tenofovir, a component of the combination pills Truvad and Atripla, is widely used in HAART, but it hardly crosses the BBB, if at all (CPE rating of 1).

Efforts to improve the permeation of biologically active compounds across the BBB using amphiphilic vesicles have been attempted.

For example, complexation of the anionic carboxyfluorescein (CF) (a fluorescent marker) with single headed amphiphiles of opposite charge in cationic vesicles, formed by mixing single-tailed cationic and anionic surfactants has been reported (Danoff et al. 2007). In addition to complexation a certain portion of the CF is passively encapsulated within the core of the formed vesicles. And our present invention using bolaamphiphiles includes the embodiments wherein a portion of the active agent may be complexed to the head groups of the bolaamphiphiles and another fraction of the active agents are encapsulated within the core of the vesicles. In many embodiments the major portion of the active agent is encapsulated by complexation with the head groups.

Furthermore, WO 02/055011 and WO 03/047499, both of the same applicant of the present invention, disclose amphiphilic derivatives composed of at least one fatty acid chain derived from natural vegetable oils such as vernonia oil, *lesquerella* oil and castor oil, in which functional groups such as epoxy, hydroxy and double bonds were modified into polar and ionic headgroups.

Additionally, WO 10/128504 reports a series of amphiphiles and bolamphiphiles (amphiphiles with two head groups) useful for targeted drug delivery of insulin, insulin analogs, TNF, GDNF, DNA, RNA (including siRNA), enkephalin class of analgesics, and others.

These synthetic bolaamphiphiles (bolas) have recently been shown to form nanovesicles that interact with and encapsulate a variety of small and large molecules including peptides, proteins and plasmid DNAs delivering them across biological membranes. These bolaamphiphiles are a unique class of compounds that have two hydrophilic headgroups placed at each ends of a hydrophobic domain. Bolaamphiphiles can form vesicles that consist of monolayer membrane that surrounds an aqueous core. Vesicles made from natural bolaamphiphiles, such as those extracted from archaebacteria (archaesomes), are very stable and, therefore, might be employed for targeted drug delivery. However, bolaamphiphiles from archaebacteria are heterogeneous and cannot be easily extracted or chemically synthesized.

There are however no efficient delivery systems for delivery of effective HIV drugs into the CNS after systemic administration. Thus, there remains a need to make new compositions and for novel methods to deliver HIV active drugs into the brain. The compounds, compositions, and methods described herein are directed toward this end.

SUMMARY OF THE INVENTION

In certain aspects, provided herein are pharmaceutical compositions comprising of a bolaamphiphile complex.

In further aspects, provided herein are novel nano-sized vesicles comprising of bolaamphiphilic compounds.

In certain aspects, provided herein are novel bolaamphiphile complexes comprising one or more bolaamphiphilic compounds and a compound active against HIV.

In further aspects, provided herein are novel formulations of HIV active compounds with one or more bolaamphiphilic compounds or with bolaamphiphile vesicles. In a further aspect there are submicron vesicles with a monolayer membrane or bilayer membrane encapsulating an inner core, with an HIV active compound encapsulated within its core and/or complexed to the inner and our head groups of the bolaamphiphile which comprise the said membrane.

In another aspect, provided here are methods of delivering HIV active drugs agents into animal or human brain. In one embodiment, the method comprises the step of administering to the animal or human a pharmaceutical composition comprising of a bolaamphiphile complex; and wherein the bolaamphiphile complex comprises one or more bolaamphiphilic compounds and a compound active against HIV. In one particular embodiment, the HIV active drug is Tenofovir or ({[(2R)-1-(6-amino-9H-purin-9-yl)propan-2-yl]oxy}methyl)phosphonic acid. In another particular embodiment, the HIV active drug is fosamprenavir. In another particular embodiment, the HIV active drug is enfuvirtide. In another particular embodiment, the HIV active drug is saquinavir. In another particular embodiment, the HIV active drug is lamivudine. In another particular embodiment, the HIV active drug is stavudine. In one important embodiment the said bolaamphiphiles of the said bolaamphiphilic complex comprises an aggregate which is a submicron vesicles wherein the said bolaamphiphiles comprise the membrane of the aggregate which encapsulate an inner core.

In one embodiment, the bolaamphiphilic compound consists of two hydrophilic headgroups linked through a long hydrophobic chain. In another embodiment, the hydrophilic headgroup is an amino containing group. In a specific embodiment, the hydrophilic headgroup is a tertiary or quaternary amino containing group.

In one particular embodiment, the bolaamphiphilic compound is a compound according to formula I:

$$HG^2-L^1-HG^1 \quad I$$

or a pharmaceutically acceptable salt, solvate, hydrate, prodrug, stereoisomer, tautomer, isotopic variant, or N-oxide thereof, or a combination thereof;
wherein:
each $HG^1$ and $HG^2$ is independently a hydrophilic head group; and
$L^1$ is alkylene, alkenyl, heteroalkylene, or heteroalkenyl linker; unsubstituted or substituted with $C_1$-$C_{20}$ alkyl, hydroxyl, or oxo.

In one embodiment, the pharmaceutically acceptable salt is a quaternary ammonium salt.

In one embodiment, with respect to the bolaamphiphilic compound of formula I, the bolaamphiphilic compound is a compound according to formula II, III, IV, V, or VI:

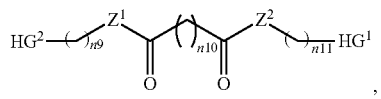

II

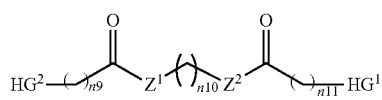

III

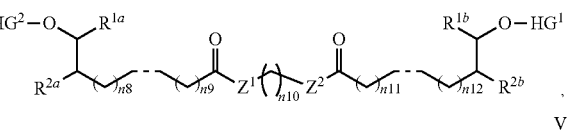

IV

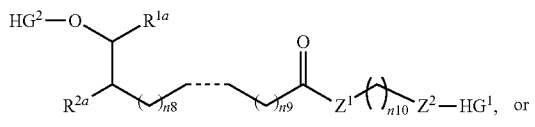

V

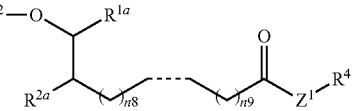

VI or a pharmaceutically acceptable salt, solvate, hydrate, prodrug, stereoisomer, tautomer, isotopic variant, or N-oxide thereof, or a combination thereof;
wherein:
each $HG^1$ and $HG^2$ is independently a hydrophilic head group;
each $Z^1$ and $Z^2$ is independently $-C(R^3)_2-$, $-N(R^3)-$ or $-O-$;
$R^{1a}$, $R^{1b}$, $R^3$, and $R^4$ is independently H or $C_1$-$C_8$ alkyl;
each $R^{2a}$ and $R^{2b}$ is independently H, $C_1$-$C_8$ alkyl, OH, alkoxy, or O-$HG^1$ or O-$HG^2$;
each n8, n9, n11, and n12 is independently an integer from 1-20;
n10 is an integer from 2-20; and
each dotted bond is independently a single or a double bond.

In one embodiment, with respect to the bolaamphiphilic compound of formula I, II, III, IV, V, or VI, each $HG^1$ and $HG^2$ is independently selected from:

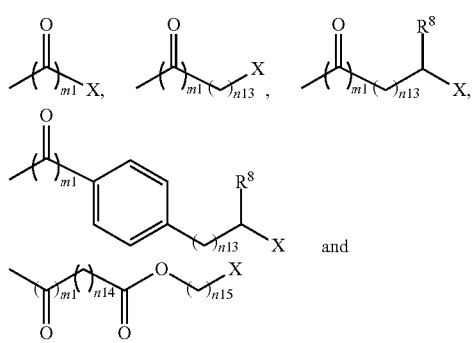

wherein:
X is $-NR^{5a}R^{5b}$, or $-N^+R^{5a}R^{5b}R^{5c}$; each $R^{5a}$, and $R^{5b}$ is independently H or substituted or unsubstituted $C_1$-$C_{20}$ alkyl or $R^{5a}$ and $R^{5b}$ may join together to form an N containing substituted or unsubstituted heteroaryl, or substituted or unsubstituted heterocyclyl;
each $R^{5c}$ is independently substituted or unsubstituted $C_1$-$C_{20}$ alkyl; each $R^8$ is independently H, substituted or unsubstituted $C_1$-$C_{20}$ alkyl, alkoxy, or carboxy;
m1 is 0 or 1; and
each n13, n14, and n15 is independently an integer from 1-20.

In certain embodiments, vesicle formation is carried out in the presence of an additive that increases encapsulation of a therapeutic agent. In one aspect of this embodiment, the additive is stearyl amine. In another aspect, the therapeutic agent is an antiviral agent, while in a still further aspect the antiviral agent is Tenofovir. In still another aspect the vesicles formed from the bolaamphiphiles contain additives that help to stabilize the vesicles, by stabilizing the vesicle's membranes, such as but not limited to cholesterol derivcatives such as cholesteryl hemisuccinate and cholesterol itself and combinations such as cholesteryl hemisuccinate and cholesterol. In another embodiment the vesicles comprise the bolaamphiphiles, vesicle membrane stabilizing additives, stearyl amine, and tenofovir. In still another embodiments the vesicles in addition to these components have another additives which decorates the outer vesicle membranes with groups or pendants that enhance penetration though biological barriers such as the BBB. A none limiting example of such additives may be alkyl conjugates of chitosan or bolaamphiphiles where one of the head groups is chitosan.

In certain embodiments, the present disclosure is directed to a method of treatment of a patient afflicted with a viral disease comprising administration of vesicles described herein. In one aspect of this embodiment, the patient is a human AIDS patient in need of such treatment. In particular aspects of this embodiment, the vesicles are formed in the presence of an additive that increases encapsulation of a therapeutic agent. In one aspect of this embodiment, the additive is stearyl amine. In another aspect, the therapeutic agent is an antiviral agent, while in a still further aspect the antiviral agent is Tenofovir. In another aspect of this embodiment, the virus is HIV.

Other objects and advantages will become apparent to those skilled in the art from a consideration of the ensuing detailed description.

DEFINITIONS

Chemical Definitions

Figure 1A:
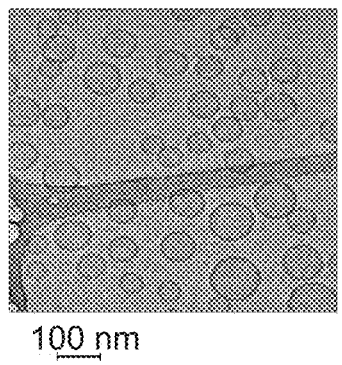
FIG. 1A: TEM micrograph of vesicles from GLH-20 FIG. 1B size distribution of vesicles from GLH-20 determined by DLS.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-2}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_{1-12}$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_2$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., $CH_3$). In certain embodiments, the alkyl group is substituted $C_{1-10}$ alkyl.

"Alkylene" refers to a substituted or unsubstituted alkyl group, as defined above, wherein two hydrogens are removed to provide a divalent radical. Exemplary divalent alkylene groups include, but are not limited to, methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers a substituted or unsubstituted alkenyl group, as defined above, wherein two hydrogens are removed to provide a divalent radical. Exemplary divalent alkenylene groups include, but are not limited to, ethenylene (—CH=CH—), propenylenes (e.g., —CH=$CHCH_2$— and —$C(CH_3)$=CH— and —CH=$C(CH_3)$—) and the like.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers a substituted or unsubstituted alkynyl group, as defined above, wherein two hydrogens are removed to provide a divalent radical. Exemplary divalent alkynylene groups include, but are not limited to, ethynylene, propynylene, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

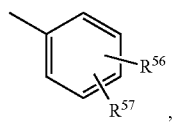 , 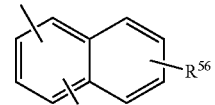 and

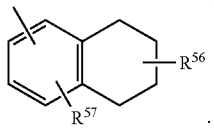

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl ring or with an aliphatic ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

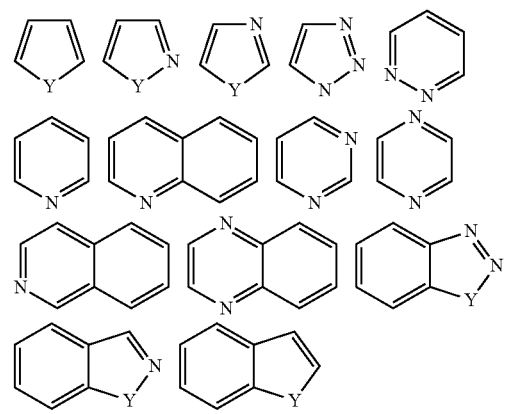

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

Examples of representative aryl having hetero atoms containing substitution include the following:

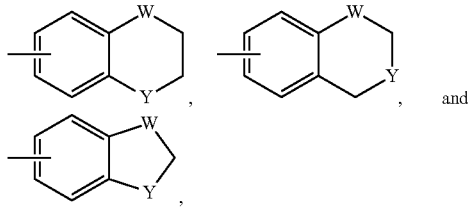

wherein each W is selected from C(R$^{66}$)$_2$, NR$^{66}$, O, and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a nonaromatic cyclic hydrocarbon group having from 3 to 10 ring carbon atoms ("C$_{3-10}$ carbocyclyl") and zero heteroatoms in the nonaromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3 to 10-membered non aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

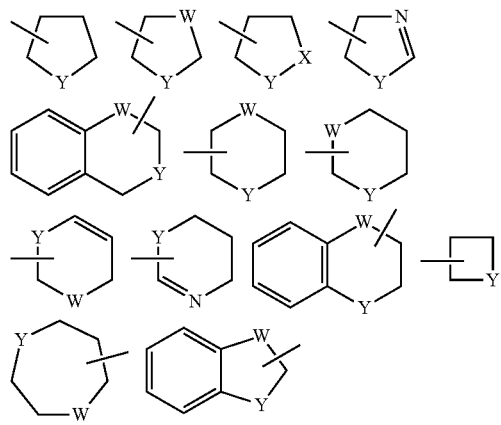

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more substituents selected from the group consisting of the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —NR$^{22}$C(O)R$^{23}$, where each instance of $R^{22}$ and R23 is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—C$_1$-C$_8$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)—(CH$_2$)$_t$(C$_3$-C$_{10}$ cycloalkyl), and —NR$^{24}$C(O)—(CH$_2$)$_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided that at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance, from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from: hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary 'substituted amino' groups are —N$R^{39}$—$C_1$-$C_8$ alkyl, —N$R^{39}$—(CH$_2$)$_t$($C_6$-$C_{10}$ aryl), —N$R^{39}$—(CH$_2$)$_t$(5-10 membered heteroaryl), —N$R^{39}$—(CH$_2$)$_t$($C_3$-$C_{10}$ cycloalkyl), and —N$R^{39}$—(CH$_2$)$_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted haloalkoxy or hydroxy; provided that at least one $R^{62}$ is other than H.

Exemplary 'substituted carbamoyl' groups include, but are not limited to, —C(O) N$R^{64}$—$C_1$-$C_8$ alkyl, —C(O)N$R^{64}$—(CH$_2$)$_t$($C_6$-$C_{10}$ aryl), —C(O)N$R^{64}$—(CH$_2$)$_t$(5-10 membered heteroaryl), —C(O)N$R^{64}$—(CH$_2$)$_t$($C_3$-$C_{10}$ cycloalkyl), and —C(O)N$R^{64}$—(CH$_2$)$_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted haloalkoxy or hydroxy.

'Carboxy' refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro. In further embodiments, the halo group is iodo.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C═C)—.

"Ethylene" refers to substituted or unsubstituted —(C—C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group ═S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(═O)$R^{aa}$, —$CO_2H$, —CHO, —C(O$R^{cc}$)$_2$, —$CO_2R^{aa}$, —OC(═O)$R^{aa}$, —$OCO_2R^{aa}$, —C(═O)N($R^{bb}$)$_2$, —OC(═O)N($R^{bb}$)$_2$, —$NR^{bb}$C(═O)$R^{aa}$, —$NR^{bb}CO_2R^{aa}$, —$NR^{bb}$C(═O)N($R^{bb}$)$_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)N($R^{bb}$)$_2$, —OC(═$NR^{bb}$)N($R^{bb}$)$_2$, —$NR^{bb}$C(═$NR^{bb}$)N($R^{bb}$)$_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —Si($R^{bb}$)$_3$, —OSi($R^{aa}$)$_3$ —C(═S)N($R^{bb}$)$_2$, —C(═O)$SR^{aa}$, —C(═S)$SR^{aa}$, —SC(═S) $SR^{aa}$, —SC(═O)$SR^{aa}$, —OC(═O)$SR^{aa}$, —SC(═O)$OR^{aa}$, —SC(═O)$R^{aa}$, —P(═O)$_2R^{aa}$, —OP(═O)$_2R^{aa}$, —P(═O) ($R^{aa}$)$_2$, —OP(═O)($R^{aa}$)$_2$, —OP(═O)($OR^{cc}$)$_2$, —P(═O)$_2$N ($R^{bb}$)$_2$, —OP(═O)$_2$N($R^{bb}$)$_2$, —P(═O)(N$R^{bb}$)$_2$, —OP(═O) (N$R^{bb}$)$_2$, —$NR^{bb}$P(═O)($OR^{cc}$)$_2$, —$NR^{bb}$P(═O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B($OR^{cc}$)$_2$, —B$R^{aa}$($OR^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group ═O, ═S, ═NN($R^{bb}$)$_2$, ═$NNR^{bb}$C(═O) $R^{aa}$, ═$NNR^{bb}$C(═O)$OR^{aa}$, ═$NNR^{bb}$, or ═$NOR^{cc}$; each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{bb}$ is, independently, selected from hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{cc}$)$OR^{aa}$, —C(═$NR^{cc}$)N ($R^{cc}$)$_2$, —$SO_2N(R^{cc})_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)$_2R^{aa}$, —P(═O)($R^{aa}$)$_2$, —P(═O)$_2$N($R^{cc}$)$_2$, —P(═O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —OC$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-16}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DBtBOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1 isopropylallyl carbamate (Ipaoc), cinnamyl carbamate (Coc), 4-nitrocinnamyl carbamate (Noc), 8-quinolyl carbamate, N hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, mchloropacyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilyletbanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl (10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(═O)SR$^{aa}$, —C(═O)R$^{aa}$, —CO$_2$R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$) N(R$^{bb}$)$_2$, —S(═O)R$^{aa}$, —SO$_2$R$^{aa}$, —Si(R$^{aa}$)$_3$, —P(R$^{cc}$)$_2$, —P(R$^{cc}$)$_3$, —P(═O)$_2$R$^{aa}$, —P(═O)(R$^{aa}$)$_2$, —P(═O) (OR$^{cc}$)$_2$, —P(═O)$_2$N(R$^{bb}$)$_2$, and —P(═O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, pchlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

"Compounds of the present invention", and equivalent expressions, are meant to embrace the compounds as hereinbefore described, in particular compounds according to any of the Formula herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

These and other exemplary substituents are described in more detail in the Detailed Description, Examples, and claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like (see, e.g., Berge, et al., *J. Pharm. Sci.* 66(1): 1-79 (January'77).

"Pharmaceutically acceptable vehicle" refers to a diluent, adjuvant, excipient or carrier with which a compound of the invention is administered.

"Pharmaceutically acceptable metabolically cleavable group" refers to a group which is cleaved in vivo to yield the parent molecule of the structural Formula indicated herein. Examples of metabolically cleavable groups include —COR, —COOR, —CONRR and —$CH_2OR$ radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention, which have cleavable groups and become by solvolysis or under physiological conditions the compounds of the invention that are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human", "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Preventing" or "prevention" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Treating" or "treatment" of any disease or disorder refers, in certain embodiments, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3H$, and carbon-14, i.e., $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of r electrons and an atom (usually H). For example, enols and ketones are tautomers because they are rapidly interconverted by treatment with either acid or base. Another example of tautomerism is the aci- and nitro-forms of phenylnitromethane, which are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION OF THE PREFERRED EMBODIMENTS

In certain aspects, provided herein are pharmaceutical compositions comprising of a bolaamphiphile complex.

In further aspects, provided herein are novel nano-sized vesicles comprising of bolaamphiphilic compounds.

In certain aspects, provided herein are novel bolaamphiphile complexes comprising one or more bolaamphiphilic compounds and a compound active against HIV.

In further aspects, provided herein are novel formulations of HIV active compounds with one or more bolaamphiphilic compounds or with bolaamphiphile vesicles.

In another aspect, provided here are methods of delivering HIV active drugs agents into animal or human brain. In one embodiment, the method comprises the step of administering to the animal or human a pharmaceutical composition comprising of a bolaamphiphile complex; and wherein the bolaamphiphile complex comprises one or more bolaamphiphilic compounds and a compound active against HIV. In one particular embodiment, the HIV active drug is Tenofovir or ({[(2R)-1-(6-amino-9H-purin-9-yl)propan-2-yl]oxy}methyl)phosphonic acid. In another particular embodiment, the HIV active drug is fosamprenavir. In another particular embodiment, the HIV active drug is enfuvirtide. In another particular embodiment, the HIV active drug is saquinavir. In another particular embodiment, the HIV active drug is lamivudine. In another particular embodiment, the HIV active drug is stavudine.

In one embodiment, the bolaamphiphilic complex comprises one bolaamphiphilic compound. In another embodiment, the bolaamphiphilic complex comprises two bolaamphiphilic compounds.

In one embodiment, the bolaamphiphilic compound consists of two hydrophilic headgroups linked through a long hydrophobic chain. In another embodiment, the hydrophilic headgroup is an amino containing group. In a specific embodiment, the hydrophilic headgroup is a tertiary or quaternary amino containing group.

In one particular embodiment, the bolaamphiphilic compound is a compound according to formula I:

$$HG^2\text{-}L^1\text{-}HG^1 \qquad \qquad I$$

or a pharmaceutically acceptable salt, solvate, hydrate, prodrug, stereoisomer, tautomer, isotopic variant, or N-oxide thereof, or a combination thereof;

wherein:
each $HG^1$ and $HG^2$ is independently a hydrophilic head group; and
$L^1$ is alkylene, alkenyl, heteroalkylene, or heteroalkenyl linker; unsubstituted or substituted with $C_1$-$C_{20}$ alkyl, hydroxyl, or oxo.

In one embodiment, the pharmaceutically acceptable salt is a quaternary ammonium salt.

In one embodiment, with respect to the bolaamphiphilic compound of formula I, $L^1$ is heteroalkylene, or heteroalkenyl linker comprising C, N, and O atoms; unsubstituted or substituted with $C_1$-$C_{20}$ alkyl, hydroxyl, or oxo.

In another embodiment, with respect to the bolaamphiphilic compound of formula I, $L^1$ is —O-$L^2$-C(O)—O—(CH$_2$)$_{n4}$—O—C(O)-$L^3$-O—, or —O-$L^2$C(O)—O—(CH$_2$)$_{n5}$—O—C(O)—(CH$_2$)$_{n6}$—, and wherein each $L^2$ and $L^3$ is $C_4$-$C_{20}$ alkenyl linker; unsubstituted or substituted with $C_1$-$C_8$ alkyl or hydroxy;

and n4, n5, and n6 is independently an integer from 4-20.

In one embodiment, each $L^2$ and $L^3$ is independently C(R$^1$)—C(OH)—CH$_2$—(CH═CH)—(CH$_2$)$_{n7}$—; R$^1$ is $C_1$-$C_8$ alkyl, and n7 is independently an integer from 4-20.

In another embodiment, with respect to the bolaamphiphilic compound of formula I, $L^1$ is —O—(CH$_2$)$_{n1}$—O—C(O)—(CH$_2$)$_{n2}$—C(O)—O—(CH$_2$)$_{n3}$—O—.

In another embodiment, with respect to the bolaamphiphilic compound of formula I, $L^1$ is

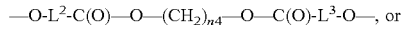
Linker AA

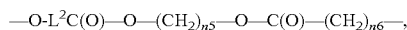
Linker BB

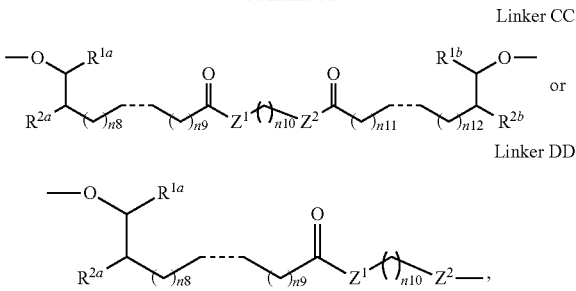
Linker CC

Linker DD wherein:
each $Z^1$ and $Z^2$ is independently —C(R$^3$)$_2$—, —N(R$^3$)— or —O—;
each $R^{1a}$, $R^{1b}$, $R^3$, and $R^4$ is independently H or $C_1$-$C_8$ alkyl;
each $R^{2a}$ and $R^{2b}$ is independently H, $C_1$-$C_8$ alkyl, OH, or alkoxy;
each n8, n9, n11, and n12 is independently an integer from 1-20;
n10 is an integer from 2-20; and
each dotted bond is independently a single or a double bond.
and wherein each methylene carbon is unsubstituted or substituted with $C_1$-$C_4$ alkyl; and each n1, n2, and n3 is independently an integer from 4-20.

In one embodiment, with respect to the bolaamphiphilic compound of formula I, the bolaamphiphilic compound is a compound according to formula II, III, IV, V, or VI:

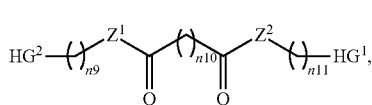
II

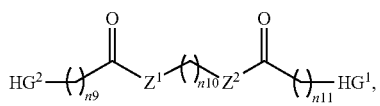
III

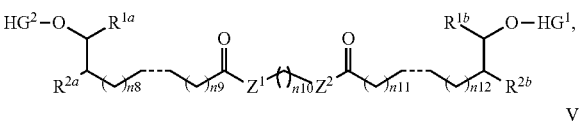
IV

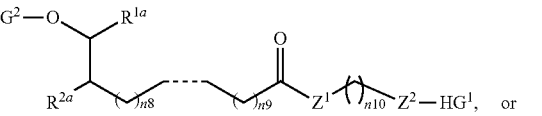
V

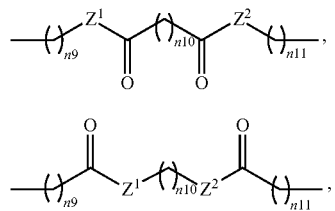
VI or a pharmaceutically acceptable salt, solvate, hydrate, prodrug, stereoisomer, tautomer, isotopic variant, or N-oxide thereof, or a combination thereof;
wherein:
each $HG^1$ and $HG^2$ is independently a hydrophilic head group;
each $Z^1$ and $Z^2$ is independently —C(R$^3$)$_2$—, —N(R$^3$)— or —O—;

each $R^{1a}$, $R^{1b}$, $R^3$, and $R^4$ is independently H or $C_1$-$C_8$ alkyl;

each $R^{2a}$ and $R^{2b}$ is independently H, $C_1$-$C_8$ alkyl, OH, alkoxy, or O-$HG^1$ or O-$HG^2$;

each n8, n9, n11, and n12 is independently an integer from 1-20;

n10 is an integer from 2-20; and each dotted bond is independently a single or a double bond.

In one embodiment, with respect to the bolaamphiphilic compound of formula II, III, IV, V, or VI, each n9 and n11 is independently an integer from 2-12. In another embodiment, n9 and n11 is independently an integer from 4-8. In a particular embodiment, each n9 and n11 is 7 or 11.

In one embodiment, with respect to the bolaamphiphilic compound of formula II, III, IV, V, or VI, each n8 and n12 is independently 1, 2, 3, or 4. In a particular embodiment, each n8 and n12 is 1.

In one embodiment, with respect to the bolaamphiphilic compound of formula II, III, IV, V, or VI, each $R^{2a}$ and $R^{2b}$ is independently H, OH, or alkoxy. In another embodiment, each $R^{2a}$ and $R^{2b}$ is independently H, OH, or OMe. In another embodiment, each $R^{2a}$ and $R^{2b}$ is independently -O-$HG^1$ or O-$HG^2$. In a particular embodiment, each $R^{2a}$ and $R^{2b}$ is OH.

In one embodiment, with respect to the bolaamphiphilic compound of formula II, III, IV, V, or VI, each $R^{1a}$ and $R^{1b}$ is independently H, Me, Et, n-Pr, i-Pr, n-Bu, i-Bu, sec-Bu, n-pentyl, isopentyl, n-hexyl, n-heptyl, or n-octyl. In a particular embodiment, each $R^{1a}$ and $R^{1b}$ is independently n-pentyl.

In one embodiment, with respect to the bolaamphiphilic compound of formula II, III, IV, V, or VI, each dotted bond is a single bond. In another embodiment, each dotted bond is a double bond.

In one embodiment, with respect to the bolaamphiphilic compound of formula II, III, IV, V, or VI, n10 is an integer from 2-16. In another embodiment, n10 is an integer from 2-12. In a particular embodiment, n10 is 2, 4, 6, 8, 10, 12, or 16.

In one embodiment, with respect to the bolaamphiphilic compound of formula IV, $R^4$ is H, Me, Et, n-Pr, i-Pr, n-Bu, i-Bu, sec-Bu, n-pentyl, or isopentyl. In another embodiment, $R^4$ is Me, or Et. In a particular embodiment, $R^4$ is Me.

In one embodiment, with respect to the bolaamphiphilic compound of formula II, III, IV, V, or VI, each $Z^1$ and $Z^2$ is independently $C(R^3)_2$—, or —$N(R^3)$—. In another embodiment, each $Z^1$ and $Z^2$ is independently $C(R^3)_2$—, or —$N(R^3)$—; and each $R^3$ is independently H, Me, Et, n-Pr, i-Pr, n-Bu, i-Bu, sec-Bu, n-pentyl, or isopentyl. In a particular embodiment, $R^3$ is H.

In one embodiment, with respect to the bolaamphiphilic compound of formula II, III, IV, V, or VI, each $Z^1$ and $Z^2$ is —O—.

In one embodiment, with respect to the bolaamphiphilic compound of formula I, II, III, or IV, each $HG^1$ and $HG^2$ is independently selected from:

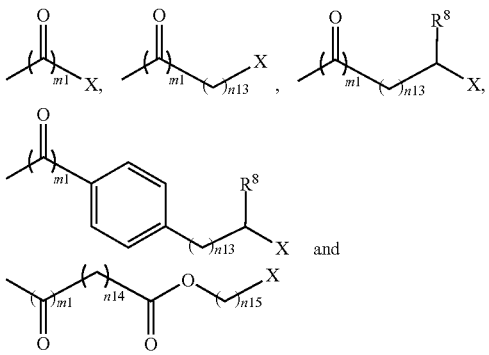

wherein:
X is —$NR^{5a}R^{5b}$, or —$N^+R^{5a}R^{5b}R^{5c}$; each $R^{5a}$, and $R^{5b}$ is independently H or substituted or unsubstituted $C_1$-$C_{20}$ alkyl or $R^{5a}$ and $R^{5b}$ may join together to form an N containing substituted or unsubstituted heteroaryl, or substituted or unsubstituted heterocyclyl;

each $R^{5c}$ is independently substituted or unsubstituted $C_1$-$C_{20}$ alkyl; each $R^8$ is independently H, substituted or unsubstituted $C_1$-$C_{20}$ alkyl, alkoxy, or carboxy;

m1 is 0 or 1; and each n13, n14, and n15 is independently an integer from 1-20.

In one embodiment, with respect to the bolaamphiphilic compound of formula I, II, III, or IV, $HG^1$ and $HG^2$ are as defined above, and each m1 is 0.

In one embodiment, with respect to the bolaamphiphilic compound of formula I, II, III, or IV, $HG^1$ and $HG^2$ are as defined above, and each m1 is 1.

In one embodiment, with respect to the bolaamphiphilic compound of formula I, II, III, or IV, $HG^1$ and $HG^2$ are as defined above, and each n13 is 1 or 2.

In one embodiment, with respect to the bolaamphiphilic compound of formula I, II, III, or IV, $HG^1$ and $HG^2$ are as defined above, and each n14 and n15 is independently 1, 2, 3, 4, or 5. In another embodiment, each n14 and n15 is independently 2 or 3.

In one particular embodiment, the bolaamphiphilic compound is a compound according to formula VIIa, VIIb, VIIc, or VIId:

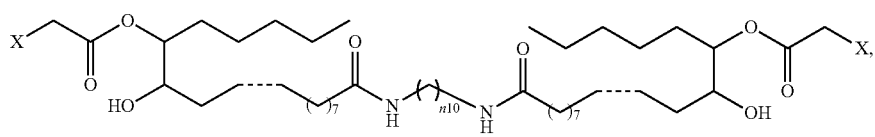

VIIa

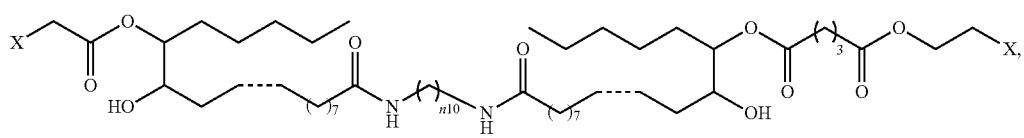

VIIb

VIIc

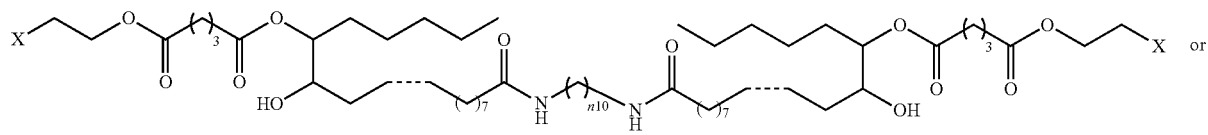

VIId

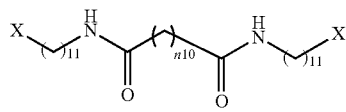

or a pharmaceutically acceptable salt, solvate, hydrate, prodrug, stereoisomer, tautomer, isotopic variant, or N-oxide thereof, or a combination thereof;
wherein:
  each X is $-NR^{5a}R^{5b}$, or $-N^+R^{5a}R^{5b}R^{5c}$; each $R^{5a}$, and $R^{5b}$ is independently H or substituted or unsubstituted $C_1$-$C_{20}$ alkyl or $R^{5a}$ and $R^{5b}$ may join together to form an N containing substituted or unsubstituted heteroaryl, or substituted or unsubstituted heterocyclyl;
  each $R^{5c}$ is independently substituted or unsubstituted $C_1$-$C_{20}$ alkyl;
  n10 is an integer from 2-20; and
  each dotted bond is independently a single or a double bond.

In another particular embodiment, the bolaamphiphilic compound is a compound according to formula VIIIa, VIIIb, VIIIc, or VIIId:

or a pharmaceutically acceptable salt, solvate, hydrate, prodrug, stereoisomer, tautomer, isotopic variant, or N-oxide thereof, or a combination thereof;
wherein:
  each X is $-NR^{5a}R^{5b}$, or $-N^+R^{5a}R^{5b}R^{5c}$; each $R^{5a}$, and $R^{5b}$ is independently H or substituted or unsubstituted $C_1$-$C_{20}$ alkyl or $R^{5a}$ and $R^{5b}$ may join together to form an N containing substituted or unsubstituted heteroaryl, or substituted or unsubstituted heterocyclyl;
  each $R^{5c}$ is independently substituted or unsubstituted $C_1$-$C_{20}$ alkyl;
  n10 is an integer from 2-20; and
  each dotted bond is independently a single or a double bond.

In another particular embodiment, the bolaamphiphilic compound is a compound according to formula IXa, IXb, or IXc:

VIIIa

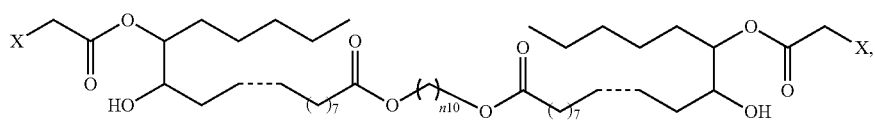

VIIIb

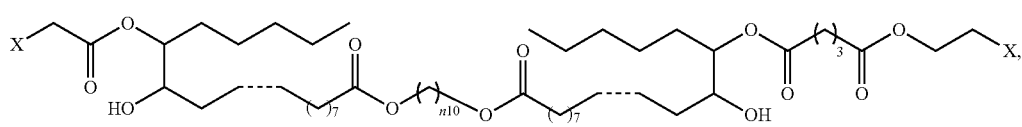

VIIIc

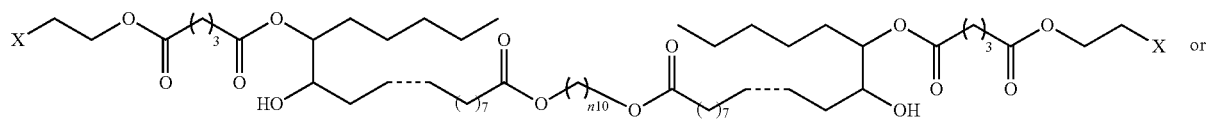

VIIId

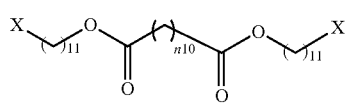

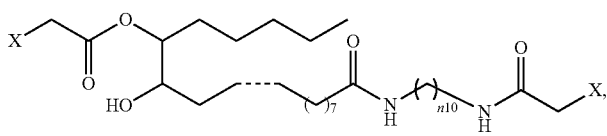

IXa

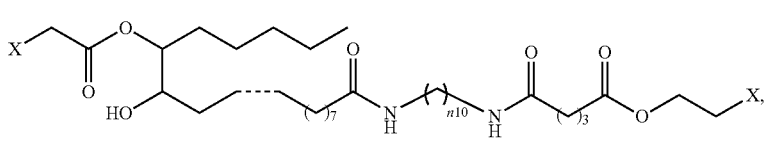

IXb

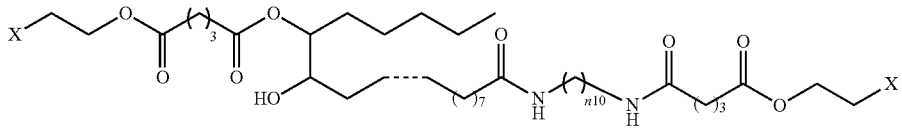

IXc or a pharmaceutically acceptable salt, solvate, hydrate, prodrug, stereoisomer, tautomer, isotopic variant, or N-oxide thereof, or a combination thereof;
wherein:
each X is —NR$^{5a}$R$^{5b}$, or —N$^+$R$^{5a}$R$^{5b}$R$^{5c}$; each R$^{5a}$, and R$^{5b}$ is independently H or substituted or unsubstituted C$_1$-C$_{20}$ alkyl or R$^{5a}$ and R$^{5b}$ may join together to form an N containing substituted or unsubstituted heteroaryl, or substituted or unsubstituted heterocyclyl;
each R$^{5c}$ is independently substituted or unsubstituted C$_1$-C$_{20}$ alkyl;
n10 is an integer from 2-20; and
each dotted bond is independently a single or a double bond.

In another particular embodiment, the bolaamphiphilic compound is a compound according to formula Xa, Xb, or Xc:

n10 is an integer from 2-20; and
each dotted bond is independently a single or a double bond.

In one embodiment, with respect to the bolaamphiphilic compound of formula VIIa-VIId, VIIIa-VIIId, IXa-IXc, or Xa-Xc, each dotted bond is a single bond. In another embodiment, each dotted bond is a double bond.

In one embodiment, with respect to the bolaamphiphilic compound of formula VIIa-VIId, VIIIa-VIIId, IXa-IXc, or Xa-Xc, n10 is an integer from 2-16.

In one embodiment, with respect to the bolaamphiphilic compound of formula VIIa-VIId, VIIIa-VIIId, IXa-IXc, or Xa-Xc, n10 is an integer from 2-12.

In one embodiment, with respect to the bolaamphiphilic compound of formula VIIa-VIId, VIIIa-VIIId, IXa-IXc, or Xa-Xc, n10 is 2, 4, 6, 8, 10, 12, or 16.

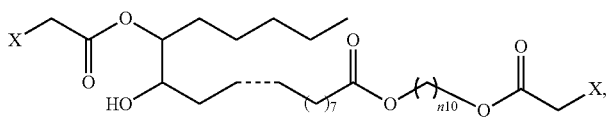

Xa

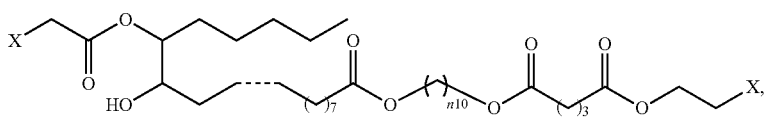

Xb

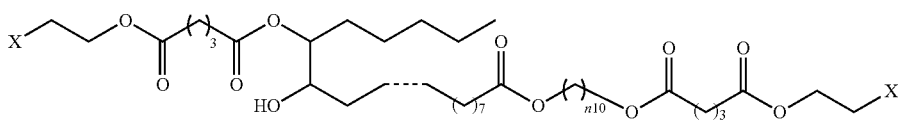

Xc or a pharmaceutically acceptable salt, solvate, hydrate, prodrug, stereoisomer, tautomer, isotopic variant, or N-oxide thereof, or a combination thereof;
wherein:
each X is —NR$^{5a}$R$^{5b}$, or —N$^+$R$^{5a}$R$^{5b}$R$^{5c}$; each R$^{5a}$, and R$^{5b}$ is independently H or substituted or unsubstituted C$_1$-C$_{20}$ alkyl or R$^{5a}$ and R$^{5b}$ may join together to form an N containing substituted or unsubstituted heteroaryl, or substituted or unsubstituted heterocyclyl;
each R$^{5c}$ is independently substituted or unsubstituted C$_1$-C$_{20}$ alkyl;

In one embodiment, with respect to the bolaamphiphilic compound of formula VIIa-VIId, VIIIa-VIIId, IXa-IXc, or Xa-Xc, each R$^{5a}$, R$^{5b}$, and R$^{5c}$ is independently substituted or unsubstituted C$_1$-C$_{20}$ alkyl.

In one embodiment, with respect to the bolaamphiphilic compound of formula VIIa-VIId, VIIIa-VIIId, IXa-IXc, or Xa-Xc, each R$^{5a}$, R$^{5b}$, and R$^{5c}$ is independently unsubstituted C$_1$-C$_{20}$ alkyl.

In one embodiment, with respect to the bolaamphiphilic compound of formula VIIa-VIId, VIIIa-VIIId, IXa-IXc, or Xa-Xc, one of $R^{5a}$, $R^{5b}$, and $R^{5c}$ is $C_1$-$C_{20}$ alkyl substituted with —OC(O)$R^6$; and $R^6$ is $C_1$-$C_{20}$ alkyl.

In one embodiment, with respect to the bolaamphiphilic compound of formula VIIa-VIId, VIIIa-VIIId, IXa-IXc, or Xa-Xc, two of $R^{5a}$, $R^{5b}$, and $R^{5c}$ are independently $C_1$-$C_{20}$ alkyl substituted with —OC(O)$R^6$; and $R^6$ is $C_1$-$C_{20}$ alkyl. In one embodiment, $R^6$ is Me, Et, n-Pr, i-Pr, n-Bu, i-Bu, sec-Bu, n-pentyl, isopentyl, n-hexyl, n-heptyl, or n-octyl. In a particular embodiment, $R^6$ is Me.

In one embodiment, with respect to the bolaamphiphilic compound of formula VIIa-VIId, VIIIa-VIIId, IXa-IXc, or Xa-Xc, one of $R^{5a}$, $R^{5b}$, and $R^{5c}$ is $C_1$-$C_{20}$ alkyl substituted with amino, alkylamino or dialkylamino.

In one embodiment, with respect to the bolaamphiphilic compound of formula VIIa-VIId, VIIIa-VIIId, IXa-IXc, or Xa-Xc, two of $R^{5a}$, $R^{5b}$, and $R^{5c}$ are independently $C_1$-$C_{20}$ alkyl substituted with amino, alkylamino or dialkylamino.

In one embodiment, with respect to the bolaamphiphilic compound of formula VIIa-VIId, VIIIa-VIIId, IXa-IXc, or Xa-Xc, $R^{5a}$, and $R^{5b}$ together with the N they are attached to form substituted or unsubstituted heteroaryl.

In one embodiment, with respect to the bolaamphiphilic compound of formula VIIa-VIId, VIIIa-VIIId, IXa-IXc, or Xa-Xc, $R^{5a}$, and $R^{5b}$ together with the N they are attached to form substituted or unsubstituted pyridyl.

In one embodiment, with respect to the bolaamphiphilic compound of formula VIIa-VIId, VIIIa-VIIId, IXa-IXc, or Xa-Xc, $R^{5a}$, and $R^{5b}$ together with the N they are attached to form substituted or unsubstituted monocyclic or bicyclic heterocyclyl.

In one embodiment, with respect to the bolaamphiphilic compound of formula VIIa-VIId, VIIIa-VIIId, IXa-IXc, or Xa-Xc, X is substituted or unsubstituted

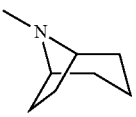

In one embodiment, with respect to the bolaamphiphilic compound of formula VIIa-VIId, VIIIa-VIIId, IXa-IXc, or Xa-Xc, X is

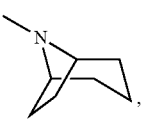

substituted with one or more groups selected from alkoxy, acetyl, and substituted or unsubstituted Ph.

In one embodiment, with respect to the bolaamphiphilic compound of formula VIIa-VIId, VIIIa-VIIId, IXa-IXc, or Xa-Xc, X is

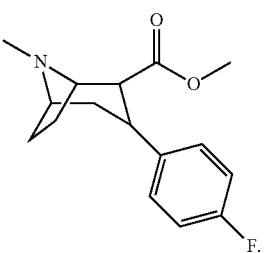 [SMILES: COC(=O)C1C(c2ccc(F)cc2)CC2CCC1N2C]

In one embodiment, with respect to the bolaamphiphilic compound of formula VIIa-VIId, VIIIa-VIIId, IXa-IXc, or Xa-Xc, X is —NMe$_2$ or —N$^+$Me$_3$.

In one embodiment, with respect to the bolaamphiphilic compound of formula VIIa-VIId, VIIIa-VIIId, IXa-IXc, or Xa-Xc, X is —N(Me)-CH$_2$CH$_2$—OAc or —N$^+$(Me)$_2$-CH$_2$CH$_2$—OAc.

In one embodiment, with respect to the bolaamphiphilic compound of formula VIIa-VIId, VIIIa-VIIId, IXa-IXc, or Xa-Xc, X is a chitosanyl group; and the chitosanyl group is a poly-(D)glucosaminyl group with MW of 3800 to 20,000 Daltons, and is attached to the core via N.

In one embodiment, the chitosanyl group is

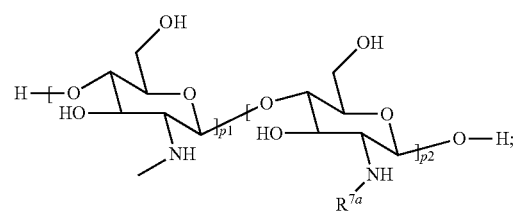

and wherein each p1 and p2 is independently an integer from 1-400; and each $R^{7a}$ is H or acyl.

In one embodiment, with respect to the bolaamphiphilic compound of formula I, II, III, IV, V, VI, VIIa-VIIc, VIIIa-VIIIc, IXa-IXc and Xa-Xc, the bolaamphiphilic compound is a pharmaceutically acceptable salt.

In one embodiment, with respect to the bolaamphiphilic compound of formula I, II, III, IV, V, VI, VIIa-VIIc, VIIIa-VIIIc, IXa-IXc and Xa-Xc, the bolaamphiphilic compound is in a form of a quaternary salt.

In one embodiment, with respect to the bolaamphiphilic compound of formula I, II, III, IV, V, VI, VIIa-VIIc, VIIIa-VIIIc, IXa-IXc and Xa-Xc, the bolaamphiphilic compound is in a form of a quaternary salt with pharmaceutically acceptable alkyl halide or alkyl tosylate.

In one embodiment, with respect to the bolaamphiphilic compound of formula I, II, III, IV, V, VI, VIIa-VIIc, VIIIa-VIIIc, IXa-IXc and Xa-Xc, the bolaamphiphilic compound is any one of the bolaamphilic compounds listed in Table 1.

In another specific aspect, provided herein are methods for incorporating HIV active drugs in the bolavesicles. In one embodiment, the bolavesicle comprises one or more bolaamphilic compounds described herein.

The Derivatives and Precursors disclosed can be prepared as illustrated in the Schemes provided herein. The syntheses can involve initial construction of, for example, vernonia oil or direct functionalization of natural derivatives by organic synthesis manipulations such as, but not limiting to, epoxide ring opening. In those processes involving oxiranyl ring opening, the epoxy group is opened by the addition of reagents such as carboxylic acids or organic or inorganic nucleophiles. Such ring opening results in a mixture of two products in which the new group is introduced at either of the two carbon atoms of the epoxide moiety. This provides beta substituted alcohols in which the substitution position most remote from the CO group of the main aliphatic chain of the vernonia oil derivative is arbitrarily assigned as position 1, while the neighboring substituted carbon position is designated position 2. For simplicity purposes only, the Derivatives and Precursors shown herein may indicate structures with the hydroxy group always at position 2 but the Derivatives and Precursors wherein the hydroxy is at position 1 are also encompassed by the invention. Thus, a radical of the formula —CH(OH)—CH(R)— refers to the substitution of —OH at either the carbon closer to the CO group, designated position 2 or to the carbon at position 1. Moreover, with respect to the preparation of symmetrical bolaamphiphiles made via introducing the head groups through an epoxy moiety (e.g., as in vernolic acid) or a double bond (—C═C—) as in mono unsaturated fatty acids (e.g., oleic acid) a mixture of three different derivatives will be produced. In certain embodiments, vesicles are prepared using the mixture of unfractionated positional isomers. In one aspect of this embodiment, where one or more bolas are prepared from vernolic acid, and in which a hydroxy group as well as the head group introduced through an epoxy or a fatty acid with the head group introduced through a double bond (—C═C—), the bola used in vesicle preparation can actually be a mixture of three different positional isomers.

In other embodiments, the three different derivatives are isolated. Accordingly, the vesicles disclosed herein can be made from a mixture of the three isomers of each derivative or, in other embodiments, the individual isomers can be isolated and used for preparation of vesicles.

Symmetrical bolaamphiphiles can form relatively stable self aggregate vesicle structures by the use of additives such as cholesterol and cholesterol derivatives (e.g., cholesterol hemisuccinate, cholesterol oleyl ether, anionic and cationic derivatives of cholesterol and the like), or other additives including single headed amphiphiles with one, two or multiple aliphatic chains such as phospholipids, zwitterionic, acidic, or cationic lipids. Examples of zwitterionic lipids are phosphatidylcholines, phosphatidylethanol amines and sphingomyelins. Examples of acidic amphiphilic lipids are phosphatidylglycerols, phosphatidylserines, phosphatidylinositols, and phosphatidic acids. Examples of cationic amphipathic lipids are diacyl trimethylammonium propanes, diacyl dimethylammonium propanes, and stearylamines cationic amphiphiles such as spermine cholesterol carbamates, and the like, in optimum concentrations which fill in the larger spaces on the outer surfaces, and/or add additional hydrophilicity to the particles. Such additives may be added to the reaction mixture during formation of nanoparticles to enhance stability of the nanoparticles by filling in the void volumes of in the upper surface of the vesicle membrane.

Stability of nano vesicles according to the present disclosure can be demonstrated by dynamic light scattering (DLS) and transmission electron microscopy (TEM). For example, suspensions of the vesicles can be left to stand for 1, 5, 10, and 30 days to assess the stability of the nanoparticle solution/suspension and then analyzed by DLS and TEM.

The vesicles disclosed herein may encapsulate within their core the active agent, which in particular embodiments is selected from peptides, proteins, nucleotides and or non-polymeric agents. In certain embodiments, the active agent is also associated via one or more non-covalent interactions to the vesicular membrane on the outer surface and/or the inner surface, optionally as pendant decorating the outer or inner surface, and may further be incorporated into the membrane surrounding the core. In certain aspects, biologically active peptides, proteins, nucleotides or non-polymeric agents that have a net electric charge, may associate ionically with oppositely charged headgroups on the vesicle surface and/or form salt complexes therewith.

In particular aspects of these embodiments, additives which may be bolaamphiphiles or single headed amphiphiles, comprise one or more branching alkyl chains bearing polar or ionic pendants, wherein the aliphatic portions act as anchors into the vesicle's membrane and the pendants (e.g., chitosan derivatives or polyamines or certain peptides) decorate the surface of the vesicle to enhance penetration through various biological barriers such as the intestinal tract and the BBB, and in some instances are also selectively hydrolyzed at a given site or within a given organ. The concentration of these additives is readily adjusted according to experimental determination.

In certain embodiments, the oral formulations of the present disclosure comprise agents that enhance penetration through the membranes of the GI tract and enable passage of intact nanoparticles containing the drug. These agents may be any of the additives mentioned above and, in particular aspects of these embodiment, include chitosan and derivatives thereof, serving as vehicle surface ligands, as decorations or pendants on the vesicles, or the agents may be excipients added to the formulation.

In other embodiments, the nanoparticles and vesicles disclosed herein may comprise the fluorescent marker carboxyfluorescein (CF) encapsulated therein while in particular aspects, the nanoparticle and vesicles of the present disclosure may be decorated with one or more of PEG, e.g. PEG2000-vernonia derivatives as pendants. For example, two kinds of PEG-vernonia derivatives can be used: PEG-ether derivatives, wherein PEG is bound via an ether bond to the oxygen of the opened epoxy ring of, e.g., vernolic acid and PEG-ester derivatives, wherein PEG is bound via an ester bond to the carboxylic group of, e.g., vernolic acid.

In other embodiments, vesicles, made from synthetic amphiphiles, as well as liposomes, made from synthetic or natural phospholipids, substantially (or totally) isolate the therapeutic agent from the environment allowing each vesicle or liposome to deliver many molecules of the therapeutic agent. Moreover, the surface properties of the vesicle or liposome can be modified for biological stability, enhanced penetration through biological barriers and targeting, independent of the physico-chemical properties of the encapsulated drug.

In still other embodiments, the headgroup is selected from: (i) choline or thiocholine, O-alkyl, N-alkyl or ester derivatives thereof; (ii) non-aromatic amino acids with functional side chains such as glutamic acid, aspartic acid, lysine or cysteine, or an aromatic amino acid such as tyrosine, tryptophan, phenylalanine and derivatives thereof such as levodopa (3,4-dihydroxy-phenylalanine) and p-aminophenylalanine; (iii) a peptide or a peptide derivative that is specifically cleaved by an enzyme at a diseased site selected from enkephalin, N-acetyl-ala-ala, a peptide that constitutes a domain recognized by beta and gamma secretases, and a peptide that is recognized by stromelysins; (iv) saccharides such as glucose, mannose and ascorbic acid; and (v) other compounds such as nicotine, cytosine, lobeline, polyethylene glycol, a cannabinoid, or folic acid.

In further embodiments, nano-sized particle and vesicles disclosed herein further comprise at least one additive for one or more of targeting purposes, enhancing permeability and increasing the stability the vesicle or particle. Such additives, in particular aspects, may selected from: (i) a single headed amphiphilic derivative comprising one, two or multiple aliphatic chains, preferably two aliphatic chains linked to a midsection/spacer region such as —NH—$(CH_2)_2$—N—$(CH_2)_2$—N—, or —O—$(CH_2)_2$—N—$(CH_2)_2$—O—, and a sole headgroup, which may be a selectively cleavable headgroup or one containing a polar or ionic selectively cleavable group or moiety, attached to the N atom in the middle of said midsection. In other aspects, the additive can be selected from among cholesterol and cholesterol derivatives such as cholesteryl hemmisuccinate; phospholipids, zwitterionic, acidic, or cationic lipids; chitosan and chitosan derivatives, such as vernolic acid-chitosan conjugate, quaternized chitosan, chitosan-polyethylene glycol (PEG) conjugates, chitosan-polypropylene glycol (PPG) conjugates, chitosan N-conjugated with different amino acids, carboxyalkylated chitosan, sulfonyl chitosan, carbohydrate-branched N-(carboxymethylidene) chitosan and N-(carboxymethyl) chitosan; polyamines such as protamine, polylysine or polyarginine; ligands of specific receptors at a target site of a biological environment such as nicotine, cytisine, lobeline, 1-glutamic acid MK801, morphine, enkephalins, benzodiazepines such as diazepam (valium) and librium, dopamine agonists, dopamine antagonists tricyclic antidepressants, muscarinic agonists, muscarinic antagonists, cannabinoids and arachidonyl ethanol amide; polycationic polymers such as polyethylene amine; peptides that enhance transport through the BBB such as OX 26, transferrins, polybrene, histone, cationic dendrimer, synthetic peptides and polymyxin B nonapeptide (PMBN); monosaccharides such as glucose, mannose, ascorbic acid and derivatives thereof; modified proteins or antibodies that undergo absorptive-mediated or receptor-mediated transcytosis through the blood-brain barrier, such as bradykinin B2 agonist RMP-7 or monoclonal antibody to the transferrin receptor; mucoadhesive polymers such as glycerides and steroidal detergents; and $Ca^{2+}$ chelators. The aforementioned head groups on the additives designed for one or more of targeting purposes and enhancing permeability may also be a head group, preferably on an asymmetric bolaamphiphile wherein the other head group is another moiety, or the head group on both sides of a symmetrical bolaamphiphile.

In other embodiments, nano-sized particle and vesicles discloser herein may comprises at least one biologically active agent is selected from: (i) a natural or synthetic peptide or protein such as analgesics peptides from the enkephalin class, insulin, insulin analogs, oxytocin, calcitonin, tyrotropin releasing hormone, follicle stimulating hormone, luteinizing hormone, vasopressin and vasopressin analogs, catalase, interleukin-II, interferon, colony stimulating factor, tumor necrosis factor (TNF), melanocyte-stimulating hormone, superoxide dismutase, glial cell derived neurotrophic factor (GDNF) or the Gly-Leu-Phe (GLF) families; (ii) nucleosides and polynucleotides selected from DNA or RNA molecules such as small interfering RNA (siRNA) or a DNA plasmid; (iii) antiviral and antibacterial; (iv) antineoplastic and chemotherapy agents such as cyclosporin, doxorubicin, epirubicin, bleomycin, cisplatin, carboplatin, vinca alkaloids, e.g. vincristine, Podophyllotoxin, taxanes, e.g. Taxol and Docetaxel, and topoisomerase inhibitors, e.g. irinotecan, topotecan.

In another specific aspect, provided herein are methods for brain-targeted drug delivery using the bolavesicles incorporated with HIV active drug.

In one particular embodiment, the HIV active drug is Tenofovir or ({[(2R)-1-(6-amino-9H-purin-9-yl)propan-2-yl]oxy}methyl)phosphonic acid.

In another particular embodiment, the HIV active drug is fosamprenavir. In another particular embodiment, the HIV active drug is enfuvirtide. In another particular embodiment, the HIV active drug is saquinavir. In another particular embodiment, the HIV active drug is lamivudine. In another particular embodiment, the HIV active drug is stavudine.

In another specific aspect, provided herein are methods for delivering Tenofovir to the brain.

In another specific aspect, provided herein are methods for delivering fosamprenavir, enfuvirtide, saquinavir, lamivudine or stavudine to the brain.

In another specific aspect, provided herein are nano-particles, comprising one or more bolaamphiphilic compounds and Tenofovir, fosamprenavir, enfuvirtide, saquinavir, lamivudine or stavudine. In one embodiment, the bolaamphiphilic compounds and Tenofovir, fosamprenavir, enfuvirtide, saquinavir, lamivudine or stavudine are encapsulated within the nano-particle.

In another specific aspect, provided herein are pharmaceutical compositions, comprising a nano-sized particle comprising one or more bolaamphiphilic compounds and Tenofovir, fosamprenavir, enfuvirtide, saquinavir, lamivudine or stavudine; and a pharmaceutically acceptable carrier.

In another specific aspect, provided herein are methods for treatment or diagnosis of diseases or disorders selected from HIV and related diseases using the nano-particles, pharmaceutical compositions or formulations of the present invention.

In certain embodiments, vesicle formation is carried out in the presence of an additive that increases encapsulation of a therapeutic agent. In one aspect of this embodiment, the additive is stearyl amine. In another aspect, the therapeutic agent is an antiviral agent, while in a still further aspect the antiviral agent is Tenofovir.

In certain embodiments, the present disclosure is directed to a method of treatment of a patient afflicted with a viral disease comprising administration of vesicles described herein. In one aspect of this embodiment, the patient is a human AIDS patient in need of such treatment. In particular aspects of this embodiment, the vesicles are formed in the presence of an additive that increases encapsulation of a therapeutic agent. In one aspect of this embodiment, the additive is stearyl amine. In another aspect, the therapeutic agent is an antiviral agent, while in a still further aspect the antiviral agent is Tenofovir. In another aspect of this embodiment, the virus is HIV.

Additional embodiments within the scope provided herein are set forth in non-limiting fashion elsewhere herein and in the examples. It should be understood that these examples are for illustrative purposes only and are not to be construed as limiting in any manner.

Pharmaceutical Compositions

In another aspect, the invention provides a pharmaceutical composition comprising a pharmaceutically acceptable carrier and a pharmaceutically effective amount of a compound of Formula I or a complex thereof.

When employed as pharmaceuticals, the compounds provided herein are typically administered in the form of a pharmaceutical composition. Such compositions can be prepared in a manner well known in the pharmaceutical art and comprise at least one active compound.

In certain embodiments, with respect to the pharmaceutical composition, the carrier is a parenteral carrier, oral or topical carrier.

The present invention also relates to a compound or pharmaceutical composition of compound according to Formula I; or a pharmaceutically acceptable salt or solvate thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of compounds of Formula I. In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salts of compounds of Formula I. The acids which are used to prepare the pharmaceutically acceptable salts are those which form non-toxic acid addition salts, i.e. salts containing pharmacologically acceptable anions such as the hydrochloride, hydroiodide, hydrobromide, nitrate, sulfate, bisulfate, πhosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Formulation 1

Injection

A compound of the invention may be dissolved or suspended in a buffered sterile saline injectable aqueous medium to a concentration of approximately 5 mg/mL.

In particular embodiments, the formulations of the disclosure comprise vesicles prepared as described herein. In certain embodiments, such vesicle formation comprise an additive that increases encapsulation of a therapeutic agent. In one aspect of this embodiment, the additive is stearyl amine. In another aspect, the therapeutic agent is an antiviral agent, while in a still further aspect the antiviral agent is Tenofovir.

Methods of Treatment

Bolaamphiphilic vesicles (bolavesicles) may have certain advantages over conventional liposomes as potential vehicles for drug delivery. Bolavesicles have thinner membranes than comparable liposomal bilayer, and therefore possess bigger inner volume and hence higher encapsulation capacity than liposomes of the same diameter. Moreover, bolavesicles are more physically-stable than conventional liposomes in part because of reduced limit exchange, but can be destabilized in a triggered fashion (e.g., by hydrolysis of the headgroups using a specific enzymatic reaction) thus allowing controlled release of the encapsulated material at the site of action (i.e., drug targeting). In still another aspect the vesicles formed from the bolaamphiphiles contain additives that help to stabilize the vesicles, by stabilizing the vesicle's membranes, such as but not limited to cholesterol derivatives such as cholesteryl hemisuccinate and cholesterol itself and combinations such as cholesteryl hemisuccinate and cholesterol. In still another embodiments the vesicles in addition to these components have another additives which decorates the outer vesicle membranes with groups or pendants that enhance penetration though biological barriers such as the BBB, or groups for targeting to specific sites.

Thus, various HIV active drug molecules can be encapsulated in the bolaamphiphilic vesicles and then delivered to the brain in sufficient concentrations for therapeutic use.

The bolaamphiphiles aggregate into encapsulating monolayer membranes which, together with additional additives for stability and additives for functional surface groups, provide vesicle stability, penetrability through the BBB and a controlled release mechanism that enables the release of the encapsulated drug primarily in the brain.

General Synthetic Procedures

The compounds provided herein can be purchased or prepared from readily available starting materials using the following general methods and procedures. See, e.g., Synthetic Schemes below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography or HPLC. The following schemes are presented with details as to the preparation of representative substituted biarylamides that have been listed herein. The compounds provided herein may be prepared from known or commercially available starting materials and reagents by one skilled in the art of organic synthesis.

The enantiomerically pure compounds may be prepared according to any techniques known to those of skill in the art. For instance, they may be prepared by chiral or asymmetric synthesis from a suitable optically pure precursor or obtained from a racemate by any conventional technique, for example, by chromatographic resolution using a chiral column, TLC or by the preparation of diastereoisomers, separation thereof and regeneration of the desired enantiomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, NY, 1962); and S. H. Wilen *Tables of Resolving Agents and Optical Resolutions* 268 (E. L. Eliel ed., Univ. of Notre Dame Press, Notre Dame, 1N, 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

In certain embodiments, an enantiomerically pure compound of formula (I) may be obtained by reaction of the racemate with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically pure compounds can also be recovered either from the crystallized diastereomer or from the mother liquor, depending on the solubility properties of the particular acid resolving agent employed and the particular acid enantiomer used. The identity and optical purity of the particular compound so recovered can be determined by polarimetry or other analytical methods known in the art. The diastereoisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation.

In certain embodiments, enantiomerically pure compound can be separated from racemic compound by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

ABBREVIATIONS

BBB, blood brain barrier
BCECs, brain capillary endothelial cells
CF, carboxyfluorescein
CHEMS, cholesteryl hemisuccinate
CHOL, cholesterol
Cryo-TEM, Cryo-transmission electron microscope
DAPI, 4',6-diamidino-2-phenylindole
DDS, drug delivery system
DLS, dynamic light scattering
DMPC, 1,2-dimyristoyl-sn-glycero-3-phosphocholine
DMPE, 1,2-dimyristoyl-sn-glycero-3-phosphoethanolamine
DMPG,1,2-dimyristoyl-sn-glycero-3-phospho-(1'-rac-glycerol)
EPR, electron paramagnetic resonance
FACS, fluorescence-activated cell sorting
FCR, fluorescence colorimetric response
GUVs, giant unilamellar vesicles
HPLC, high performance liquid chromatography IR, infrared
MRI, magnetic resonance imaging
NMR, nuclear magnetic resonance
NPs, nanoparticles
PBS, phosphate buffered saline
PC, phosphatidylcholine
PDA, polydiacetylene.
TMA-DPH, 1-(4 trimethylammoniumphenyl)-6-phenyl-1,3,5-hexatriene Example 1

Bolaamphiphile Synthesis

The boloamphiphles or bolaamphiphilic compounds of the invention can be synthesized following the procedures described previously (see below).

Briefly, the carboxylic group of methyl vernolate or vernolic acid was interacted with aliphatic diols to obtain bisvernolesters. Then the epoxy group of the vernolate moiety, located on C12 and C13 of the aliphatic chain of vernolic acid, was used to introduce two ACh headgroups on the two vicinal carbons obtained after the opening of the oxirane ring. For GLH-20 (Table 1), the ACh head group was attached to the vernolate skeleton through the nitrogen atom of the choline moiety. The bolaamphiphile was prepared in a two-stage synthesis: First, opening of the epoxy ring with a haloacetic acid and, second, quaternization with the N,N-dimethylamino ethyl acetate. For GLH-19 (Table 1) that contains an ACh head group attached to the vernolate skeleton through the acetyl group, the bolaamphiphile was prepared in a three-stage synthesis, including opening of the epoxy ring with glutaric acid, then esterification of the free carboxylic group with N,N-dimethyl amino ethanol and the final product was obtained by quaternization of the head group, using methyl iodide followed by exchange of the iodide ion by chloride using an ion exchange resin.

Each bolaamphiphile was characterized by mass spectrometry, NMR and IR spectroscopy. The purity of the two bolaamphiphiles was >97% as determined by HPLC.

Materials. Iron(III) acetylacetonate (Fe(acac)$_3$), diphenyl ether, 1,2-hexadecanediol, oleic acid, oleylamine, and carboxyfluorescein (CF) were purchased from Sigma Aldrich (Rehovot, Israel). Chloroform and ethanol were purchased from Bio-Lab Ltd. Jerusalem, Israel. 1,2-dimyristoyl-sn-glycero-3-phospho-(1'-rac-glycerol) (DMPG), 1,2-dimyristoyl-sn-glycero-3-phosphoethanolamine (DMPE),1,2-dimyristoyl-sn-glycero-3-phosphocholine (DMPC), cholesterol (CHOL), cholesteryl hemisuccinate (CHEMS) were purchased from Avanti Lipids (Alabaster, Ala., USA), The diacetylenic monomer 10,12-tricosadiynoic acid was purchased from Alfa Aesar (Karlsruhe, Germany), and purified by dissolving the powder in chloroform, filtering the resulting solution through a 0.45 μm nylon filter (Whatman Inc., Clifton, N.J., USA), and evaporation of the solvent. 1-(4 trimethylammoniumphenyl)-6-phenyl-1,3,5-hexatriene (TMA-DPH) was purchased from Molecular Probes Inc. (Eugene, Oreg., USA).

Synthesis of Representative Bolaamphiphilic Compounds

The synthesis bolaamphiphilic compounds of this invention can be carried out in accordance with the methods described previously (*Chemistry and Physics of Lipids* 2008, 153, 85-97; *Journal of Liposome Research* 2010, 20, 147-59; WO2002/055011; WO2003/047499; or WO2010/128504) and using the appropriate reagents, starting materials, and purification methods known to those skilled in the art. Table 1 lists the representative bolaamphiphilic compounds of the invention.

TABLE 1

Representative Bolaamphiphiles

| # | Structure |
|---|---|
| GLH-3 | 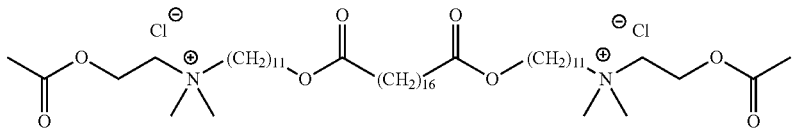 |
| GLH-4 | 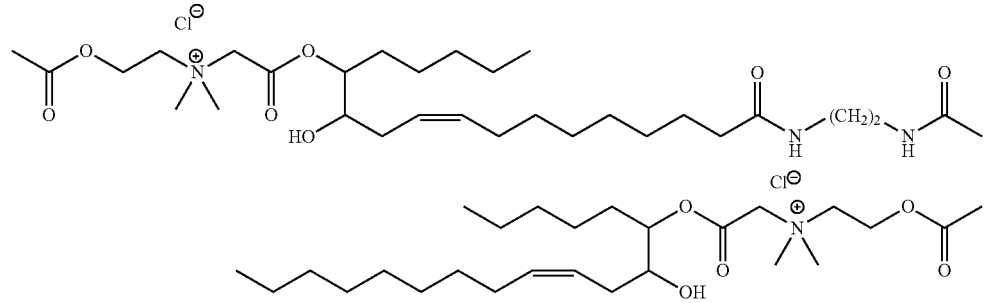 |

TABLE 1-continued
Representative Bolaamphiphiles
| # | Structure |
|---|---|
| GLH-5 | 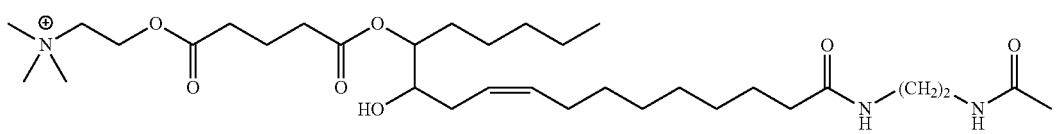 |
| GLH-6 [a] | 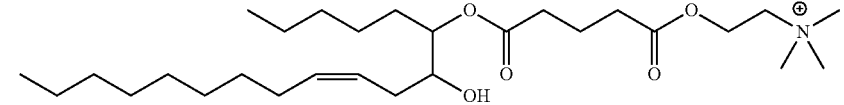 |
| GLH-7 | 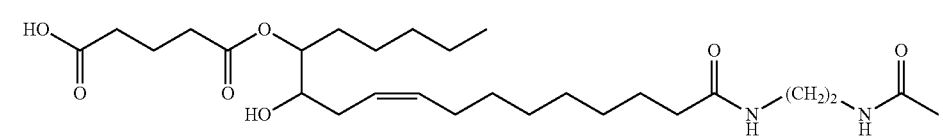 |
| GLH-8 | 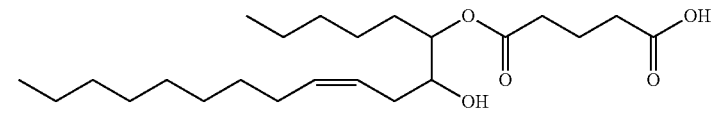 |
| GLH-9 | 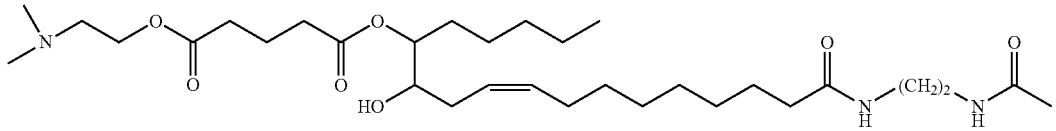 |

TABLE 1-continued

Representative Bolaamphiphiles

| # | Structure |
|---|---|
| GLH-10 | (chemical structure) |
| GLH-11 | (chemical structure) |
| GLH-12 [a] | (chemical structure) |
| GLH-13 [a] | (chemical structure) |
| GLH-13 [a] | (chemical structure) |
| GLH-14 | (chemical structure) |
| GLH-15 | (chemical structure) |
| GLH-16 | (chemical structure) |

TABLE 1-continued
Representative Bolaamphiphiles
| # | Structure |
|---|---|
| GLH-17 | 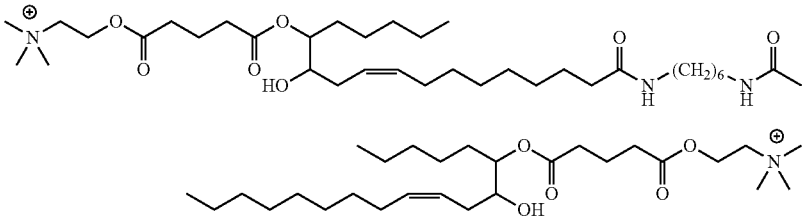 |
| GLH-18 | 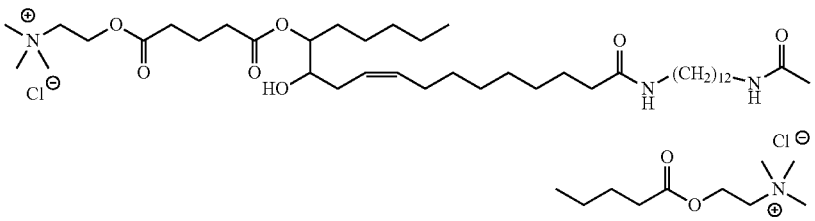 |
| GLH-19 | 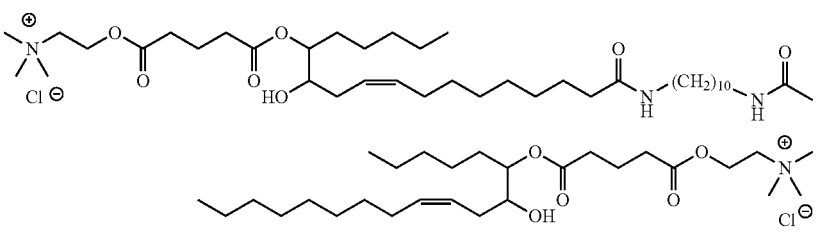 |
| GLH-20 | 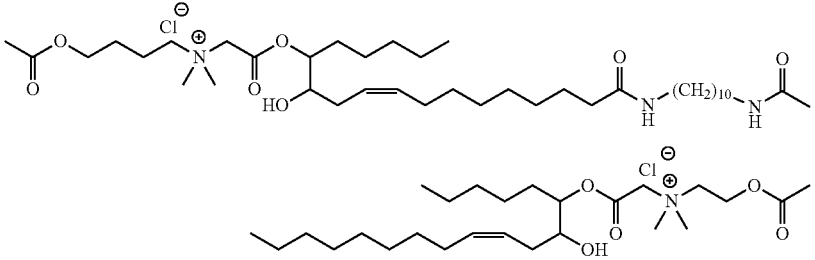 |
| GLH-21 | 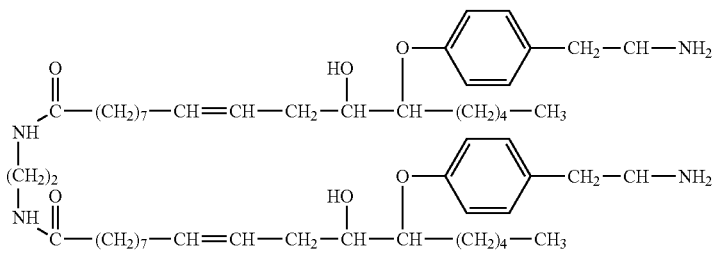 |
| GLH-22 | 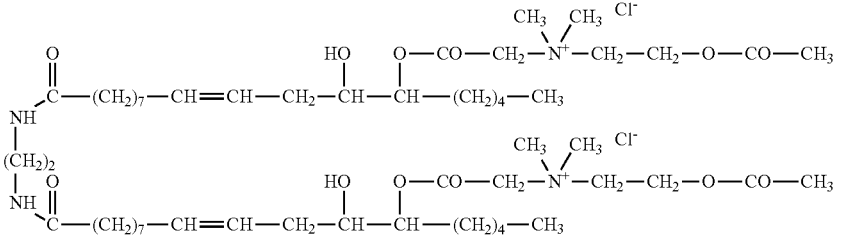 |

TABLE 1-continued
Representative Bolaamphiphiles
| # | Structure |
|---|---|
| GLH-23 | 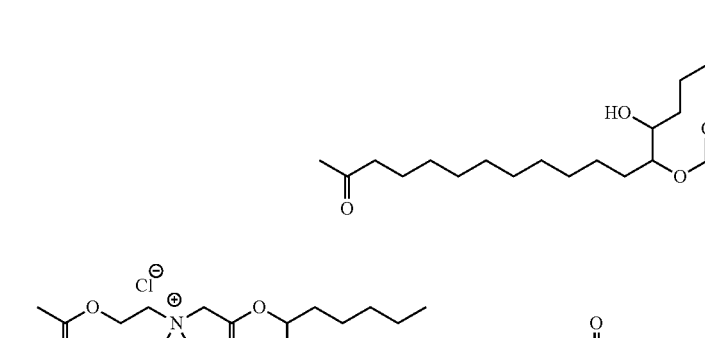 |
| GLH-24 | 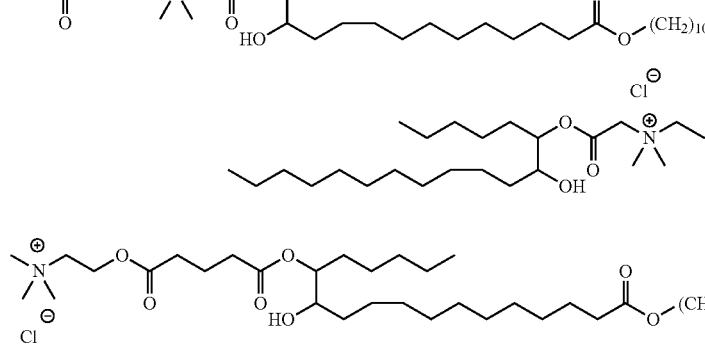 |
| GLH-25 | 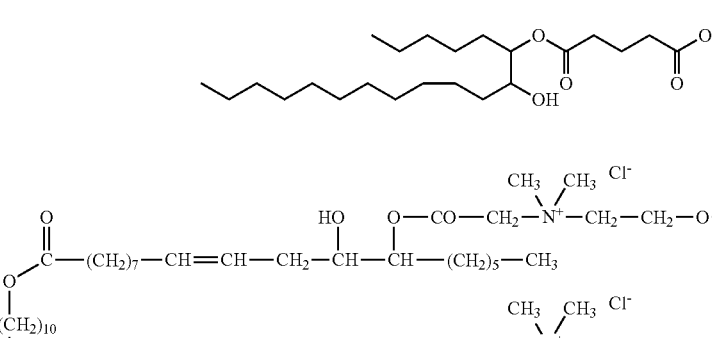 |
| GLH-26 | 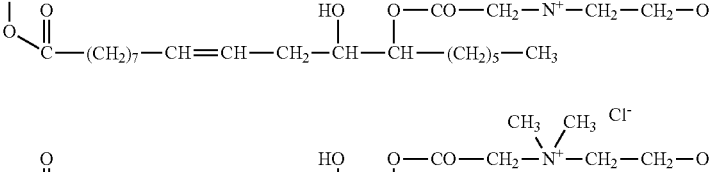 |
| GLH-27 | 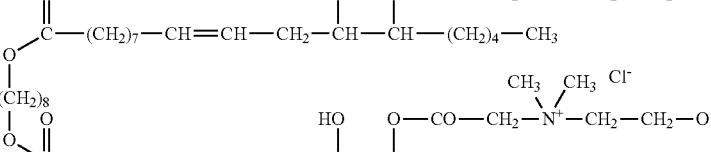 |

TABLE 1-continued
Representative Bolaamphiphiles
| # | Structure |
|---|---|
| GLH-28 | 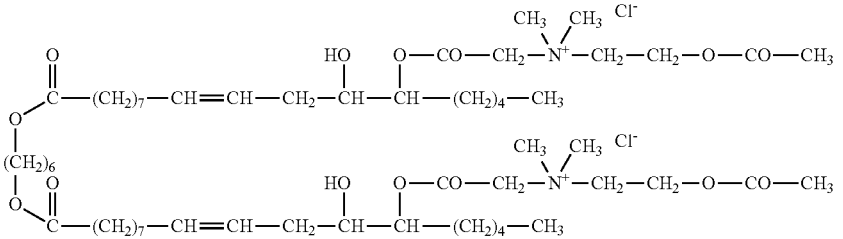 |
| GLH-29 | 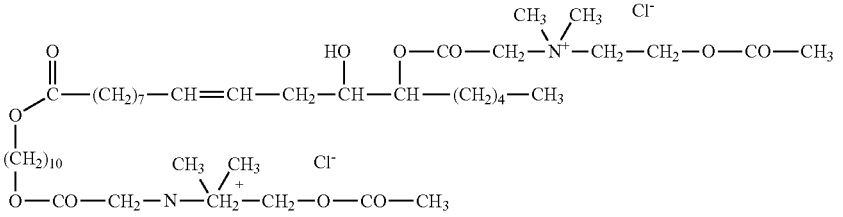 |
| GLH-30 | 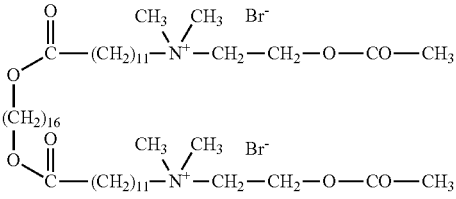 |
| GLH-30 | 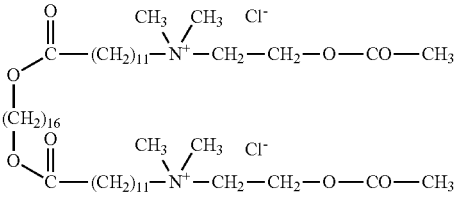 |
| GLH-31 | 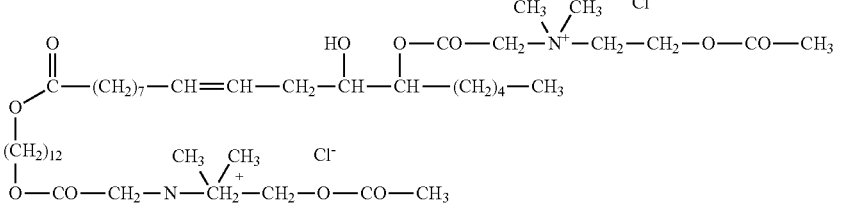 |
| GLH-32 | 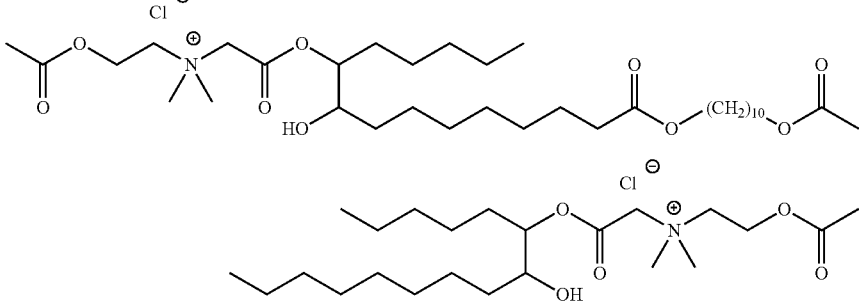 |

TABLE 1-continued
Representative Bolaamphiphiles
| # | Structure |
|---|---|
| GLH-33 | 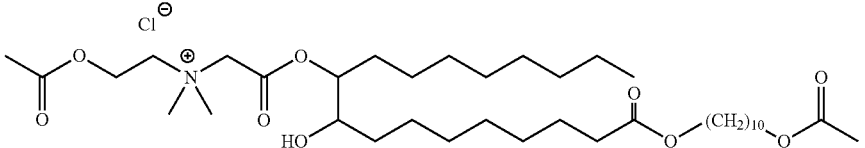 |
| GLH-34 | 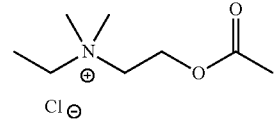 |
| GLH-35 | 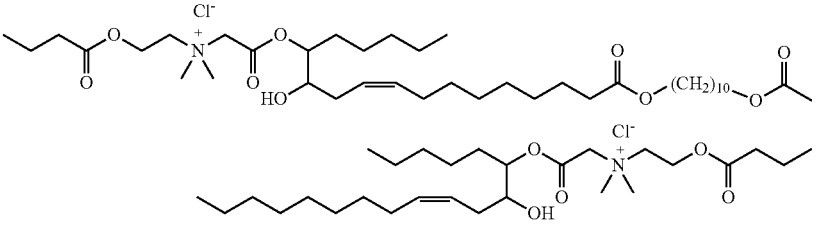 |
| GLH-36 | 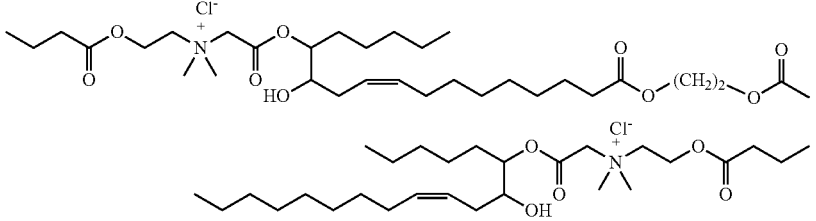 |
| GLH-37 | 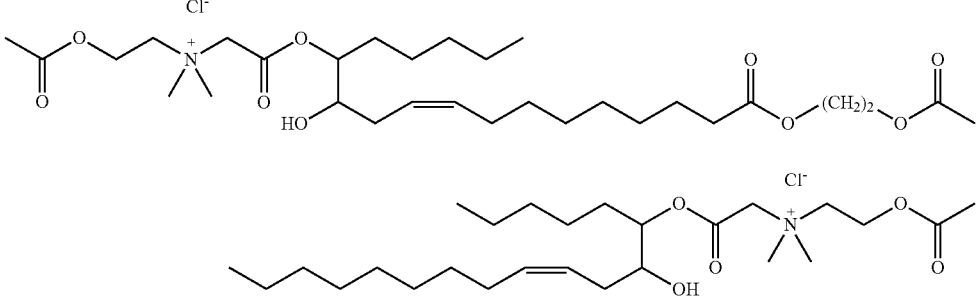 |

TABLE 1-continued
Representative Bolaamphiphiles
| # | Structure |
|---|---|
| GLH-38 | 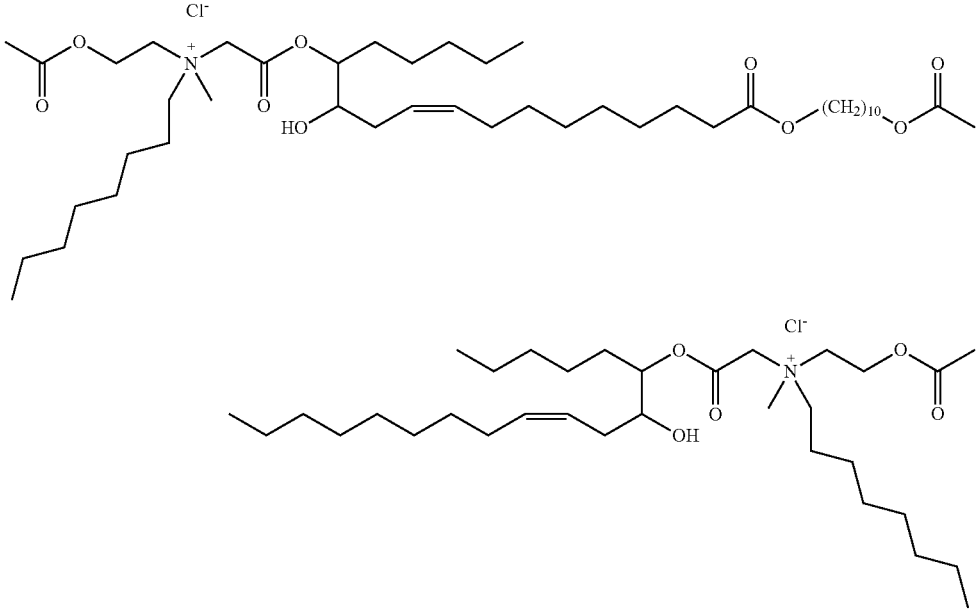 |
| GLH-39[a] | 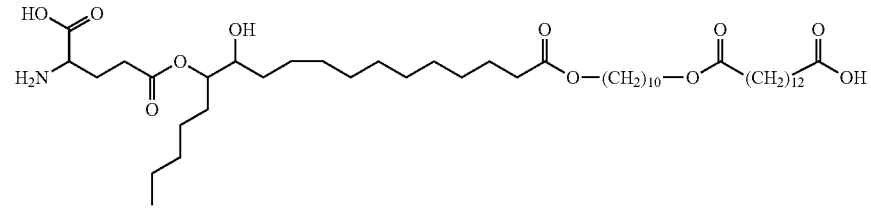 |
| GLH-40 | 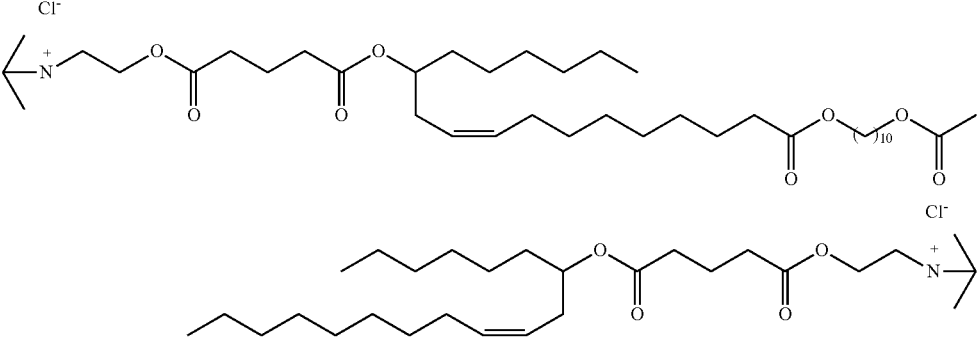 |
| GLH-41 | 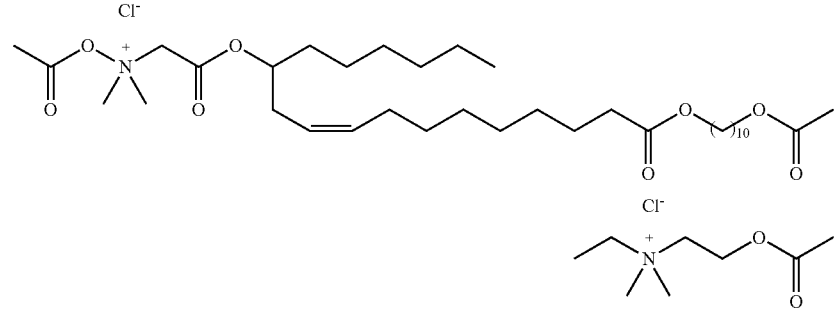 |

TABLE 1-continued

Representative Bolaamphiphiles

| # | Structure |
|---|-----------|
| GLH-42 [a] | (structure) |
| GLH-43 [a] | (structure) |
| GLH-44 | (structure) |
| GLH-45 | (structure) |
| GLH-46 | (structure) |
| GLH-47 | (structure) |

TABLE 1-continued

Representative Bolaamphiphiles

| # | Structure |
|---|---|
| GLH-48 | (structure) |
| GLH-49 [a] | (structure) |
| GLH-50 [a] | (structure) |
| GLH-51 [a] | (structure) |
| GLH-52 [a] | (structure) |
| GLH-53 [a] | (structure) |
| GLH-54 [a] | (structure) |
| GLH-55 | (structure) |

TABLE 1-continued

Representative Bolaamphiphiles

| # | Structure |
|---|---|
| GLH-56 | 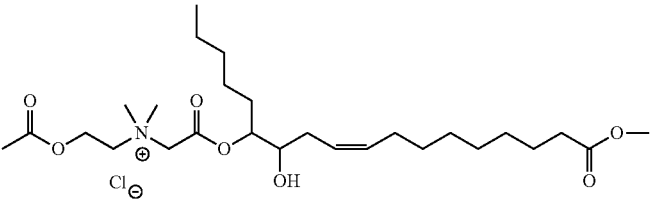 |
| GLH-57 | 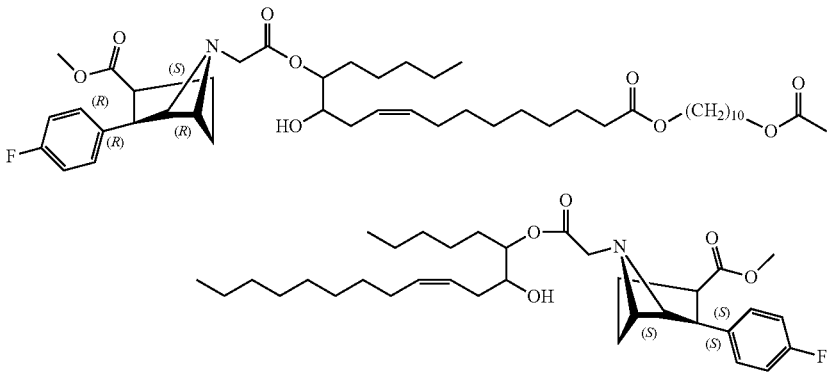 |

[a] -an intermediate

Example 2

Bolavesicle Preparation and Characterization

Bolaamphiphiles, cholesterol, and CHMES (2:1:1 mole ratio) are dissolved in chloroform or a suitable solvent. 0.5 mg of the HIV active drug dispersed in chloroform is added to the mix. The solvents are evaporated under vacuum and the resultant thin films are hydrated in 0.2 mg/mL CF solution in PBS and probe-sonicated (Vibra-Cell VCX130 sonicator, Sonics and Materials Inc., Newtown, Conn., USA) with amplitude 20%, pulse on: 15 sec, pulse off: 10 sec to achieve homogenous vesicle dispersions. Vesicle size and zeta potential were determined using a Zetasizer Nano ZS (Malvern Instruments, UK). The amount of the HIV active drug encapsulated in the vesicles can be determined by HPLC and/or UV spectroscopy (G Gnanarajan, et al, 2009) after separating the non-encapsulated drug, by size exclusion chromatography (on Sephadex-G50).

Spectral Characterization

Example 3

Electron Paramagnetic Resonance (EPR)

EPR spectra of HIV active drug embedded bolavesicles resuspended in PBS can be obtained using a Bruker EMX-220 X-band ($v\sim 9.4$ GHz) EPR spectrometer equipped with an Oxford Instruments ESR 900 temperature accessories and an Agilent 53150A frequency counter. Spectra can be recorded at room temperature with the non-saturating incident microwave power 20 mW and the 100 KHz magnetic field modulation of 0.2 mT amplitude. Processing of EPR spectra, determination of spectral parameters can be done using Bruker WIN-EPR software.

Example 4

Cryogenic Transmission Electron Microscopy (Cryo-TEM)

Figure 1B:
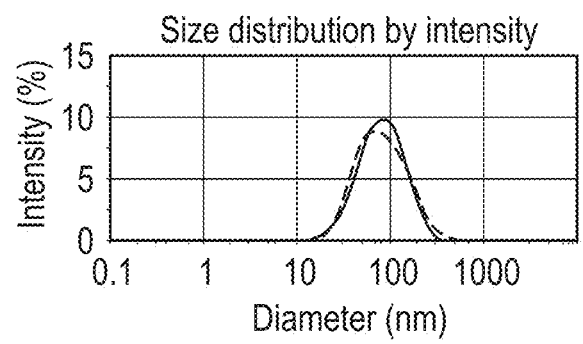

Specimens studied by cryo-TEM were prepared. Sample solutions (4 μL) are deposited on a glow discharged, 300 mesh, lacey carbon copper grids (Ted Pella, Redding, Calif., USA). The excess liquid is blotted and the specimen was vitrified in a Leica EM GP vitrification system in which the temperature and relative humidity are controlled. The samples are examined at −180° C. using a FEI Tecnai 12 G2 TWIN TEM equipped with a Gatan 626 cold stage, and the images are recorded (Gatan model 794 charge-coupled device camera) at 120 kV in low-dose mode. FIG. 1 shows TEM micrograph of vesicles from GLH-20 (A) and their size distribution determined by DLS (B).

Assays

Example 5

Lipid/polydiacetylene (PDA) Assay

Lipid/polydiacetylene (PDA) vesicles (PDADMPC 3:2, mole ratio) are prepared by dissolving the lipid components in chloroform/ethanol and drying together in vacuo. Vesicles are subsequently prepared in DDW by probe-sonication of the aqueous mixture at 70° C. for 3 min. The vesicle samples are then cooled at room temperature for an hour and kept at 4° C. overnight. The vesicles are then polymerized using irradiation at 254 nm for 10-20 s, with the resulting emulsions exhibiting an intense blue appearance. PDA fluorescence is measured in 96-well microplates (Greiner Bio-One GmbH, Frickenhausen, Germany) on a Fluoroscan Ascent fluorescence plate reader (Thermo Vantaa, Finland). All measurements are performed at room temperature at 485 nm excitation and 555 nm emission using LP filters with normal slits. Acquisition of data is automatically performed every 5 min for 60 min. Samples comprised 30 μL of DMPCPDA vesicles and 5 μL bolaamphiphilic vesicles assembled with HIV drug, followed by addition of 30 μL 50 mM Tris-base buffer (pH 8.0).

A quantitative value for the increasing of the fluorescence intensity within the PDA/PC-labeled vesicles is given by the fluorescence colorimetric response (% FCR), which is defined as follows[27]:

$$\% \ FCR = [(F_I - F_0)/F_{100}] \cdot 100 \quad \text{Eq. 1.}$$

Where $F_I$ is the fluorescence emission of the lipid/PDA vesicles after addition of the tested membrane-active compounds, $F_0$ is the fluorescence of the control sample (without addition of the compounds), and $F_{100}$ is the fluorescence of a sample heated to produce the highest fluorescence emission of the red PDA phase minus the fluorescence of the control sample.

Example 6

Cell Culture b.End3 immortalized mouse brain capillary endothelium cells are kindly provided by Prof. Philip Lazarovici (Institute for Drug Research, School of Pharmacy, The Hebrew University of Jerusalem, Israel). The b.End3 cells were cultured in DMEM medium supplemented with 10% fetal bovine serum, 2 mM L-Glutamine, 100 IU/mL penicillin and 100 mg/mL streptomycin (Biological Industries Ltd., Beit Haemek, Israel). The cells are maintained in an incubator at 37° C. in a humidified atmosphere with 5% $CO_2$.

Example 7

Figure 2A:
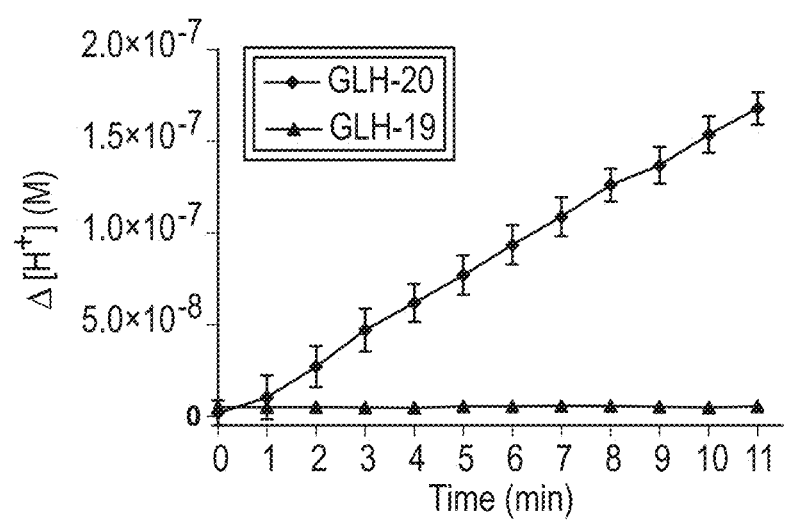
FIG. 2A: Head group hydrolysis by AChE of GLH-19 (▲ symbols) and GLH-20 (♦ symbols).
Figure 2B:
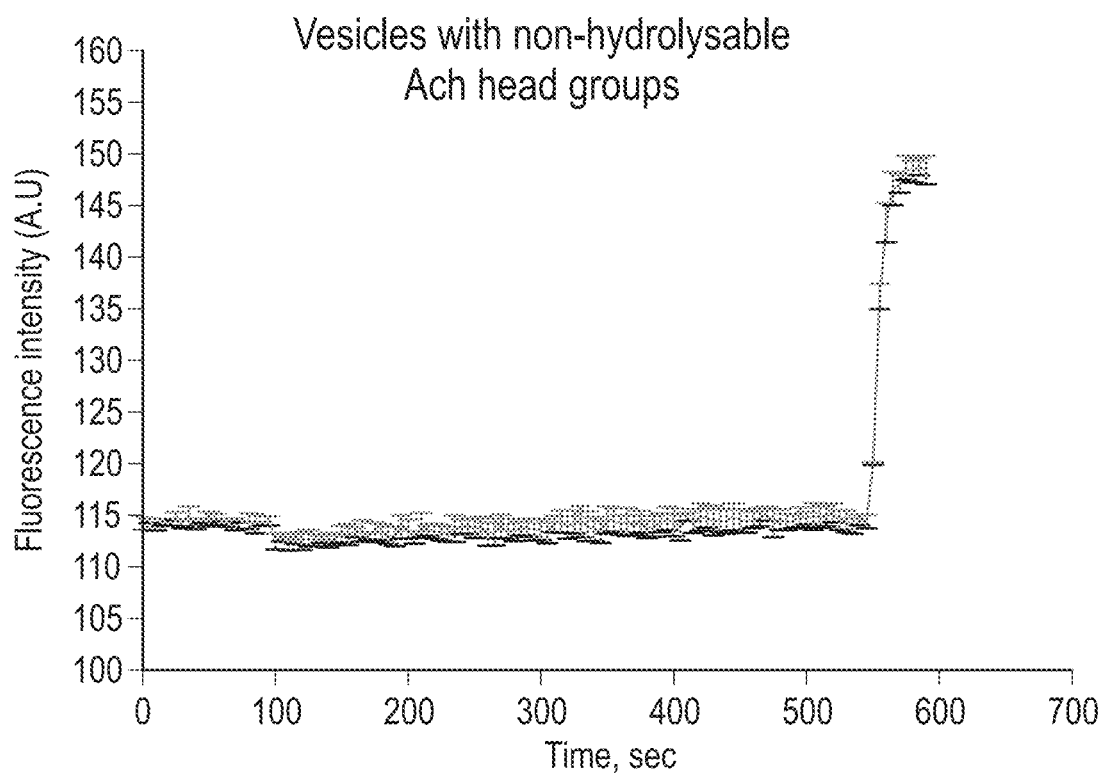
FIG. 2B: release of CF from GLH-19 vesicles.
Figure 2C:
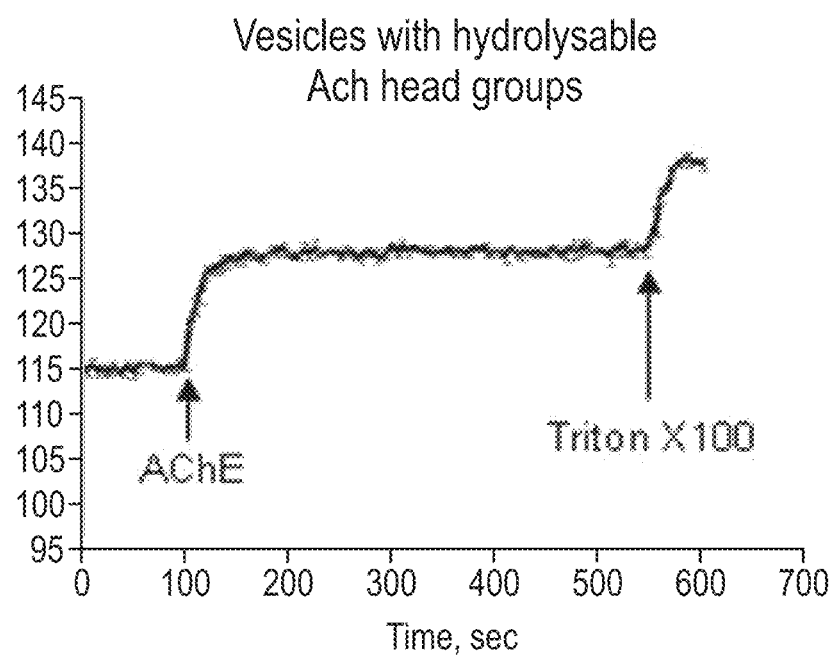
FIG. 2C: Release of CF from GLH-20 vesicles.
Figure 3A:
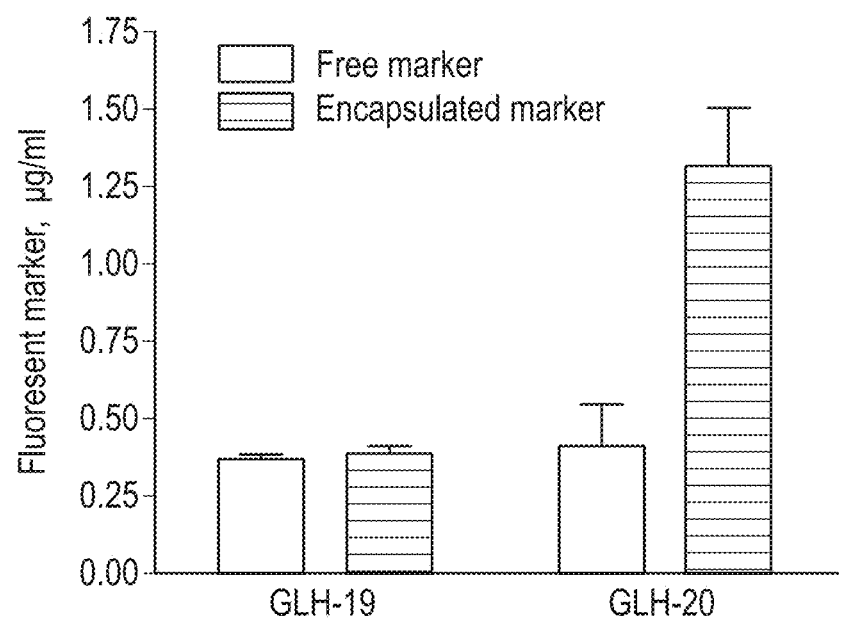
FIG. 3A: CF accumulation in brain after i.v. injection of encapsulated and non-encapsulated CF. Only GLH-20 vesicles allow accumulation of CF in the brain.
Figure 3B:
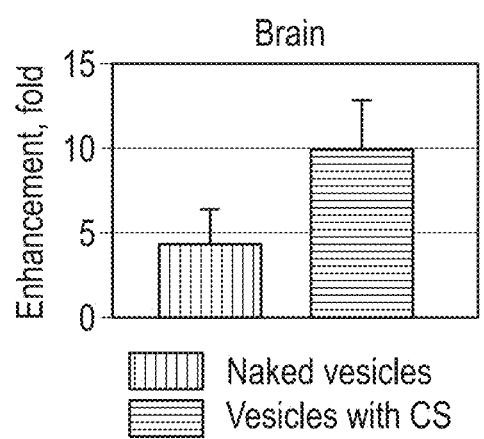
FIG. 3B demonstrates that CS improves GLH-20 vesicles' penetration into the brain.
Figure 4A:
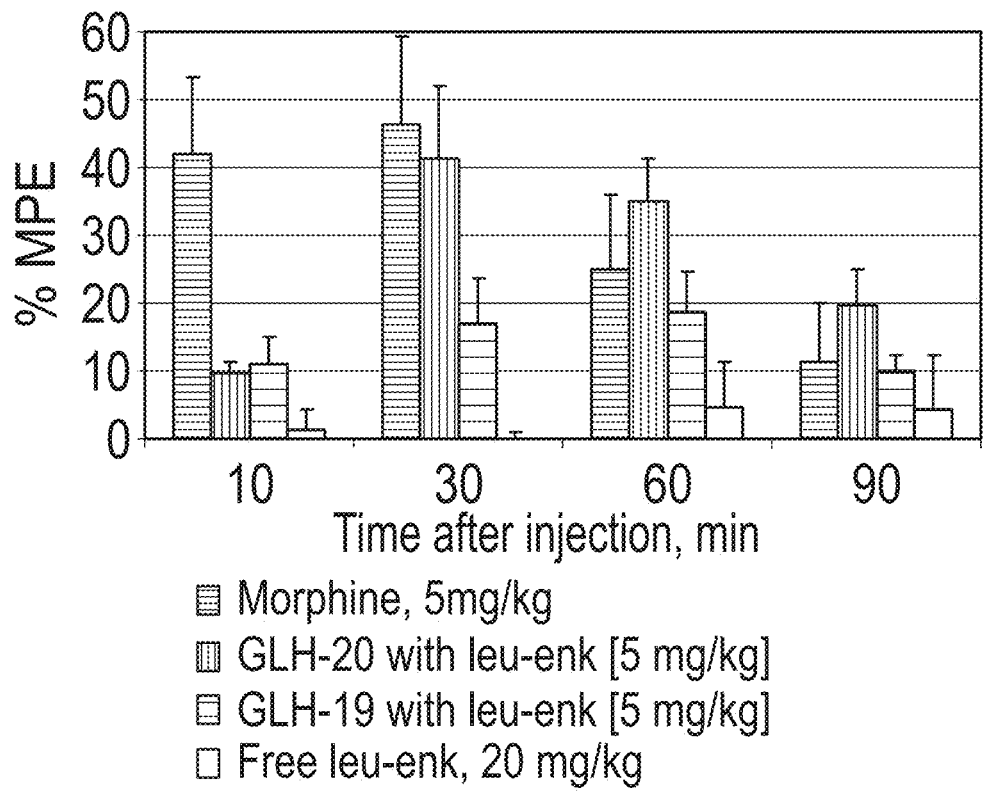
FIG. 4A: Analgesia after i.v. injection of enkephalin non-encapsulated and encapsulated in vesicles. Analgesia (compared with morphine, which was used as a positive control) is obtained only when enkephalin is encapsulated in GLH-20 vesicles, the head groups of which are hydrolyzed by ChE.
Figure 4B:
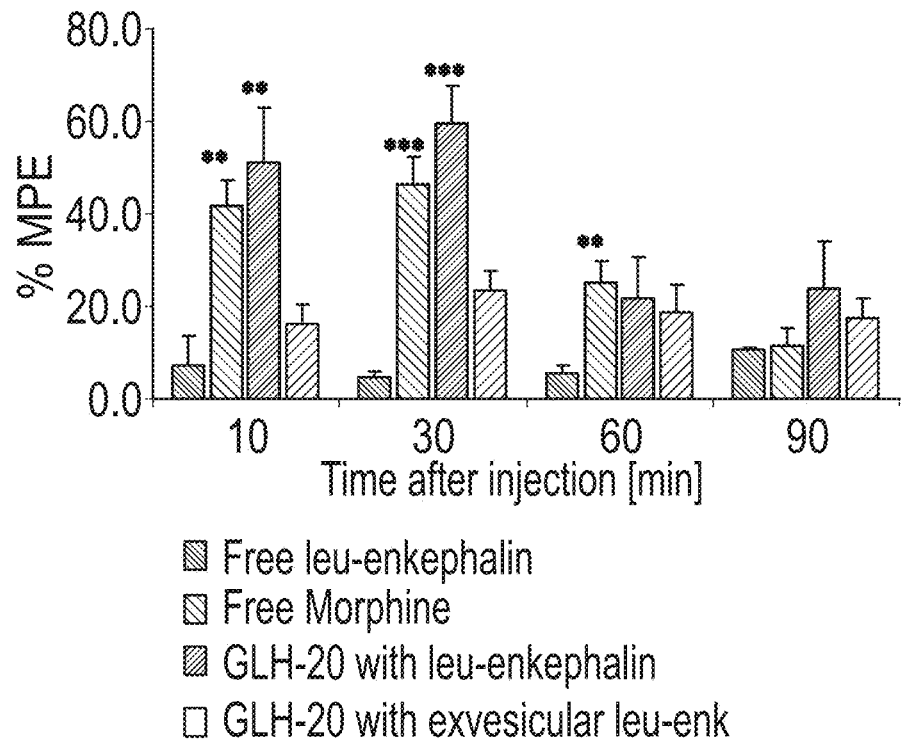
FIG. 4B demonstrate that the vesicles do not disrupt the BBB since non-encapsulated enkephalin co-injected with empty vesicles (extravesicular enkephalin) did not cause analgesia. Significantly different from free leu-enkephalin (t-test, $P<0.01$). *Significantly different from free leu-enkephalin (t-test, $P<0.001$).

Internalization of CF by the Cells In Vitro b.End3 cells are grown on 24-well plates or on coverslips (for FACS and fluorescence microscopy analysis, respectively). The medium is replaced with culture medium without serum and CF solution, or tested bolavesicles (equivalent to 0.5 mg/mL CF), or equivalent volume of the medium are added to the cells and incubated for 5 hr at 4° C. or at 37° C. At the end of the incubation, cells are extensively washed with complete medium and with PBS, and are either detached from the plates using trypsin-EDTA solution (Biological Industries Ltd., Beit Haemek, Israel) and analyzed by FACS (FACSCalibur Flow Cytometer, BD Biosciences, USA), or fixed with 2.5% formaldehyde in PBS, washed twice with PBS, mounted on slides using Mowiol-based mounting solution and analyzed using a FV1000-IX81 confocal microscope (Olympus, Tokyo, Japan) equipped with 60× objective. All the images are acquired using the same imaging settings and are not corrected or modified. The FIG. 2 shows head group hydrolysis by AChE (A) of GLH-19 (blue) and GLH-20 (red) and release of CF from GLH-19 vesicles (B) and GLH-20 vesicles (C). AChE causes the release of encapsulated material from GLH-20 vesicles, but not from GLH-19 vesicles (FIG. 2). The vesicles are capable of delivering small molecules, such as carboxyfluorescein (CF), into a mouse brain, but the fluorescent dye accumulates only if it is delivered in vesicles that release their encapsulated CF in presence of AChE, namely, GLH-20 vesicles (FIG. 3A). These results suggest that the release is due to head group hydrolysis by AChE in the brain. Corroboration for this conclusion also comes from an experiment showing that when an analgesic peptide is delivered to the brain by the bola vesicles, analgesia (which is caused when the encapsulated peptide is released in the brain) was observed only with GLH-20 vesicles, but not by GLH-19 vesicles (FIG. 4A). The vesicles do not break the BBB, but rather penetrate it in their intact form, as indicated by the finding that analgesia is obtained only when enkephalin is administered while encapsulated within the vesicles, but not when free enkephalin is administered together with empty vesicles (FIG. 4B).

The ACh head groups also provide the vesicles with cationic surfaces, which promote penetration through the BBB [Lu et al, 2005] and transport of the encapsulated material into the brain. Toxicity studies showed that the dose which induced the first toxic signs was 10-20 times higher than the doses needed to obtain analgesia by encapsulated analgesic peptides.

The addition of chitosan (CS) surface groups, by employing CS-vernolate conjugates, increased BBB permeability of the vesicles (FIG. 4B), probably by increasing transcytosis [Newton, 2006]. However, the CS groups, when added to the vesicles by employing fatty acid-CS conjugate (in this case, vernolic acid), are not stable in circulation as surface groups because of the low energy barrier for lipid exchange of such conjugates.

Figure 5A:
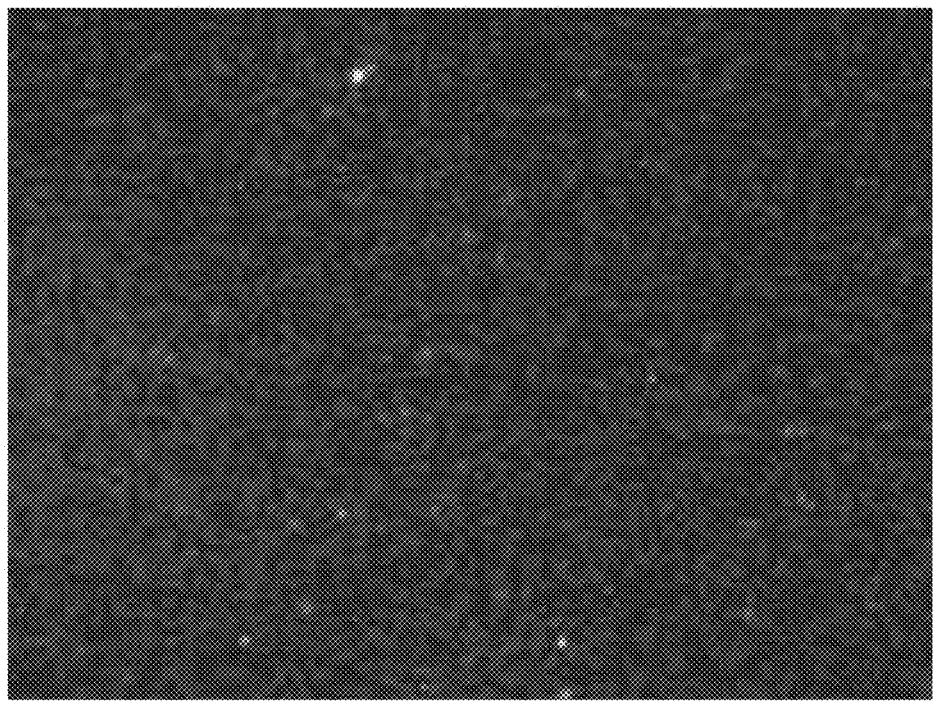
FIG. 5A: Fluorescence in mouse cerebral cortex after i.v. injection of albumin-FITC (non-encapsulated)
Figure 5B:
FIG. 5B: Fluorescence in mouse cerebral cortex after i.v. injection of albumin-FITC encapsulated in GLH-20 vesicles.
Figure 6A:
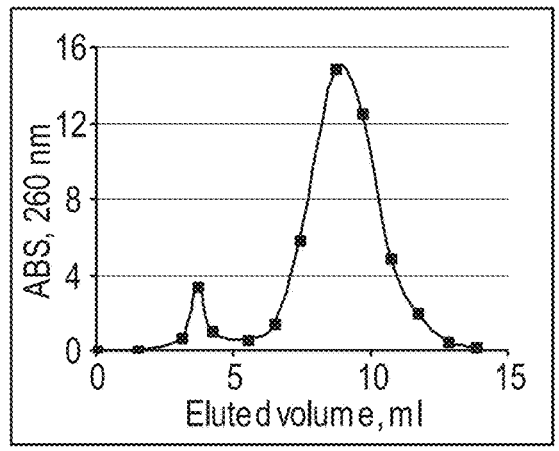
FIG. 6A: The effect of the stearyl amine on tenofovir encapsulation measured at a bola concentration of 15 mg/ml in vesicles not containing stearyl amine
Figure 6B:
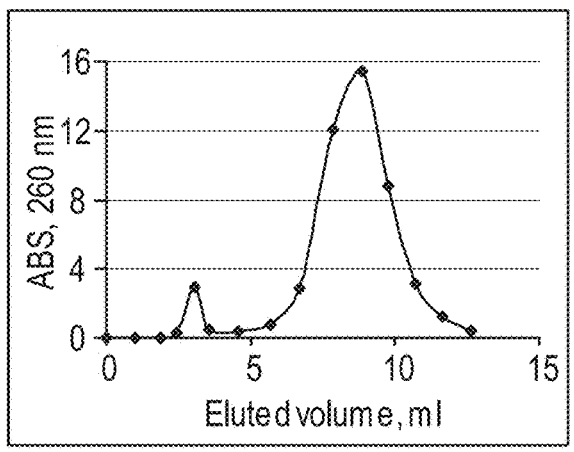
FIG. 6B: the effect of stearyl amine on tenofovir encapsulation measured at a bola concentration of 10 mg/ml in vesicles not containing stearyl amine
Figure 6C:
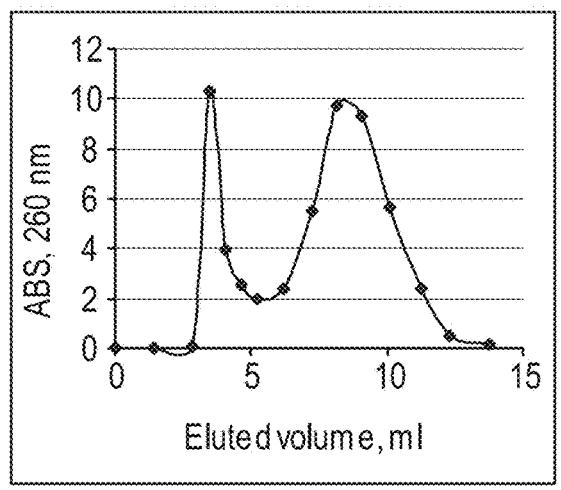
FIG. 6C: the effect of stearyl amine on tenofovir encapsulation measured at a bola concentration of 15 mg/ml in vescicles containing 2.5 mg/ml stearyl amine.
Figure 6D:
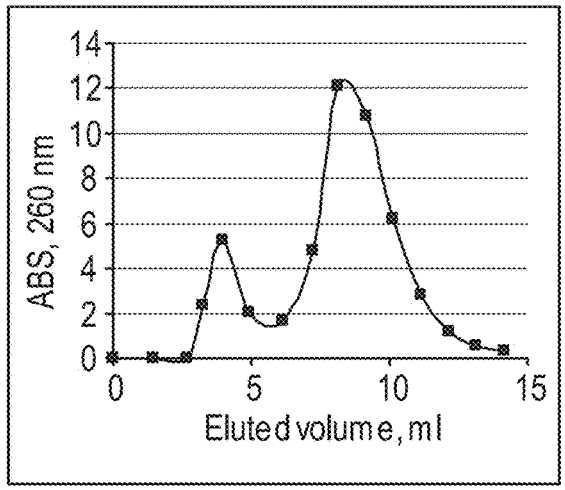
FIG. 6D: the effect of stearyl amine on tenofovir encapsulation measured at a bola concentration of 10 mg/ml in vesicles containing 2.5 mg/ml stearyl amine. Tenofovir is dissolved in HEPES in the concentration of 5 mg/ml

In addition to the peptide leu-enkephalin, and the small molecules: CF, uranyl acetate, kyotorphin and sucrose, can also be successfully encapsulated in these vesicles the proteins albumin and trypsinogen and the polysaccharide Dextran-FITC (MW 9000). Albumin-FITC, encapsulated, was delivered successfully to the brain (FIG. 5B), while un-encapsulated albumin-FITC showed little, if any, brain accumulation (FIG. 5A), indicating that the vesicle transported the protein into the brain through the BBB. These results strongly suggest that the vesicles can be made to encapsulate other molecules, such as anti-retroviral drugs, and deliver them into the brain without harming the BBB.

Example 8

Statistical Analysis

The data are presented as mean and standard deviations (SD) or standard errors of mean (SEM). Statistical differences between the control and the studied formulations are analyzed using ANOVA followed by Dunnett post-test using InStat 3.0 software (GraphPad Software Inc., La Jolla, Calif., USA). P values of less than 0.05 are defined as statistically significant.

Example 9

Delivery of Tenofovir to the Brain by Novel Nanovesicles for the Treatment of Neuro-HIV In another embodiment, the present disclosure is directed to is to development of a vehicle for the delivery of therapeutic agents into the brain. In one aspect of this embodiment, the agent is tenofovir. The Examples below describe the synthesis of a bolaamphiphile with a long hydrophobic domain and a CS head group (GLH-55b), optimization of the tenofovir encapsulation in the vesicles described herein, evaluation of the BBB permeability of vesicles that contained GLH-55b in comparison to vesicles that contain GLH-55a, delineation of conditions for detection of tenofovir in the brain and the concentrations of tenofovir in the brain following intravenous administration of optimized vesicles with encapsulated tenofovir.

Synthesis of GLH-55b

This compound was prepared as part of an effort to further increase the BBB permeability of the vesicles described herein. It is a bolaamphiphile with a CS head group GLH-55b, in which the aliphatic chain has 33 carbon atoms.

Synthesis of the Bolaamphiphile's Skeleton

The synthesis of the asymmetrical skeleton (Scheme 1) of GLH-55b was carried out through transesterification of methyl vernolate with aliphatic diols using *Candida antarctica* lipase, immobilized on acrylic resin as the catalyst, to obtain the corresponding mono-hydroxy ester of vernolic acid. This compound was further reacted with a protected dicarboxylic acid prepared as described in Scheme 2.

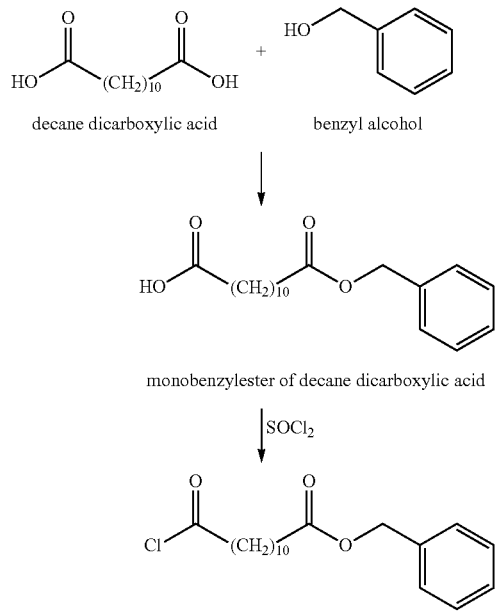

To obtain the monobenzyl ester described in Scheme 2, the dioic acid was reacted with benzyl alcohol using a ratio of 1:0.6 in toluene under azeotropic conditions, in the presence of catalytic amount of $H_2SO_4$. The unreacted dicarboxylic acid was precipitated from the reaction mixture at room temperature and the product was recrystallized from hexane.

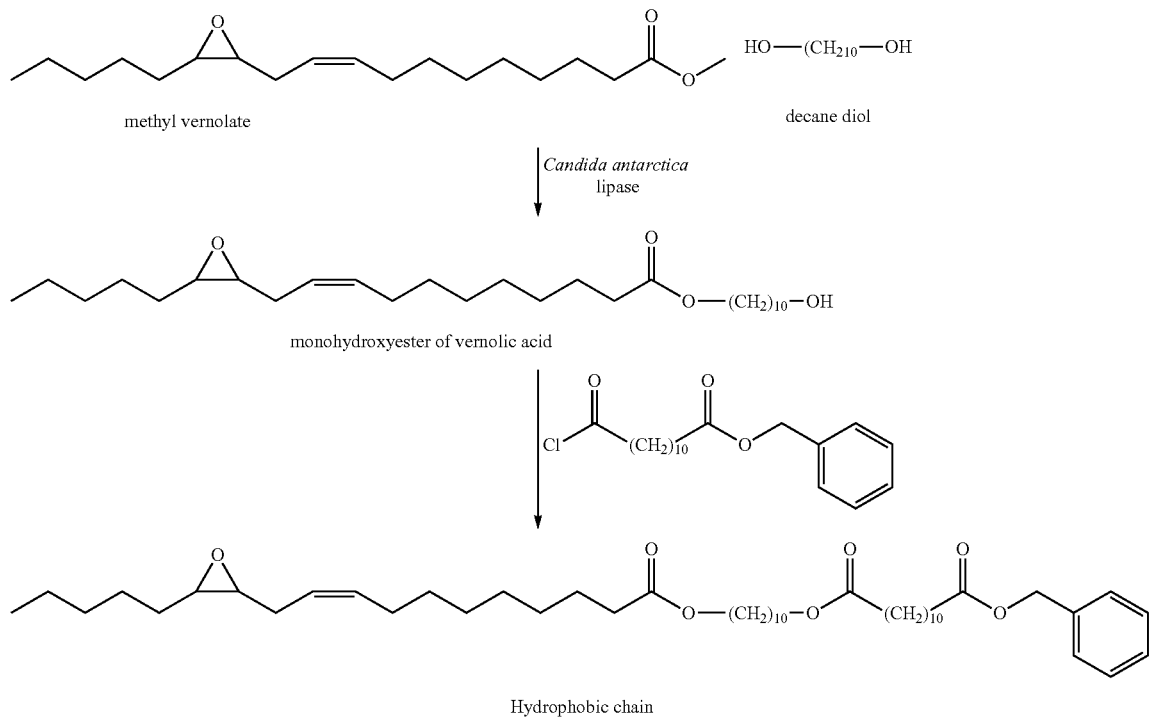

The monobenzyl ester was reacted with thionyl chloride to form the reactive acyl chloride that was subsequently reacted with the monohydroxy vernolate ester in presence of an excess of triethylamine. To avoid epoxide decomposition, the reaction was carried out in dichloromethane at −10° C. The crude product was separated by flash chromatography to give the pure hydrophobic skeleton. ESI-MS Calculated for $C_{47}H_{78}O_7$:754.57. Found: 755.2 [M+H$^+$], 777.2 [M+Na$^+$], 793.1 [M+K$^+$].

Attachment of the Head Groups

The two different head groups—CS and ACh—were attached to the long hydrophobic skeleton (about 32-33 atoms) that was obtained as described in Scheme 1. The attachment of these head groups to the bolaamphiphile's skeleton is described in Scheme 3

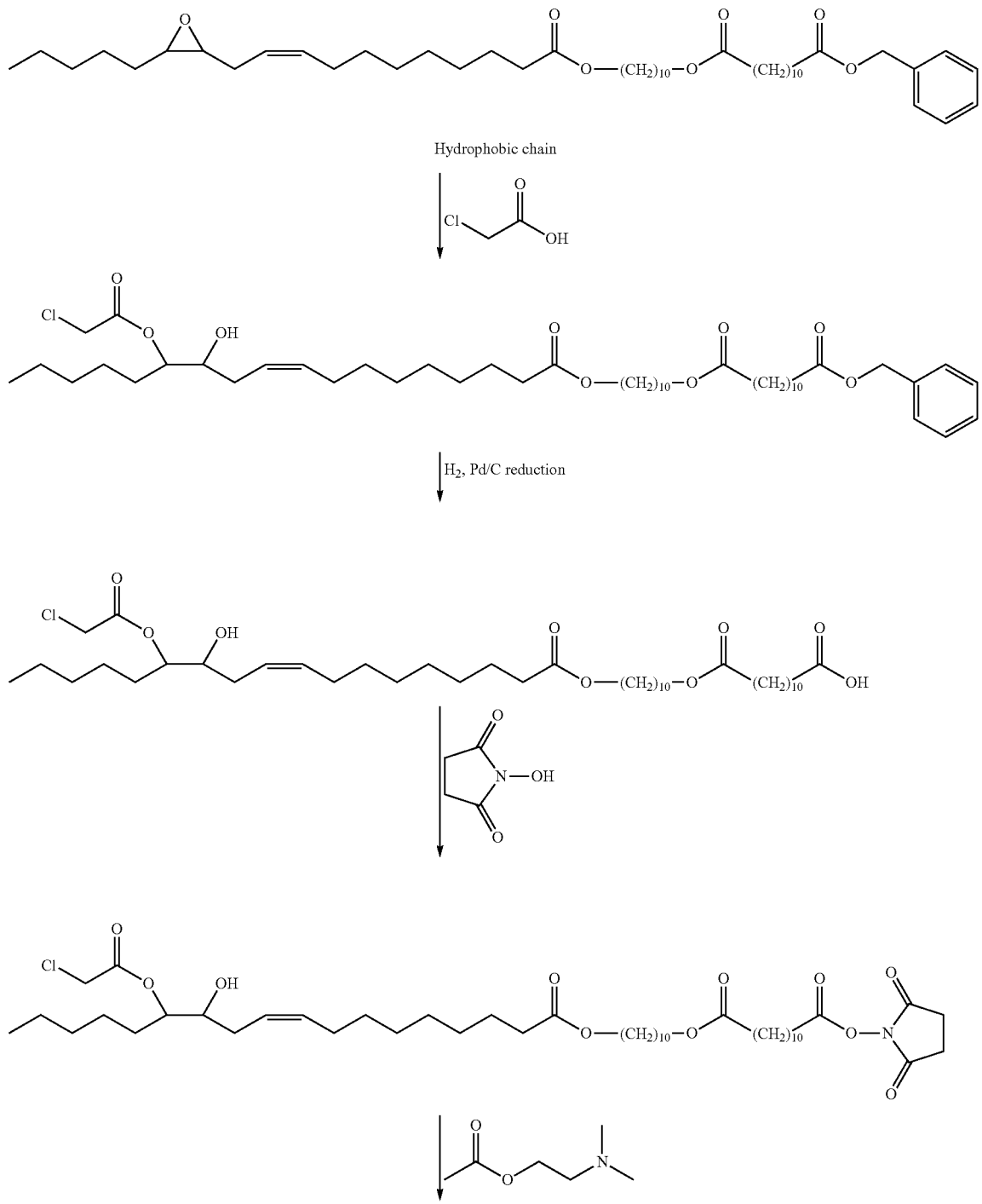

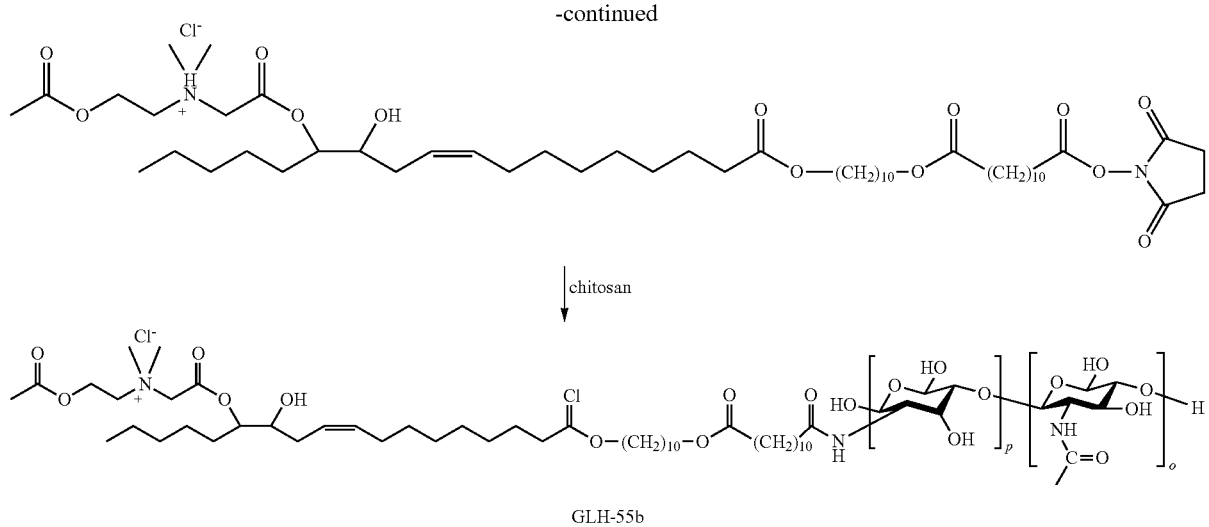

GLH-55b ring. Opening the epoxy ring gave the chloroacetyl group at one of the carbons of the original epoxy ring and an adjacent hydroxyl group at the second carbon of the epoxide. The reaction was performed with a slight excess of chloroacetic acid, at 100° C. for about 12 h. The solvent was removed under reduced pressure and the residue washed with water to remove the excess of the chloroacetic acid. The crude product was purified by flash chromatography with a mixture of hexane and ethyl acetate as the eluent.

ESI-MS: Calculated for $C_{49}H_{81}ClO_9$: 848.56. Found: 871.3 [M+Na$^+$], 887.1 [M+K$^+$], 731.0 [M+H$^+$—H$_2$O].

The next step was the removal of the benzyl group by hydrogenation in a Parr Shaker type hydrogenator. The deprotection of the long chain ester, which was obtained in the previous steps, was performed with hydrogen in the presence of Pd/C in ethyl acetate as the solvent under pressure of 40 psi at room temperature for 2 h. In the FT-IR spectrum it was possible to detect disappearance of the absorption band characteristic of the aromatic ring at 699 cm$^{-1}$ and the appearance of the absorption band at 1706 cm$^{-1}$, which is characteristic of the carboxylic acid.

The long chain ester, with carboxylic acid at one end was transformed into an activated acid ester by reacting it with N-hydroxysuccinimide. The new ester has now a good leaving group that can react with amines to form amides. The formation of the long chain activated N-hydroxysuccinimide ester was performed in the presence of dicyclohexylcarbodiimide (DCC) at room temperature. The separation of the product from the reaction mixture was difficult and therefore a second column separation was included. After purification on the second column, HPLC showed that the product is essentially 100% pure. ESI-MS Calculated for $C_{46}H_{80}ClNO_{11}$:880.6. Found: 880.6 [M+Na$^+$], 896.5 [M+K$^+$].

The next stage was the attachment of the ACh head group. The intermediate obtained in the last stage having the chloro acetate group at one end and the N-hydroxysuccinimide ester at the other end was reacted with an excess of N,N-diethylaminoethylacetate (that served as the solvent also) at 40-45° C. under nitrogen for about 7 h. The excess of N,N-diethylaminoethylacetate was removed by repeated additions of dichloromethane. Argentometric titration of the chloride ion of the quaternary compound gave Cl$^-$ 3.14% when the theoretical value was 3.59%, that means that according to Cl$^-$ the purity was 87.6%.

The last stage in the synthesis of GLH-55b is the attachment of the low molecular weight chitosan (LMWCS) to the bolaamphiphilic skeleton that now contains ACh head group on one side of the aliphatic chain and an acylating group (N-hydroxysuccinimide ester) at the other end. This conjugation was performed by adding a solution of the intermediate compound described above in DMSO to a solution of the LMWCS and triethylamine in DMSO. The molar ratio of the LMWCS to the intermediate compound with the activated ester was 10:1. The reaction mixture was stirred for about 70 h at room temperature. The triethylamine was removed under reduced pressure and the solution was lyophilized to give a yellow powder.

FT-IR of the product showed that in addition to the absorption peaks characteristic of the LMWCS, new absorption peaks characteristic of ester, amide and acetate groups at 1739, 1563 and 1241 cm$^{-1}$ were observed. The purity of the bolaamphiphilic product was 75% as determined by argentometric titration of the chloride ion. Additional purification was necessary to get a purer product.

Optimization of Tenofovir Encapsulation

Methods were established to determine quantitatively the amount of the encapsulated tenofovir based on a UV absorption and determined the percent of tenofovir encapsulation by various vesicle formulations (data not shown). Under the conditions that yielded maximum amounts of tenofovir encapsulation, about 18-20% encapsulation was observed. One objective of this work was to achieve the maximum amount of tenofovir encapsulated per vesicle along with a minimum loss of the non-encapsulated drug. Accordingly, several parameters were examined, such as varying the ratio among the vesicle components, changing the ratio of tenofovir to bolaamphiphiles, varying the pH of the hydration solution and also adding to the formulation additional additives, in the attempt to increase the encapsulation capacity of the vesicles.

In particular, in order to maximize tenofovir encapsulation the following parameters were studied: (1) tenofovir to GLH ratio; (2) adjusting the concentrations of cholestyrl hemisuccinate (CHEM) and cholesterol (CHOL), components that are used in the vesicle formulation, (3) examining several buffers and pHs in the encapsulation process, (4)

time of sonication, and (5) tenofovir concentration, and (6) addition of stearyl amine to the vesicle formulation to enhance encapsulation by complexation with tenofovir.

The results of the Optimization of tenofovir encapsulation, are presented below in Table 2:

TABLE 2

The effect of the concentration of bolaamphiphiles and tenofovir as well as of the buffer and pH on % tenofovir encapsulation in vesicles

| Buffer and pH of solution | GLH 19/20 (2:1)* mg/ml | % tenofovir encapsulation per tenofovir concentration in hydration solution, mg/ml | | | |
|---|---|---|---|---|---|
| | | 1 mg/ml | 2 mg/ml | 5 mg/ml | 7.5 mg/ml |
| TRIS pH 8 | 5 | 4 | | | |
| TRIS pH 8 | 10 | 11 | 9 | 6 | |
| TRIS pH 8 | 15 | 24.5 ± 2.1 | 21 ± 2.1 | 9 ± 1.4 | |
| TRIS pH 8 | 20 | 31.4 ± 4.5 | 22.5 ± 3.5 | 9.3 | |
| HEPES pH 7.5 | 10 | 17.4 | **16.5 | 7.8 | 3.8 |
| HEPES pH 7.5 | 15 | 38.6 | 18.4, **22.5 | | |
| HEPES pH 8 | 15 | 31.2 | | | |

*the standard amount of cholesterol/cholesteryl hemisuccinate is 1.6 mg/2.4 mg per 10 mg of the GLH; and
**Value for a formulation with ½ the standard amount of cholesterol and cholesteryl hemisuccinate.

Note that The numbers in the last 4 columns of Table 2 represent percent tenofovir encapsulation±SEM;

As can be seen from Table 2, a formulation that contained 15 mg bolaamphiphiles and 1 mg tenofovir in HEPES buffer pH 7.5 gave the highest percent encapsulation (38.6%). The data of Table 2 indicated that in order to get maximum amount of encapsulated tenofovir per bolaamphiphiles, it could be advantageous to use more tenofovir per bolaamphiphile. Maximum encapsulation was obtained at a ratio of encapsulated tenofovir to bolaamphiphile of 0.039 (Table 3, below). This further suggested that, in order to inject 10 mg/kg of tenofovir it would be necessary to co-inject 256 mg/kg of GLH. In order to avoid this relatively high level of bolaamphiphile, conditions were sought that would allow the ratio of encapsulated tenofovir per mg of bolaamphiphiles to exceed 0.039 (the ratio that had given the maximum encapsulation, as noted above). The values in Table 3, below were calculated from the values presented in Table 2, above

TABLE 3

Ratio of encapsulated tenofovir to bolaamphiphiles

| Buffer and pH of solution | GLH 19/20 (2:1)*, mg/ml | mg tenofovir encapsulated/mg bola per Tenofovir concentration in the hydration solution, mg/ml. | | |
|---|---|---|---|---|
| | | 1 mg/ml | 2 mg/ml | 5 mg/ml |
| TRIS pH 8 | 5 | 0.008 | | |
| TRIS pH 8 | 10 | 0.011 | 0.018 | 0.03 |
| TRIS pH 8 | 15 | 0.016 | 0.03 | 0.03 |
| TRIS pH 8 | 20 | 0.02 | 0.022 | 0.023 |
| HEPES pH 7.5 | 10 | 0.026 | 0.024 **0.033 | |
| HEPES pH 7.5 | 15 | 0.026 | **0.033 | 0.039 |
| HEPES pH 8 | 15 | 0.021 | | |

*The standard amount of cholesterol/cholesteryl hemisuccinate is 1.6 mg/2.4 mg per 10 mg of the GLH.
**Value for a formulation with ½ the standard amount of cholesterol and cholesteryl hemisuccinate.

The numbers in the 3 last columns of Table 3 represent ratios of mg tenofovir encapsulated mg bolaamphiphile.

In an attempt to increase tenofovir encapsulation, stearyl amine was added to determine if that would increase tenofovir encapsulation. The data of FIG. 6, depicts the effect of stearyl amine (SA) on tenofovir encapsulation. The vesicles were prepared from formulations with and without SA and the non-encapsulated tenofovir (free tenofovir) was separated from the encapsulated tenofovir on Sephadex G50 column and the absorbance at 260 nm of each fraction collected from the column was read.

As can be seen from FIG. 6, the peak of the encapsulated tenofovir precedes the peak of the free tenofovir and a progressive reduction in the non encapsulated tenofovir along with an increase in peak of the encapsulated tenofovir is apparent in vesicles made from formulations that contained SA, suggesting SA increase tenofovir encapsulation in the vesicles prepared herein. Notably, the peak of a free tenofovir, without vesicles, that was run on the column remains constant.

Since SA increased tenofovir encapsulation, the optimal concentration of SA that gives maximum tenofovir encapsulation without jeopardizing vesicles stability was examined. In these experiments 5 mg/ml tenofovir was used, and two different concentrations of bolaamphiphiles—10 mg/ml and 15 mg/ml GLH19/GLH20 (2:1) and the cholesterol/cholesteryl hemisuccinate were in the same concentrations as given in Table 3 above. In addition, Tris buffer to HEPES buffer were compared, with respect to tenofovir encapsulation. The results are shown in Table 4.

TABLE 4

Effect of stearyl amine (SA) on tenofovir encapsulation in vesicles

| Buffer and pH of solution | GLH 19/20 (2:1)*, mg/ml | SA, mg/ml | % tenofovir encapsulation | Ratio of tenofovir encapsulated to bolaamphiphiles (mg/mg) |
|---|---|---|---|---|
| TRIS pH 8 | 10 | 2.5 | 12.7 | 0.064 |
| HEPES pH 7.5 | 10 | 2.5 | **22 | **0.11 |
| | | | 21.4 | 0.107 |
| HEPES pH 7.5 | 15 | 2.5 | 18.6 | 0.08 |
| HEPES pH 7.5 | 10 | 1.25 | 15.9 | 0.062 |
| HEPES pH 7.5 | 10 | 3.5 | 30.9 | 0.155 |
| HEPES pH 8 | 15 | 2.5 | 23 | 0.077 |

*The standard amount of cholesterol/cholesteryl hemisuccinate is 1.6 mg/2.4 mg per 10 mg of the GLH.
**Value for a formulation with ½ the standard amount of cholesterol and cholesteryl hemisuccinate used in Table 3.

The numbers in the last column of Table represent ratios of mg tenofovir encapsulated/mg bolaamphiphile.

It was found that 2.5 mg/ml stearyl amine effectively increases tenofovir/GLH ratio and the resulting vesicles were stable in a transparent clear solutions, not precipitating with time. The results shown in Table 4 show a significant improvement in the mg of tenofovir encapsulated per mg of GLH bola. Thus, in comparison to the results shown in Table 3, the ratio of the encapsulated tenofovir to the bolaamphiphiles has been increased from 0.039 to 0.11 and even to 0.155. Formulations that provided the higher ratio of 0.155 provided turbid vesicle solutions in which the vesicle precipitated with time. In addition the results of Table 4 show that HEPES buffer gives better results in comparison with the Tris buffer. The data of Table 4, suggest, e.g., the usitility of a formulation constituted 10 mg/ml bolaamphiphiles with 2.5 mg/ml SA and HEPES buffer.

Vesicles were prepared from the optimal formulation shown in Table 4 with the addition of the GLH-55b, for use in the PK studies. Addition of the CS-bolaamphiphile, GLH-55b, did not affect tenofovir encapsulation, nor their size and their zeta potential of those vesicle (Table 5).

TABLE 5

Size and surface charge of vesicles prepared from the indicated formulations

| Vesicle formulations contained 10 mg/ml GLH19 + 20(2:1) and standard concentrations of cholesterol and cholesteryl hemisuccinate | Radius in nm determined by DLS | Zeta potential, mV |
|---|---|---|
| Empty vesicles | 57.19 ± 1.14 | 56.9 ± 2.64 |
| Tenofovir-loaded vesicles with SA | 58.37 ± 1.01 | 47.3 ± 1.31 |
| Tenofovir-loaded vesicles with SA and CS (GLH-55b) | 59.17 ± 1.1 | 50.2 ± 0.834 |

Encapsulation may be further improved (without having vesicle precipitation), by reducing vesicle aggregation, e.g., by: (1) increasing the degree of tenofovir complexation with the bolaamphiphilic head groups by lowering further the anionic additives (cholesteryl hemisuccinate); (2) additional time of sonication; (3) the introduction of extrusion or freeze thaw cycles after the sonication steps, and, possibly (4) post loading empty vesicles by a pH gradient across the vesicles.

Ex Vivo and In Vivo Characterization

The Effect of CS Surface Groups on BBB Permeability of Vesicles

Figure 7:
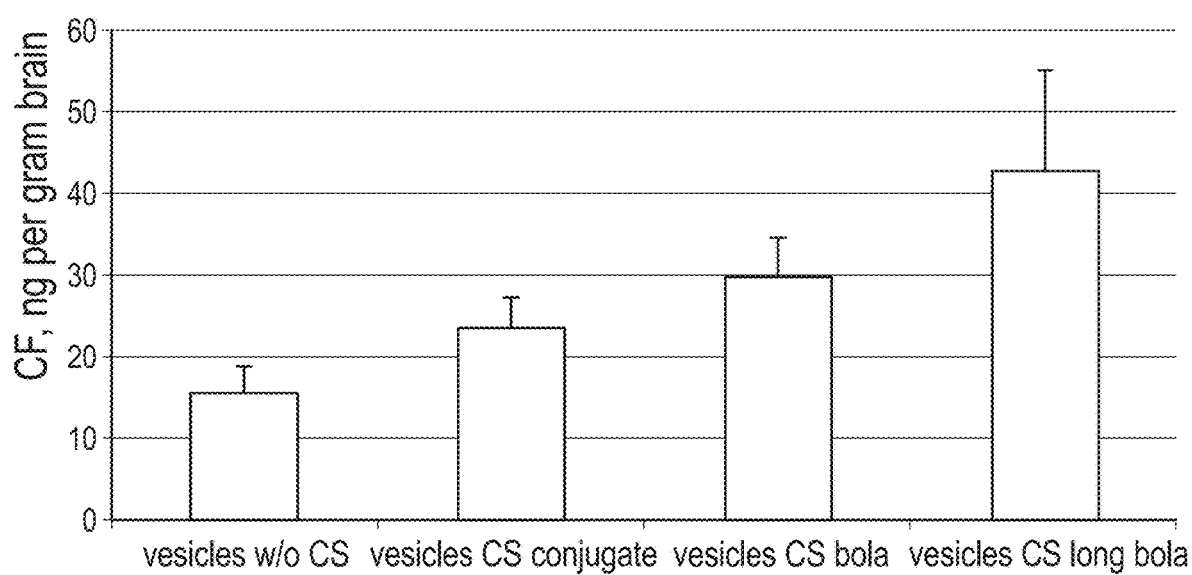
FIG. 7: Accumulation of CF in the brain after injecting the dye encapsulated in naked vesicles (vesicles w/o CS), or in vesicles that contain CS-vernolate conjugate, or in vesicles that contain GLH-55a (vesicles CS bola), or in vesicles that contain GLH-55b (vesicles CS long bola). CF-encapsulated vesicles were injected i.v. into mice and 30 min afterward animals were sacrificed, brain removed, homogenized, deproteinized by trichloroacetic acid and fluorescence was determined in the supernatants obtained by centrifugation after adjusting the pH to 7.0.

Comparison of a bolaamphiphile with the CS head group and a long aliphatic chain (GLH-55b) to a bolaamphiphile with the CS head group and a short aliphatic chain (GLH-55a), was canoed out by evaluating the ability of vesicles that contain each of these bolaamphiphile to transport carboxyfluorescein (CF) into the brain via the BBB. CF was encapsulated in vesicles made from formulations that contained only GLH-19 and GLH-20 (vesicles wCS), vesicles that contained CS groups incorporated by CS-vernolate conjugate and vesicles that contain either GLH-55a (vesicles CS bola) or GLH-55b (vesicles CS long bola) and injected them i.v. into the tail vein of mice. Thirty minutes afterward, the animals we sacrificed and the amount of the CF present in the brain was measured. The results are shown in FIG. 7. As can be seen in that figure, the highest amount of CF was accumulated in the brain of mice that received vesicles that contain the bolaamphiphile with CS head group and a long aliphatic chain (GLH-55b), suggesting that these vesicles contained more CS head groups on their surface.

Determination of Tenofovir in the Brain

As demonstrated above, the vesicles described herein are capable of transporting encapsulated material into the brain. Accordingly, the ability of those vesicles to transport encapsulated tenofovir into the brain and to determine the concentrations of the transported tenofovir in the brain at various times after the administration were examined. For this purpose an analytical method was required that would be capable of detecting tenofovir in brain homogenates at concentrations similar to those found in the blood after orally treating human subjects with 300 mg tenofovir, a dose that was shown to be effective against HIV. The blood concentration of tenofovir after treating human subjects with 300 mg tenofovir is about 500 ng/ml. Consequently, there was a need for a method for the determination of tenofovir in brain homogenate at the relevant concentrations. Initial studies led to a method based on HPLC combined with a UV detector sensitive enough to detect tenofovir at concentrations in the range of 500 ng/ml. Notably, the determination of tenofovir concentration by this method was done with solutions of tenofovir in aqueous media that contained only a buffer. This method has been refined and to detection of tenofovir spiked into brain homogenates.

Figure 8:
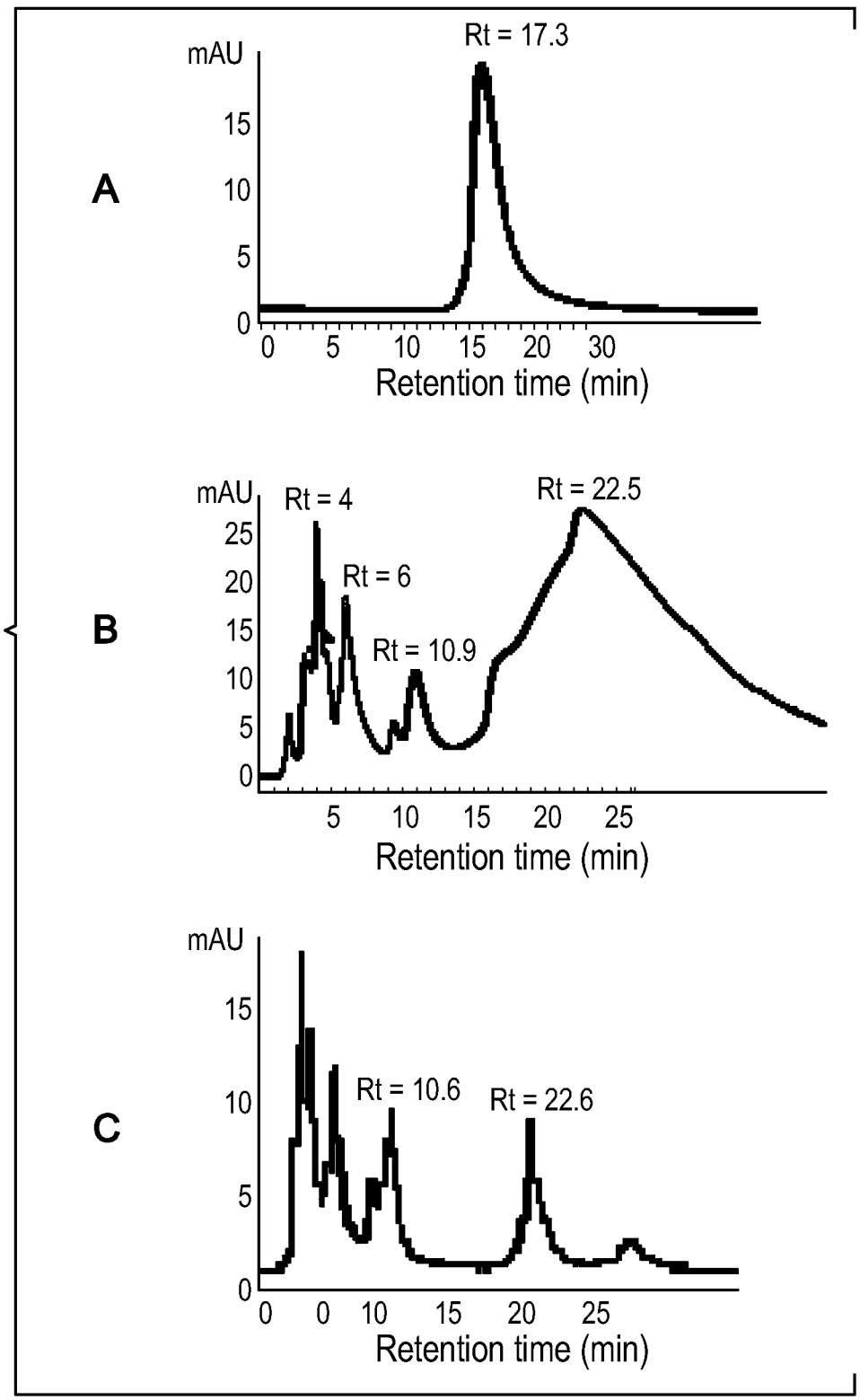
FIG. 8: Chromoatogram of tenofovir (Panel A), Chromatogram of supernatant obtained from a brain homogenate followed by deproteinization with TCA (Panel B), Chromatogram of and supernatant as in B after SPE treatment (Panel C).

Protein precipitation was accomplished by adding trichloroacetic acid (TCA) at a final concentration of 3.75%, providing a clear supernatant by centrifugation. This supernatant was neutralized by 1% sodium hydroxide solution and the neutralized extract was examined by HPLC with a UV detector, using an isocratic method with 10% acetonitrile and 90% buffer of triethyl amine in water adjusted to pH 5.4 with concentrated phosphoric acid. When applied to a solution of tenofovir in buffer without the brain extract, the retention time was 17.3 min (FIG. 8 Panel A). However, when applied to a supernatant of the brain homogenate after removal of the proteins with TCA, without tenofovir, various peaks were observed with different retention times (Rt) between 2.5-23 minutes. The broad peak at 22.5 min overlapped the peak of the tenofovir at 17 min (compare FIG. 8 Panel B to FIG. 8 Panel A) and would interfere with the determination of tenofovir concentration in the extract. To narrow the peak of the endogenous compound with the Rt of 22.5 min, a solid phase extraction (SPE) method was employed, using BOND ELUT-C18 column. After the treatment with SPE some peaks disappeared and the others became narrower. Under the isocratic conditions consisting of 0.3% acetonitrile and 0.1% acetic acid in water, the retention time of Tenofovir was about 17 minutes and the chromatogram of the supernatant after SPE treatment showed no peaks in this part (FIG. 8 Panel C).

Figure 9:
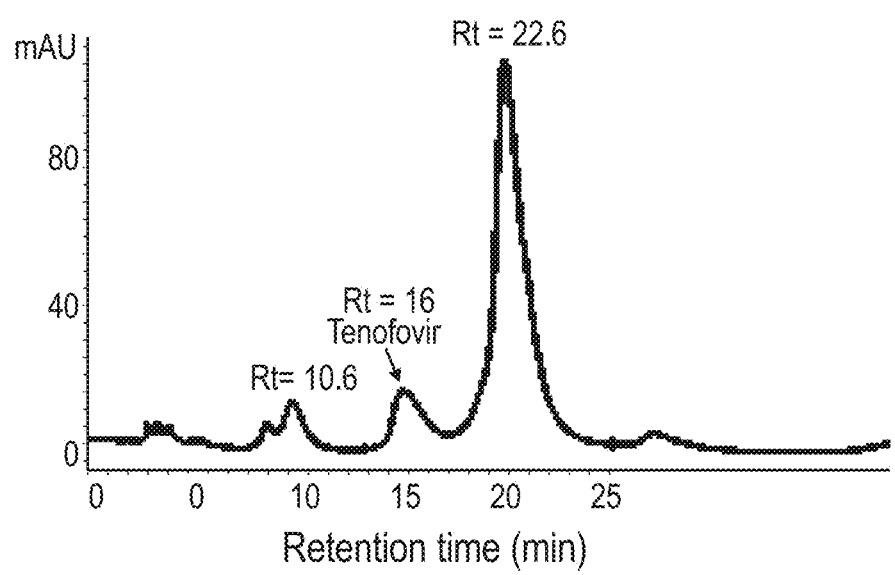
FIG. 9: Chromatogram of the supernatant containing 40 μg tenofovir after SPE treatment.

Under these conditions, tenofovir was well separated from the endogenous peaks and it showed an isolated measurable peak, as illustrated in FIG. 9).

As demonstrated above, conditions for the determination of tenofovir concentrations in brain extract had been established. Different concentrations of tenofovir were then spiked into a supernatant obtained after deproteinization of brain homogenate with TCA and centrifugation. The supernatant with the tenofovir was loaded into the SPE cartridge, which was conditioned by 3 ml methanol and 3 ml of 150 mM ammonium acetate (pH=5.0). After washing with 900 μl of 100 mM ammonium acetate (pH=7.0), in order to obtain less interference at the retention time of each component, the column was eluted by 500 μl of methanol to collect the tenofovir. The solvent was removed under nitrogen at 60° C. The extracted sample was dissolved into 120 μl of water and methanol solution (90:10, v/v) and injected into the HPLC. The data obtained are presented in FIG. 10.

Figure 10:
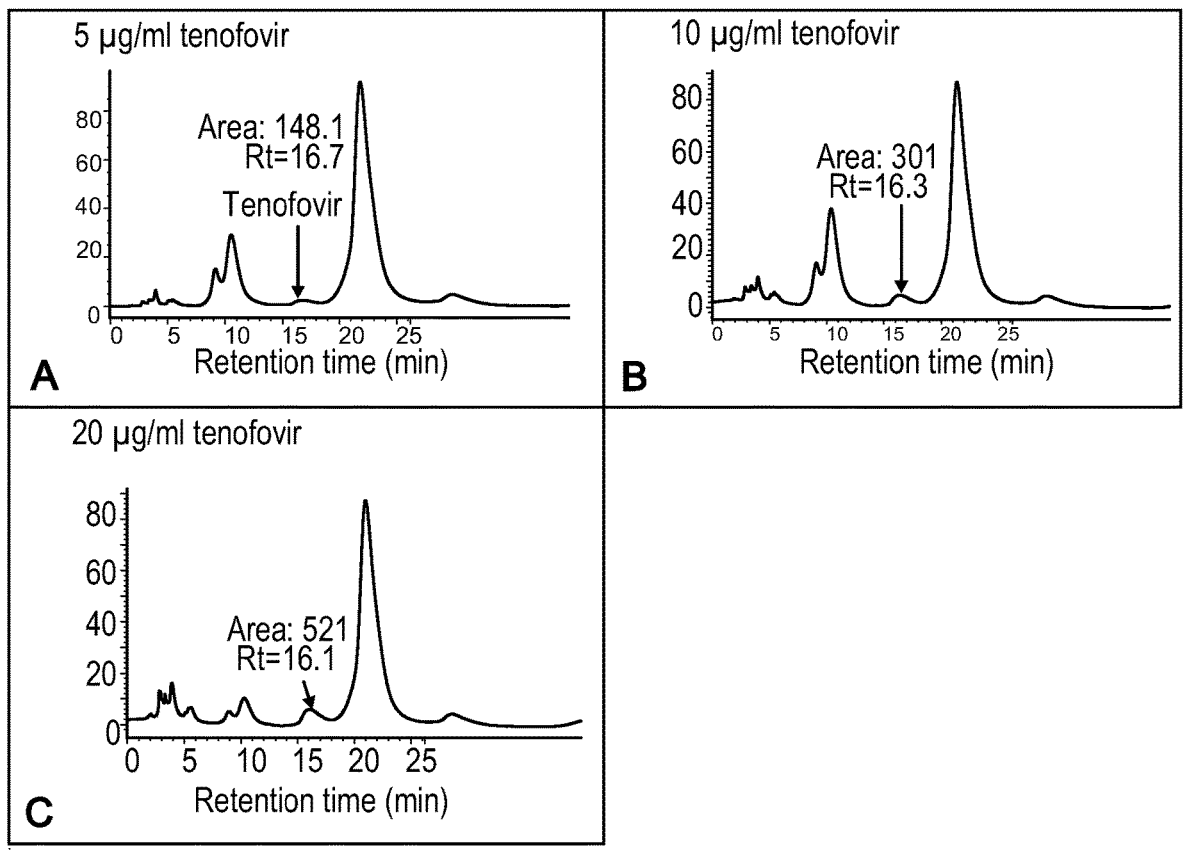
FIG. 10: Chromatogram of different concentrations of tenofovir, 5 μg/ml (Panel A), 10 μg/ml (Panel B), and 20 μg/ml (Panel C), in supernatant obtained after deproteinization of brain homogenate.
Figure 11:
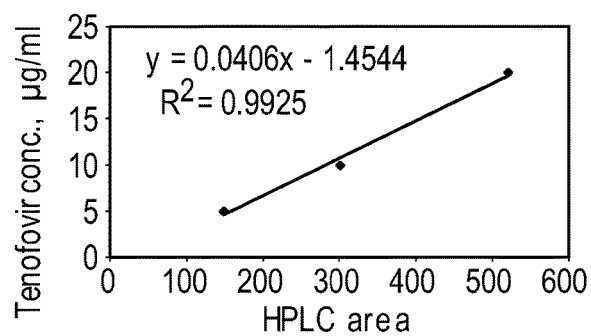
FIG. 11: A calibration curve of tenofovir in supernatant obtained from brain homogenate.
Figure 12:
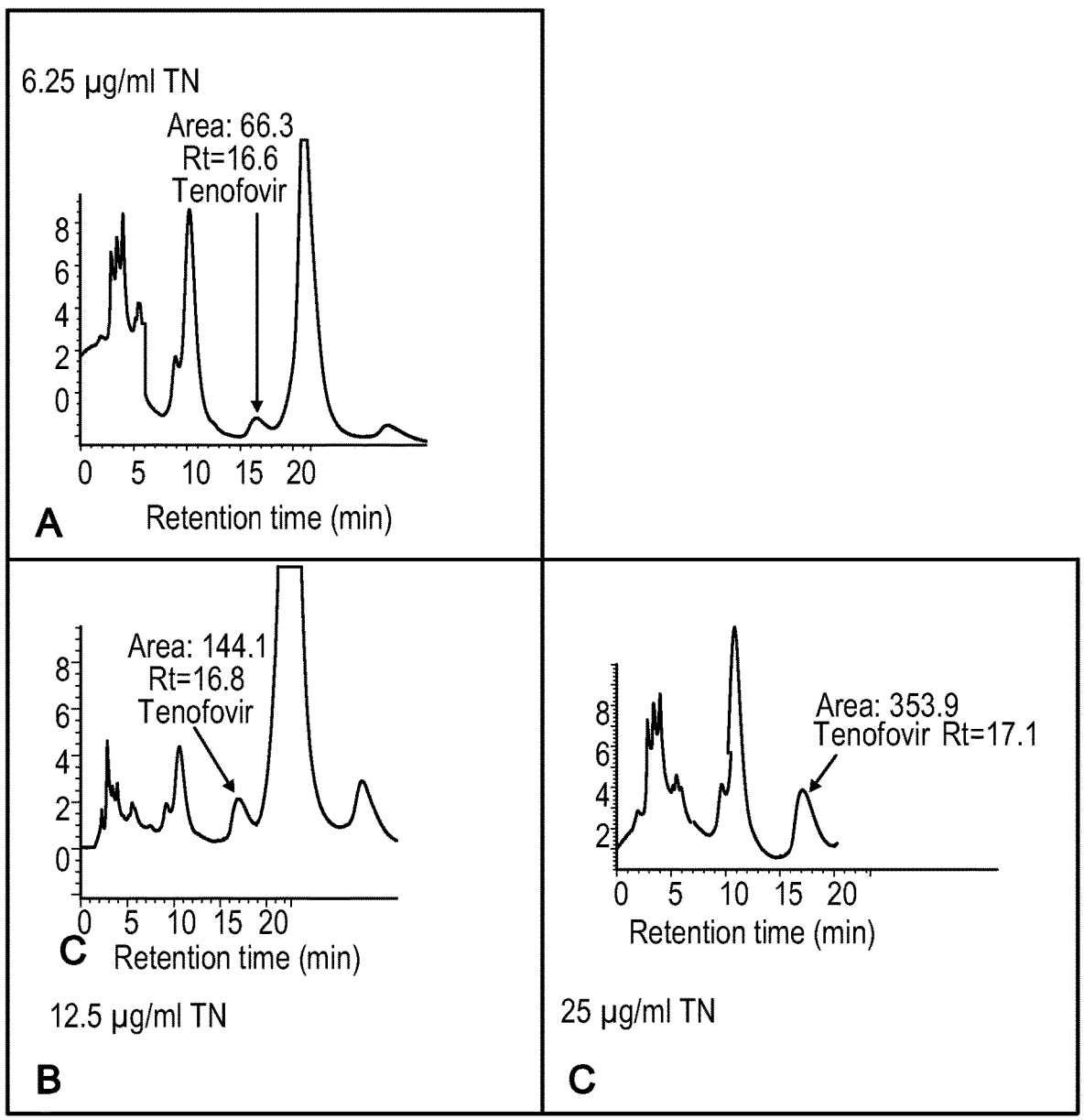
FIG. 12: Chromatogram of tenofovir spiked into brain homogenate at 6.25 μg/ml (Panel A), at 12.5 μg/ml (Panel B), and at 25 μg/ml (Panel C).

Calculation of the area under the peak of the tenofovir data of FIG. 10, allowed construction of the calibration curve set forth in FIG. 11, which showed a linear relationship between the tenofovir concentrations and the area under the peaks for these concentrations.

Figure 13:
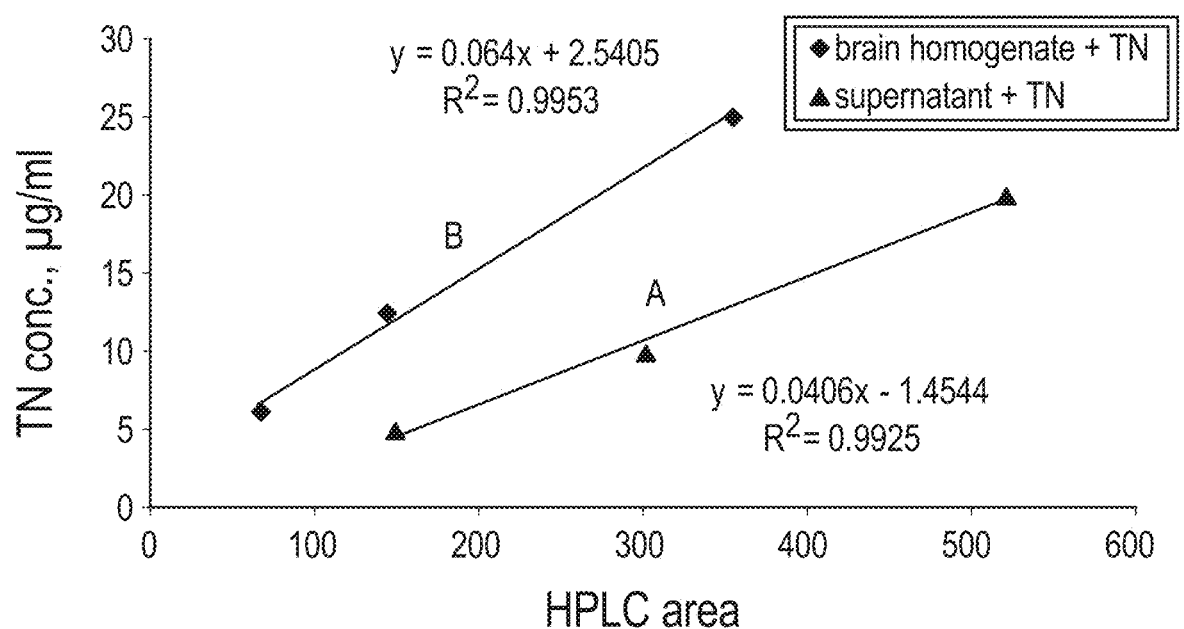
FIG. 13: Calibration curves of Tenofovir spiked into the supernatant obtained. from brain homogenate after removal of the proteins by TCA (A) and into brain homogenate (B).

The calibration curve obtained from the areas under the peaks in comparison to the areas under the peaks for the chromatogram of tenofovir that was spiked into brain extract obtained after precipitation of the proteins is shown in FIG. 13.

From these calibration curves it can be seen that lower amounts of tenofovir have been detected when Tenofovir was spiked into brain homogenate (FIG. 13, curve B) compared to samples in which the tenofovir was spiked into the supernatant obtained by deproteinization of the brain homogenate (FIG. 13, curve A). When the percent recovery of tenofovir was calculated for each concentration, it was found that for the lower tenofovir concentrations (6.25 and 12.5 μg/ml), the recovery was between 36-38% and for the highest concentration that was tested (25 μg/ml), the recovery was 54% (Table 6). These data indicated that a calibration curve will have to be done after knowing the concentration range that was found in the brain according to the areas under the peaks that will be obtained from homogenates of brains taken from animals that were injected with tenofovir-loaded vesicles.

TABLE 6

Percent recovery of tenofoivir from brain homogenates

| Tenofovir conc. (μg/ml) | Area under the peak | | Percent recovery |
|---|---|---|---|
| | A | B | |
| 6.25 | 185 | 66 | 35.7 |
| 12.50 | 376 | 144 | 38.3 |
| 25.00 | 651 | 353 | 54.2 |

A = tenofovir concentrations after spiking the drug into brain extract obtained after protein precipitation;
B = tenofovir concentrations after spiking the drug into brain homogenates The experiments above used higher concentrations of tenofovir than those expected to be found in the brain after delivering the drug encapsulated in vesicles. This was done in order to provide a clear signal to noise ratio during this, preliminary, developmental work. Lower concentrations of tenofovir concentrations can be detected using with the HPLC method described herein or methods employing LC-MS. However, the assay described herein, using higher concentrations of tenofovir, as useful detecting tenofovir in the brain after injecting mice i.v. with tenofovir-loaded vesicles.

Determination of Tenofovir Concentrations in the Brain after Injecting Animals with Tenofovir-Loaded Vesicles.

Figure 14A:
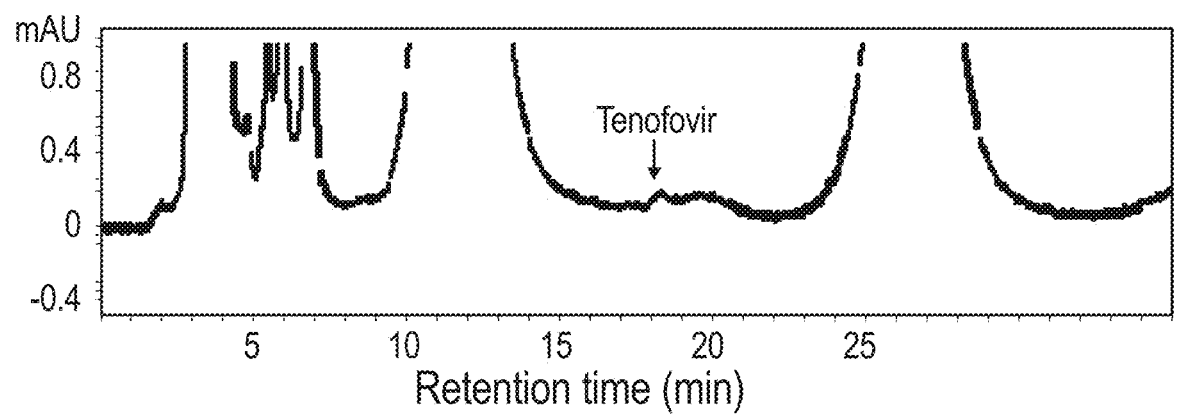
FIG. 14A: Chromatogram of brain extracts taken from a first animal injected with tenofovir-loaded V-Smart™ vesicles.
Figure 14B:
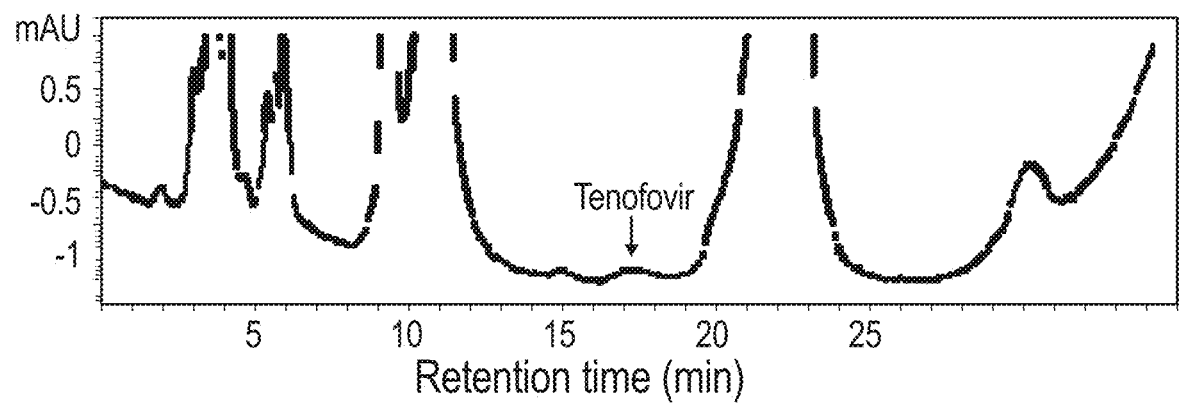
FIG. 14B: Chromatogram of brain extracts taken from a second animal injected with tenofovir-loaded V-Smart™ vesicles.
Figure 14C:
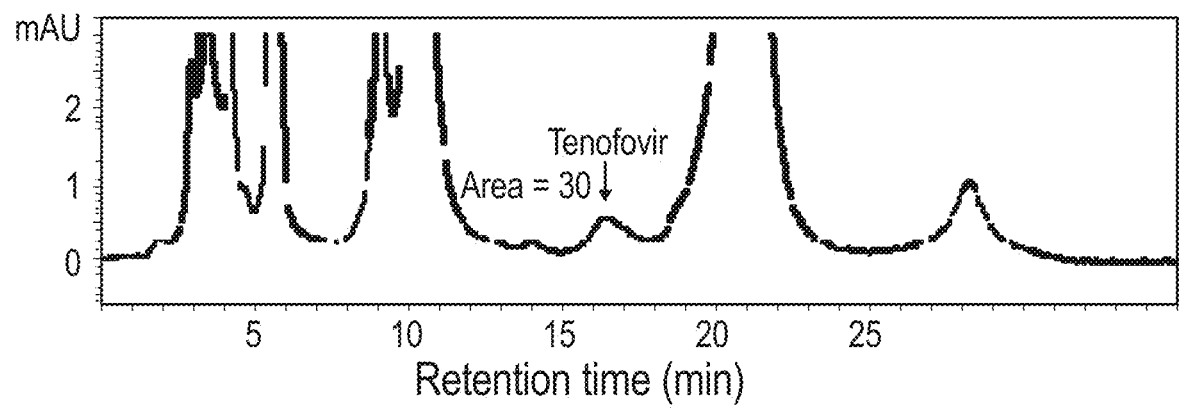
FIG. 14C: Chromatogram of brain extracts taken from a third animal injected with tenofovir-loaded V-Smart™ vesicles.
Figure 15:
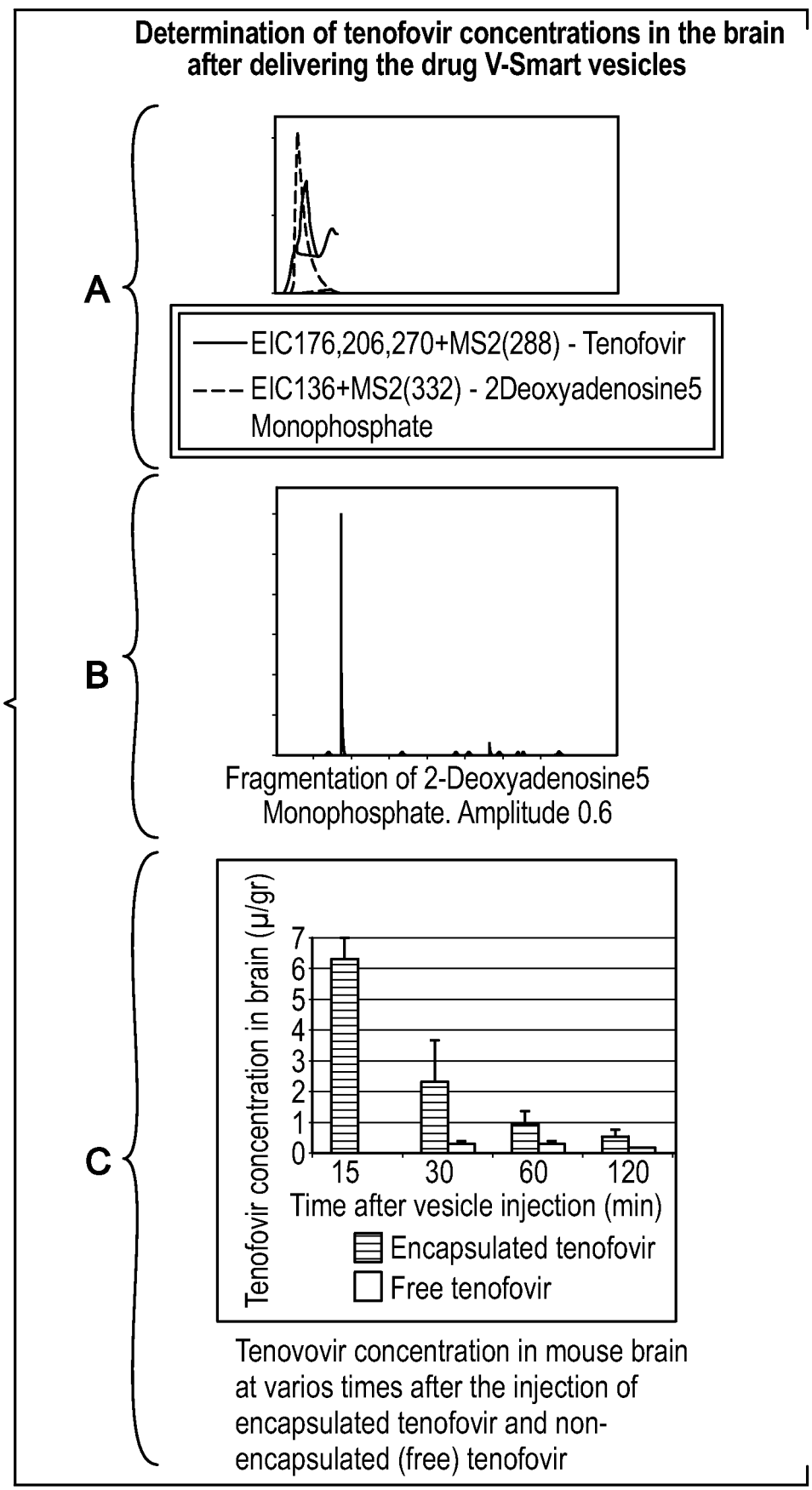
FIG. 15: Determination of tenofovir concentrations in the brain after delivery of the drug by vesicles of the disclosure: Determination of tenofovir concentration in the brain after delivery in V-Smart vesicles (Panel A); Fragmentation of 2-deoxyadenosine-5-monophosphate (Panel B); and tenofovir concentration in mouse brain after injection of encapsulated and non-encapsulated (free) tenofovir (Panel C).

In view of the conditions for the determination of tenofovir in brain homogenates established herein, mice were injected with 7.5 mg/kg of tenofovir encapsulated in vesicles prepared as for Table 5 above that contained the optimal GLH-55b and SA and brain homogenates were prepared from the brains of these mice for the determination of tenofovir concentrations. The chromatograms of the brain extracts from these mice showed peaks with retention times that correspond to tenofovir, as depicted in FIG. 14 C. The peaks in the chromatograms observed (FIG. 14 C). and using the lowest point of the calibration curves obtained for tenofovir spiked into brain homogenate (curve B in FIG. 13), it was estimated that the concentration of tenofovir in the brain of the animal that received 7.5 mg/kg encapsulated tenofovir to be 22.7 μg/gr brain. This concentration value is significant and should have a therapeutic affect against HIV.

A subsequent in vivo experiment was carried out as above but with testing over different periods of time from of 15 min, 30 min, 60 min and 120 min after IV injection the amount of tenofovir was in micro gr/grm brain 6.2, 2.2, 1.0 and 0.5 respectively. While the free tenofovir injected had levels of 0 less than 0.2 micrograms/gr brain. Thus indicating the efficacy of the vesicles to delivery tenofovir to the brain.

As described here a novel formulations of bolavesicles can be produced through co-assembly of HIV drugs with bolaamphiphile/lipid unilamellar vesicles. The formulations can be examined for their chemical and biophysical properties. In one embodiment the vesicles formed from the bolaamphiphiles by aggregation contain additives that help to stabilize the vesicles, by stabilizing the vesicle's membranes, such as but not limited to cholesterol derivatives such as cholesteryl hemisuccinate and cholesterol itself and combinations such as cholesteryl hemisuccinate and cholesterol. In still another embodiments the vesicles in addition to these components and the bolamphiphiles have another additives which decorates the outer vesicle membranes with groups or pendants that enhance penetration though biological barriers such as the BBB, or groups for targeting to specific sites. Further the bolaamphiphile head can interact with the active agents to be delivered such as tenofovir by ionic interactions to enhance the % encapsulation via complexation and well as passive encapsulation within the vesicles core. Further the formulation may contain other additives such as stearyl amine within the veicles membranes to further enhance the degree of encapsulation of active agents like tenofovir. To maximize the ionic interactions between the components to increase the efficiency of encapsulation the pH of the aqueous hydrating solutions can be optimized by well known methods of the state of art.

The incorporation of HIV drug within the bolavesicles is shown to significantly modulate interactions with membrane bilayers in model systems. This observation is important, suggesting that HIV drugs encapsulated in bolavesicles might be excellent candidates for targeting and transport of different molecular cargoes into the brain.

LC-MS Method for the Determination of Tenofovir in the Brain

The chromatographic separation was performed with an HPLC Agilent 1100 instrument and Auto-sampler G 1329A ALS 1200 Series with Frizzier G1330B FC/ALS Therm, at a temperature of 4° C., using a reverse phase Kromasile 100A C18 250×2.0 (5 μm) column at 30° C. under gradient conditions. The mobile phase consisted of two solvents: (A) acetonitrile and (B) 0.5% formic acid in water and was operated under the following conditions:

TABLE 7

| Time (min) | Percent Solvent A | Percent Solvent B |
|---|---|---|
| 0 | 10 | 90 |
| 7 | 10 | 90 |
| 12 | 100 | 0 |
| 15 | 100 | 0 |
| 22 | 10 | 99 |
| 30 | 10 | 90 |

The MS/MS detector was an Ion Trap MS Esquire 3000 Plus (Bruker Daltonics), operating in the ESI positive polarity mode. The internal standard was 2'-deoxyadenosine 5'-phosphate.

Figure 16A:
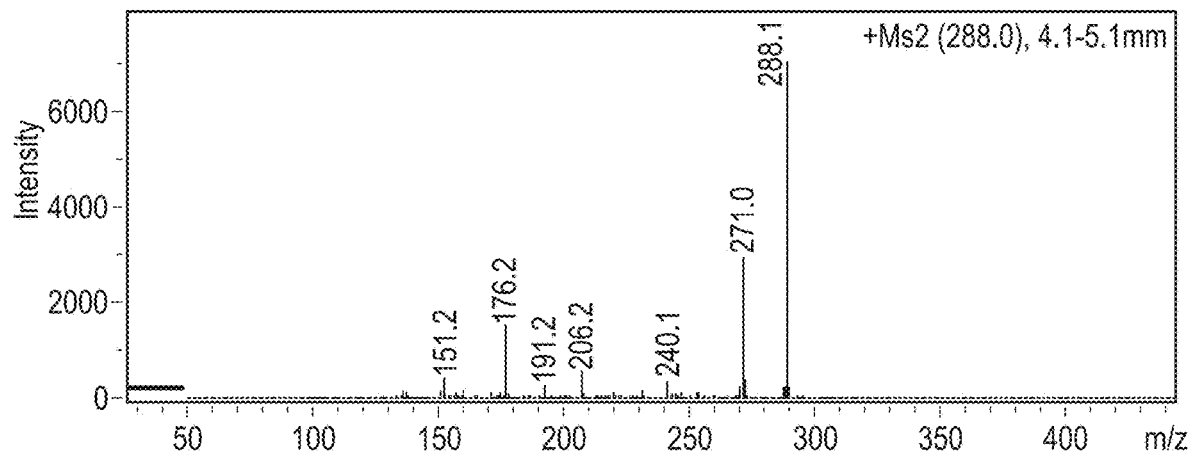
FIG. 16A: Product ion mass spectra of Tenofovir EIC 176,206,270+MS2 (288).
Figure 16B:
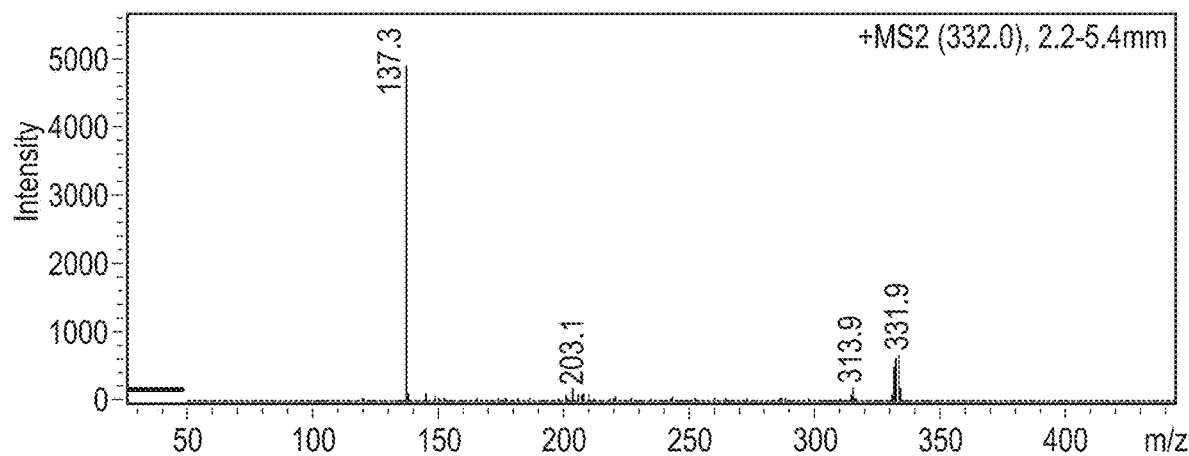
FIG. 16B: Product ion mass spectra of 2'-Deoxyadenosine 5'-phosphate EIC 136+MS2(332) in positive ionization mode.

The MS peaks that were obtained from these compounds (tenofovir and 2'-deoxyadenosine 5'-phosphate) are shown in FIG. 16.

Figure 17A:
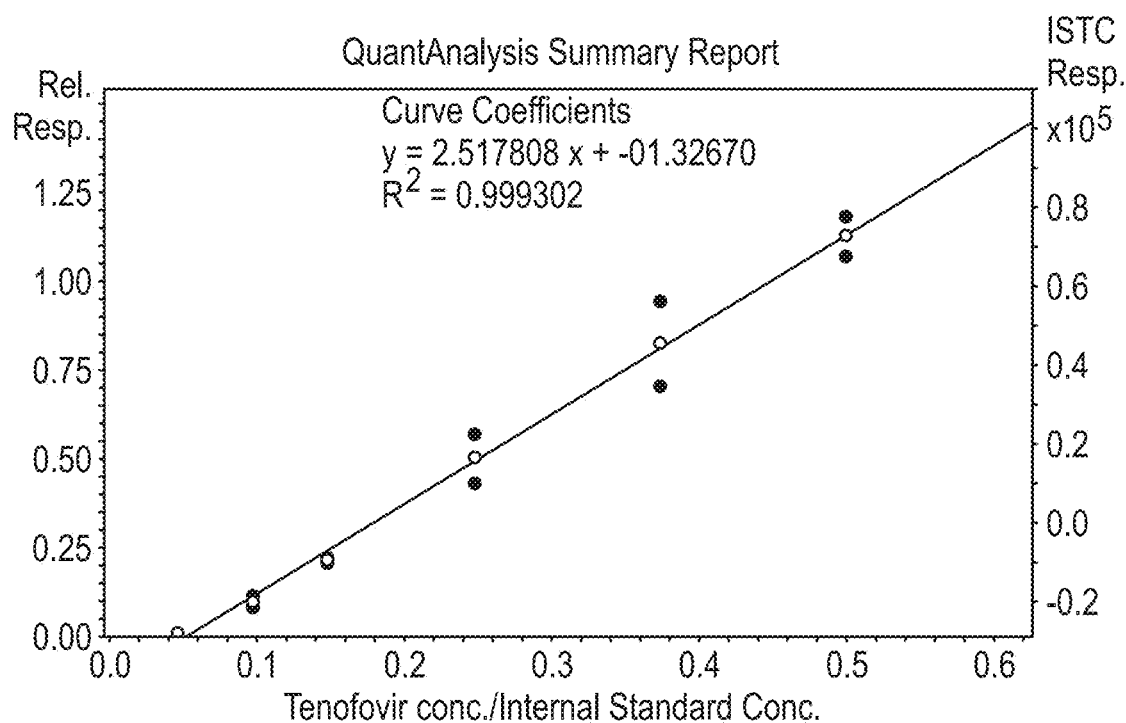
FIG. 17A: Calibration curve for tenofovir in blood.
Figure 17B:
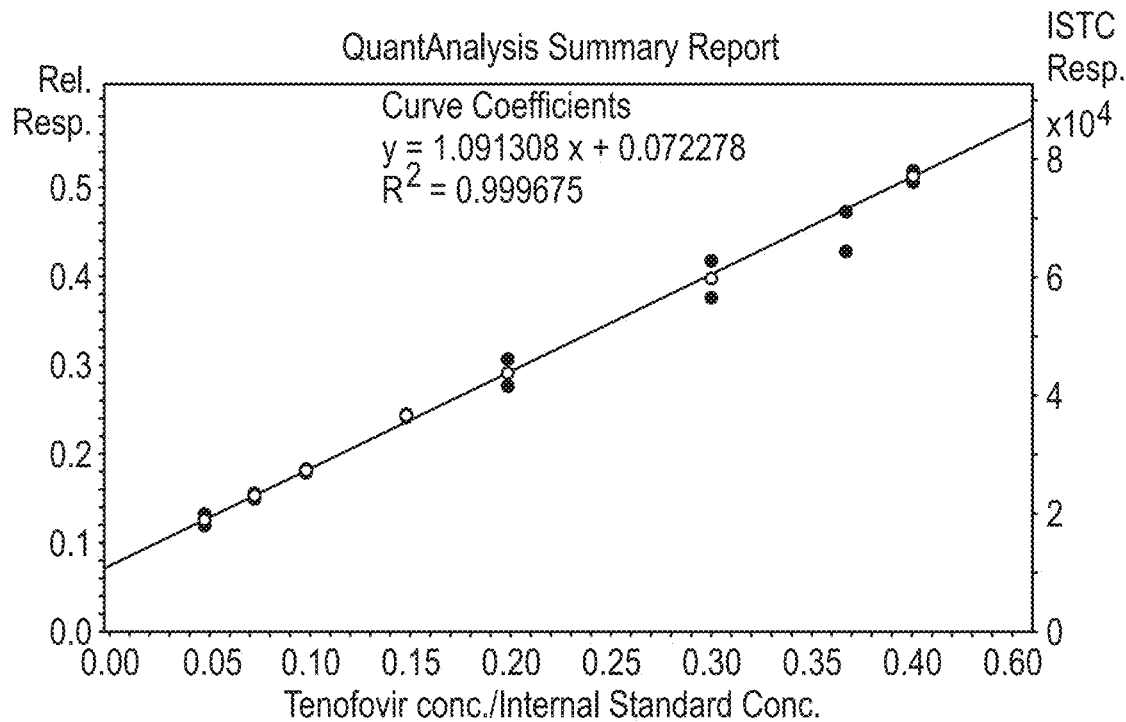
FIG. 17B: Calibration Curve for tenofovir in brain. Various concentrations of tenofovir and a fixed concentration of the internal standard were spiked into blood samples (FIG. 17A), or into brain homogenates (FIG. 17B), and the samples were processed for deproteinization as described in the text. The MS responses were measured after adding these samples to LC-MS and were plotted as a function of the ratio between tenofovir and the internal standard. The ratio of tenofovir to internal standard allowed us to calculate percent recovery of tenofovir. Each sample was measured in duplicates and the result of each duplicate is shown in the graph (filled circles), The average value of each duplicate (empty circles) were used to plot the calibration curve. The concentration range of the spiked tenofovir was 100-1000 ng/mL for the blood and 50-400 ng/mL for the brain.

After establishing conditions for the LC-MS as described above, brain homogenate and blood samples were prepared and spiked known concentrations of tenofovir and a fixed concentration of the internal standard into the blood samples and the brain homogenates. The specimens were then processed by adding 180 μL of 10% Tri Chloro Acetic acid (TCA) to 300 μL of the homogenate followed by centrifugation to obtain a clear solution of blood or brain extracts. The supernatant that was obtained by the centrifugation was neutralized with 200 μL of 1% NaOH. The MS signals that were obtained from each sample were plotted as a function of the spiked tenofovir concentration to obtain calibration curves for the blood (FIG. 17A) and for the brain (FIG. 17B).

As can be seen from FIG. 17, tenofovir concentrations as low as 50 ng could have been measured accurately by this method and, when lower concentrations in tissue extracts were obtained, the actual concentration was calculated by an extrapolation, as the calibration curve was linear for the relevant concentration range.

Pharmacokinetic Studies

For the PK studies, vesicles optimized as described above were used for the delivery of tenofovir into the brain. This formulation contains in 1 mL:10 mg GLH 19 and GLH 20 in a ratio of 2/1, 1 mg GLH-55b, 2.4 mg cholesteryl hemisuccinate, 1.6 mg cholesterol, 2.5 mg stearyl amine, and 5 mg tenofovir. The vesicles were prepared by film hydration followed by sonication using a HEPES hydration buffer. The vesicles size that was obtained with this optimal formulation was ~100 nm in diameter, the vesicles were positively charged with a zeta potential of about 30 mV and 20% of the added tenofovir was encapsulated under these conditions.

In the first set of the PK experiments, mice (average weight was 22 g per mouse) were injected with vesicles that contained encapsulated tenofovir or with empty vesicles followed by free tenofovir (4 mice per group). Since during the encapsulation procedure some of the tenofovir remains non-encapsulated (the amount of the non-encapsulated tenofovir depends on the encapsulation conditions, as has been shown in previous studies and in this particular case the amount of the encapsulated tenofovir was 1 mg/mL vesicles) and the vesicles were not purified before injection (to avoid dilution of the vesicles that occur during the purification process), the dose of the tenofovir was adjusted so that in each case an equal dose of total tenofovir was injected. The dose of the total tenofovir was 34 mg/kg, out of which 6.8 mg/kg was encapsulated (only when encapsulated tenofovir was injected). This dose of encapsulated tenofovir is equivalent to about 475 mg per human subject of an average weight of 70 Kg, which is within the dose range given to AIDS patients. Before the injection of the test material, mice were pretreated with 0.5 mg/kg pyridostigmine to inhibit choline esterases in the blood (unless otherwise stated), since vesicles that contain GLH-20 release their content in presence of choline esterases. At various times after the injection (15, 30, 75, 120 and 240 min), blood samples were withdrawn and the mice were perfused with 10 mL PBS and sacrificed. Brains were immediately removed after sacrificing the mice and brain homogenates were prepared by homogenizing the brains in PBS (4 mL PBS per gram brain). Extracts of the homogenates were then prepared by adding 180 µL of 10% TCA to 300 µL of the homogenate followed by centrifugation to obtain a clear solution of the brain extract. The supernatant that was obtained by the centrifugation was neutralized with 200 µL of 1% NaOH. Tenofovir concentration in the clear brain extract was determined by LC-MS, using the calibration curve which is described above in FIG. 17. The blood samples were centrifuged to separate the serum from the blood cells and processed in the same way as the brain homogenates. Tenofovir concentration was determined by LC-MS.

Figure 18:
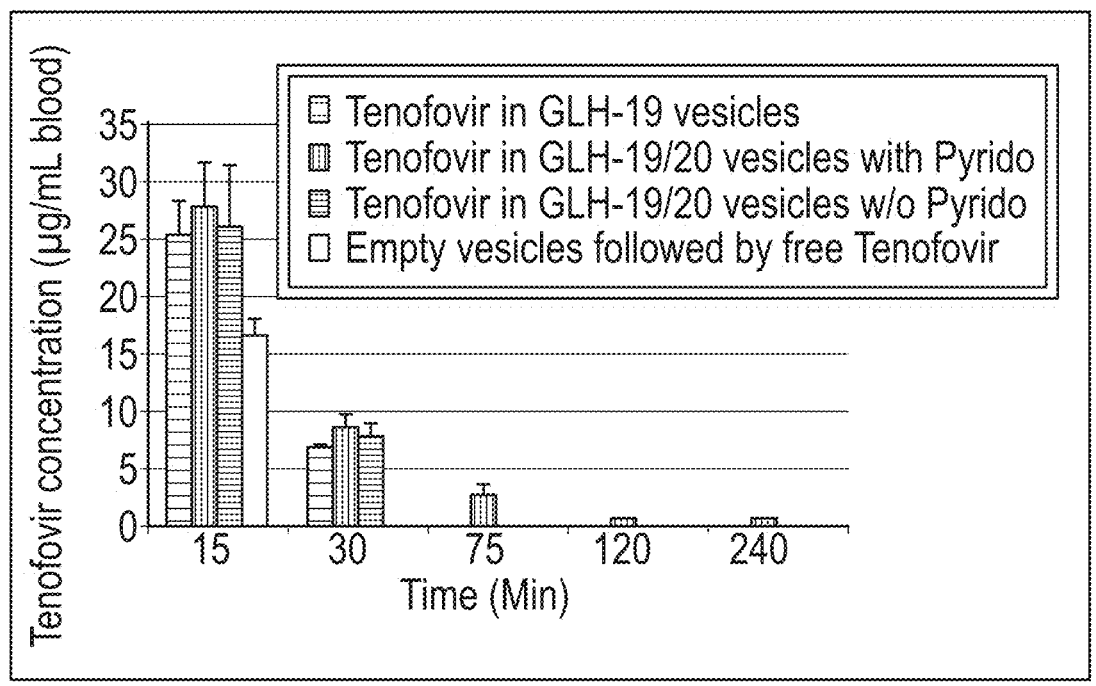
FIG. 18: Tenofovir concentration in the blood of mice after injecting them with tenofovir, which was either encapsulated in GLH-19 vesicles, or in vesicles made from a mixture of the bolas GLH-19 and GLH-20. In the latter case, animals were either pretreated with pyridostigmine (with pyrido) or did not receive the pyrido pretreatment (w/o pyrido). Another group of animals was injected with empty vesicles and then with free tenofovir. Results are mean of 4 mice±SD.

The results of the tenofovir concentrations in the blood at various times after the injection of the test material are shown in FIG. 18.

As can be seen from FIG. 18, the concentration of the blood tenofovir dropped quickly after the injection of the test material. The half-life of tenofovir in the blood was calculated to be about 20 min. The concentrations of tenofovir in the brain was determined in brain extracts prepared from the same animals, which were used to obtain the data for FIG. 18 and the results are shown in FIG. 19.

Figure 19:
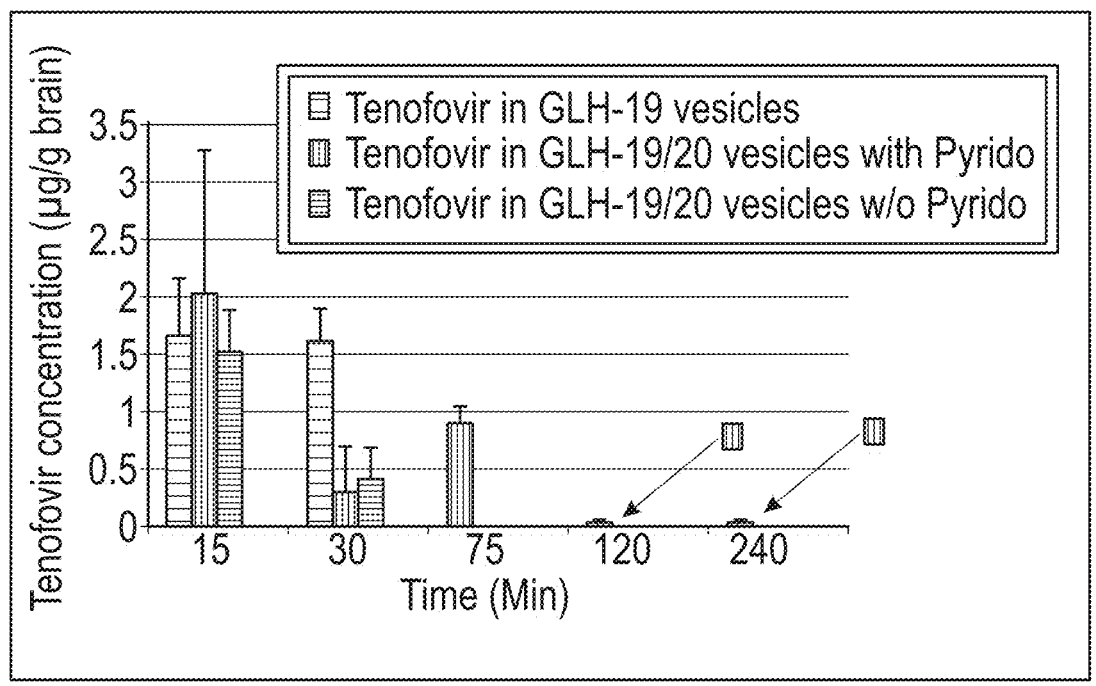
FIG. 19: Tenofovir concentration in the brain of mice after injecting them with tenofovir, which was either encapsulated in GLH-19 vesicles, or in vesicles made from a mixture of the bolas GLH-19 and GLH-20. In the latter case, animals were either pretreated with pyridostigmine (with pyrido) or did not receive the pyrido pretreatment (w/o pyriso). Another group of animals was injected with empty vesicles and then with free tenofovir, but tenofovir was not detected in the brain of this group of mice and therefore no bars were assigned for this group. Results are mean of 4 mice±SD.

From the results in FIG. 19, it can be seen that, when the mice were pretreated with pyrido, the half-life of tenofovir in the brain was longer than the half-life of tenofovir in the blood (compare data from FIG. 18 with data that were obtained with the same animals and that are presented in FIG. 19). Thus, the apparent half-life of tenofovir in the brain was about 40 min as compared to 20 minutes half-life of tenofovir in the blood of the same animals. The apparent half-life of tenofovir in the blood reflects both free tenofovir and encapsulated tenofovir, as the non-encapsulated tenofovir was not removed from the vesicles before the injection. Since the encapsulated tenofovir constituted only 20% of the injected tenofovir, the data indicate that the actual half-life of the encapsulated tenofovir in the blood is longer than 20 min. By comparison, in the brain, only encapsulated tenofovir enters into this organ, and the apparent half-life in the brain is likely identical to the actual half-life and it may be a reflection of the actual half-life of encapsulated tenofovir in the blood. When the animals were not pretreated with pyrido, the half-life in the brain was similar to the half-life of tenofovir in the blood, suggesting that most of the vesicles were opened in the blood by the blood choline esterases that were not inhibited by pyrido. Tenofovir encapsulated in GLH-19 vesicles did not persist long in the brain, in part because tenofovir was not released efficiently in the brain from vesicles that are not opened by AChE. The initial high concentration of tenofovir in the brain in animals that were injected with tenofovir encapsulated in GLH-19 vesicles, which are not opened by choline esterases, is probably due to the presence of encapsulated tenofovir in the brain a short time after the injection. Since tenofovir was not released in the brain from GLH-19 vesicles, it did not accumulate in the brain as in the case when tenofovir was encapsulated in vesicles made of a mixture of GLH-19 and GLH-20, which are opened and release their content in presence of AChE. The GLH-19 vesicles apparently were circulated back out of the brain without releasing their content in the brain.

In the second set of the PK studies, all the mice were pretreated with pyrido 15 min prior to the injection of 7.5 mg/kg tenofovir encapsulated in optimal vesicles or with 75 mg/kg free tenofovir with no vesicles. The results that show the concentrations of tenofovir in the brain at various times after the injection are shown in FIG. 20.

Figure 20:
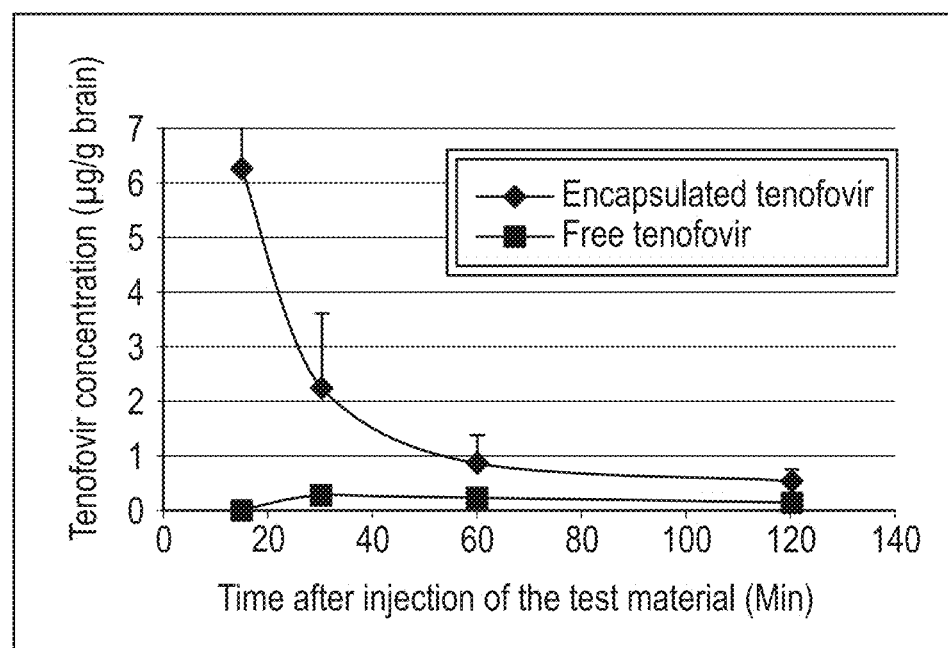
FIG. 20: Tenofovir concentrations in the brain of mice after injecting the mice with optimized V-Smart™ vesicles made in 1 mL HEPES from 10 mg GLH-19 and GLH-20 at the ratio of 2:1, 1 mg GLH-55a, 2.4 mg cholesteryl hemisuccinate, 1.6 mg cholesterol, 2.5 mg stearyl amine and 5 mg/mL tenofovir. Another group of mice were injected with free tenofovir. The total dose of tenofovir that was injected to the mice that received encapsulated tenofovir was 37.5 m/kg, out of which 7.5 mg/kg was encapsulated tenofovir. The total dose of tenofovir that was injected to the mice that received free tenofovir was 75 mg/kg. All animals were pretreated with 0.5 mg/kg pyrido. Results are mean of 5 mice±SD.

As can be seen from FIG. 20, the concentration of tenofovir in the brain after delivering the drug encapsulated in the optimized V-Smart™ vesicles was above the therapeutic threshold (which is estimated to be 100 ng/mL) at all the time points (up to 2 hours). After 15 min, the concentration of the tenofovir in the brain was higher than 6 micrograms per gram brain and, even at 60 min after the injection, the encapsulated tenofovir's concentration in the brain was about 1 microgram per mL, still one order of magnitude higher than the therapeutic levels and comparable to the blood level at this time point. The relatively rapid drop of tenofovir concentration in the brain may be explained by intracellular metabolism into the active metabolites of the drug, which are mono or dephosphorylated derivatives of tenofovir. An alternative possibility is that the brain pumps out tenofovir that was released in the brain from the vesicles, most probably by the PGp pump, which is a functional component of the BBB. Since the vesicles disclosed above have good cellular uptake, it appears that the rapid reduction in tenofovir concentrations in the brain is mostly due to intracellular metabolism into the active metabolites and only a small amount of tenofovir is removed from the brain by the Pgp pump. By comparison to encapsulated tenofovir, when the free drug was injected at a dose twice of the encapsulated dose, the concentrations of tenofovir in the brain were very low, below the measurable level and on the border of the detection limit, which is 40 ng/ml (FIG. 20). These results clearly show that our V-Smart™ vesicles are capable of delivering into the brain significant amounts of tenofovir, a drug that in its free form does not penetrate into the brain almost at all. These results indicate that the V-Smart™ vesicles described above, which were optimized for the delivery of tenofovir into the brain, may be beneficial in the treatment of neuro-HIV.

From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

REFERENCES

*Abu Hammad I, Popov M, Linder C, Grinberg S, Heldman E, Stepensky D (2011) Bolaamphiphilic nanovesicles for the delivery of proteins to the brain, submitted to the Journal of Controlled Release.

Agyare, E K, Kandimalla K K, Poduslo J F, Yu C C, Ramakrishnan M, Curran G L (2008) Development of a smart nano-vesicle to target cerebrovascular amyloid deposits and brain parenchymal plaques observed in Alzheimer's disease and cerebral amyloid angiopathy. Pharm Res November; 25 (11):2674-2684.

Fuhrhop J. H. and Wang T. (2004) Bolaamphiphiles, Chem. Rev. 104:2901-2937.

Gisslen M and Hagberg L and Hagberg (2001) Antiretroviral treatment of central nervous system HIV-1 infection: a Review. HIV Medicine (2001) 2, 97-104.

G Gnanarajan, A K Gupta, V Juyal, P Kumar, P K Yadav, P Kailash "A validated method for development of tenofovir as API and tablet dosage forms by UV spectroscopy" Pharm Analysis 2009 Vol 1 Issue 4 pp 351-353.

*Grinberg S, C. Linder, E. Heldman, Z. Weizman, and V. Kolot EP1360168, 2003, Nov. 12 and WO2002IL00043 and 20020116, Filed by B G Negev "Amphiphilic Derivatives for the Production of Vesicles, Micelles, Complexants, and Uses Thereof" in 2003

*Grinberg S., Linder C., Kolot V., Waner T., Wiesman Z., Shaubi E., Heldman E. (2005) Novel cationic amphiphilic derivatives from vernonia oil: synthesis and self-aggregation into bilayer vesicles, nanoparticles, and DNA complexants. Langmuir. 21(17):7638-7645.

*Grinberg S., Kolot V., Linder C., Shaubi E., Kas'yanov V., Deckelbaum R. J., Heldman E. (2008) Synthesis of novel cationic bolaamphiphiles from vernonia oil and their aggregated structures. Chem Phys Lipids 153(2):85-97.

*Grinberg, S., Kipnis, N., Linder, C., Kolot, V. and Heldman, E., (2010) Assymetric bolaamphiphiles from veronica oil designed for drug delivery. Eur. J. Lipid Sci. Technol., 112, 137-151.

*E. Heldman E, C. Linder, S. Grinberg Amphiphilic compounds and vesicles liposomes for organ-specified drug targeting" US patent Application 20060039962+ WO03047499—2003, Jun. 12

Highleyman, L (2009) HIV and the Brain BETA. 2009 Summer-Fall; 21(4):16-29.

*Hutter T, Linder C, Heldman E, Grinberg S (2011) Interfacial and self-assembly properties of bolaamphiphilic compounds derived from a multifunctional oil, Journal of Colloid and Interface Science, in press (doi: 10. 1016j. jcis. .08. 057).

Jonasdottir T J, Fisher D R, Borrebaek J, Bruland O S, Larsen R H (2006) First in vivo evaluation of liposome-encapsulated 223Ra as a potential alpha-particle-emitting cancer therapeutic agent. Anticancer Res. 26(4B):2841-2848.

Letendre S, Marquie-Beck J, Capparelli E, Best B, Clifford D, Collier A C, Gelman B B, McArthur J C, McCutchan J A, Morgello S, Simpson D, Grant I, Ellis R J; CHARTER Group. (2008) Validation of the CNS Penetration-Effectiveness rank for quantifying antiretroviral penetration into the central nervous system. Arch Neurol. 2008 January; 65(1):65-70.

*Linder C; Grinberg S; Heldman E "Nano-sized Particles Composing Multi-Headed Amphiphiles for Targeted Drug-Delivery" WO 2010128504 (A2) 2010.

Lu W, Tan Y Z, Hu K L and Jiang X G. (2005) Cationic albumin conjugated pegylated nanoparticle with its transcytosis ability and little toxicity against blood-brain barrier. Int J Pharm. May 13; 295 (1-2); 247-260.

New R. R. C. (ed). (1997) Liposomes. A Practical Approach. IRL Press, Oxford.

Newton H B (2006) Advances in strategies to improve drug delivery to brain tumors. Expert Rev Neurother. 6(10): 1495-509.

*Popov M., Linder C., Deckelbaum R. J., Grinberg S., Hansen I. H., Shaubi E., Waner T., Heldman E. (2009) Cationic vesicles from novel bolaamphiphilic compounds. *J Liposome Res.* 20(2):147-159.

*Popov M, Grinberg S, Linder C, Bachar Z, Waner T, Deckelbaum R, Heldman E. (2011) Site-directed decapsulation of bolaamphiphilic vesicles with enzymatic cleavable surface groups submitted to the *Journal of Controlled Release*.

*Puri, A., Loomis, K., Smith, B., Lee, J., Yavlovich, A., Heldman, E. and Blumenthal, R. (2009) Lipid-Based Nanoparticles as Pharmaceutical Drug Carriers: From Concepts to Clinic. *Crit Rev Ther Drug Carrier Syst*, 26(6): 523-580.

Saiyed Z, Gandhi N, and Nairi M (2010)Magnetic Nanoformulation of Azidothymidine 5'-triphosphate for Targeted Delivery across the Blood-Brain Barrier. *International Journal of Nanomedicine* 5:157-166

Songjiang Z and Lixiang W. (2009) Amyloid-Beta Associated with Chitosan Nano-Carrier has Favorable Immunogenicity and Permeates the BBB. *AAPS Pharm Sci Tech*, 10(3):900-905.

Spudich S and Antses B (2011) Central Nervous System Complications of HIV Infection. *Top. Antiviral Med* 19(2), 48-57.

Stern J, Freisleben H J, Janku S, Ring K. (1992) Black lipid membranes of tetraether lipids from *Thermoplasma acidophilum*, Biochim Biophys Acta 1128:227-236.

Varatharajan L and Thomas S. (2009) The transport of anti-HIV drugs across blood-CNS interfaces: Summary of current knowledge and recommendations for further Research *Antiviral Res.* 2009 May; 82(2): A99-A109.

*Wiesman Z., Dom N. B., Sharvit E., Grinberg S., Linder C., Heldman E., Zaccai M. (2007) Novel cationic vesicle platform derived from vernonia oil for efficient delivery of DNA through plant cuticle membranes. *J. Biotechnol.* 130(1):85-94.

*Zabicky J; Linder C; Grinberg S; Heldman E "Nano- and Mesosized Particles Comprising an Inorganic Core, Process and Applications Thereof" US2009011002

What is claimed is:

1. A formulation containing vesicles comprising one or more bolaamphiphilic compounds, cholesteryl hemisuccinate, cholesterol, stearyl amine, and an active agent which is tenofovir or fosamprenavir ({[(2R,3S)-1-[N-(2-methylpropyl)(4-aminobenzene)sulfonamido]-3-({[(3S)-oxolan-3-yloxy]carbonyl}amino)-4-phenylbutan-2-yl]oxy}phosphonic acid), wherein the pH has been adjusted to a pH of 7.5 or 8 using a buffer to maximize tenofovir encapsulation wherein for 1 mL of formulation the components are: 10 mg GLH 19 and GLH 20 in a ratio of 2/1, 1 mg GLH-55b, 2.4 mg cholesteryl hemisuccinate, 1.6 mg cholesterol, 2.5 mg stearyl amine, and 5 mg tenofovir or fosamprenavir ({[(2R,3S)-1-[N-(2-methylpropyl)(4-aminobenzene)sulfonamido]-3-({[(3S)-oxolan-3-yloxy]carbonyl}amino)-4-phenylbutan-2-yl]oxy}phosphonic acid);

and the buffer is a HEPES, wherein GLH 19 is

GLH 19 is

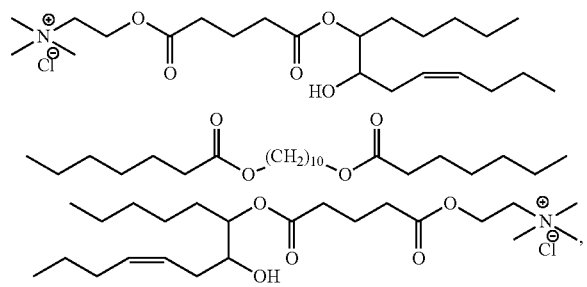

GLH 20 is

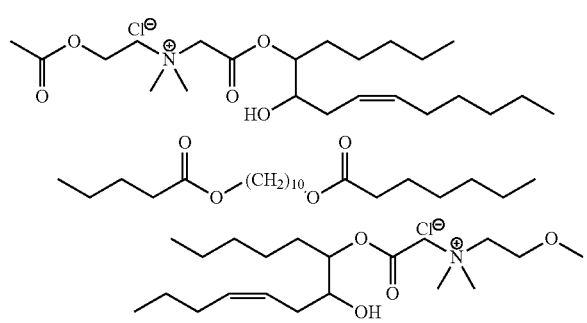

and

GLH 55b is

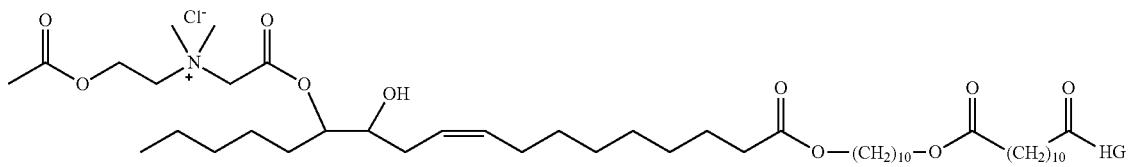

wherein

HG is

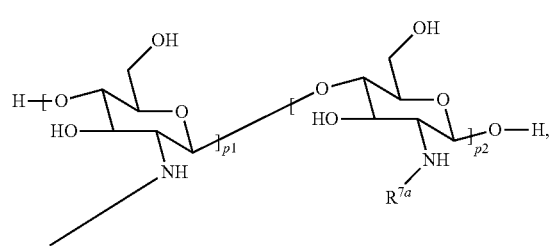

each p1 and p2 is an integer from 1-400, and $R^{7a}$ is H or an acyl group.

2. A formulation of claim 1 suitable for IV, IP, oral, or transdermal administration for delivery of the active agent above its therapeutic threshold of 100 ng/mL.

3. A formulation of claim 1 suitable for IV, IP, oral, or transdermal administration for delivery of the active agent above its therapeutic threshold of 100 ng/100 mL.

4. A formulation of claim 1 wherein for 1 mL of formulation the components are: 10 mg GLH 19 and GLH 20 in a ratio of 2/1, 1 mg GLH-55b, 2.4 mg cholesteryl hemisuccinate, 1.6 mg cholesterol, 2.5 mg stearyl amine, and 5 mg tenofovir; and the buffer is a HEPES buffer.

5. A formulation of claim 1, wherein the pH has been adjusted to a pH of 7.5.

\* \* \* \* \*